US008865912B2

(12) United States Patent
Qu et al.

(10) Patent No.: US 8,865,912 B2
(45) Date of Patent: Oct. 21, 2014

(54) BENZIMIDAZOLE DERIVATIVES AS PI3 KINASE INHIBITORS

(71) Applicant: GlaxoSmithKline LLC, Philadelphia, PA (US)

(72) Inventors: Junya Qu, Collegeville, PA (US); Ralph A. Rivero, Collegeville, PA (US); Robert Sanchez, Collegeville, PA (US); Rosanna Tedesco, Collegeville, PA (US)

(73) Assignee: GlaxoSmithKline LLC, Philadelphia, PA (US)

(*) Notice: Subject to any disclaimer, the term of this patent is extended or adjusted under 35 U.S.C. 154(b) by 0 days.

(21) Appl. No.: 14/164,414

(22) Filed: Jan. 27, 2014

(65) Prior Publication Data
US 2014/0142321 A1 May 22, 2014

Related U.S. Application Data

(63) Continuation of application No. 14/031,136, filed on Sep. 19, 2013, now Pat. No. 8,674,090, which is a continuation of application No. 13/876,853, filed as application No. PCT/US2011/052857 on Sep. 23, 2011, now abandoned.

(60) Provisional application No. 61/390,314, filed on Oct. 6, 2010, provisional application No. 61/528,397, filed on Aug. 29, 2011.

(51) Int. Cl.
C07D 235/08 (2006.01)
C07D 235/24 (2006.01)
C07D 417/10 (2006.01)
C07D 413/10 (2006.01)
C07D 405/10 (2006.01)
C07D 409/10 (2006.01)
C07D 405/04 (2006.01)
C07D 403/10 (2006.01)
C07D 403/04 (2006.01)
C07D 235/10 (2006.01)
C07D 401/10 (2006.01)
C07D 413/04 (2006.01)
C07D 417/04 (2006.01)

(52) U.S. Cl.
CPC ............ C07D 235/08 (2013.01); C07D 235/24 (2013.01); C07D 417/10 (2013.01); C07D 413/10 (2013.01); C07D 405/10 (2013.01); C07D 409/10 (2013.01); C07D 405/04 (2013.01); C07D 403/10 (2013.01); C07D 403/04 (2013.01); C07D 235/10 (2013.01); C07D 401/10 (2013.01); C07D 413/04 (2013.01); C07D 417/04 (2013.01)
USPC ..................... 548/304.4; 548/307.4

(58) Field of Classification Search
CPC ..................................... C07D 235/08
USPC ......................... 548/304.4, 307.4
See application file for complete search history.

(56) References Cited

U.S. PATENT DOCUMENTS

| | | | |
|---|---|---|---|
| 5,502,187 A | 3/1996 | Ayers et al. |
| 7,019,021 B2 | 3/2006 | Esser et al. |
| 7,223,757 B2 | 5/2007 | Wittman et al. |
| 2004/0024037 A1 | 2/2004 | Ryu et al. |
| 2004/0063938 A1 | 4/2004 | Caron et al. |
| 2005/0137234 A1 | 6/2005 | Bressi et al. |
| 2005/0209277 A1 | 9/2005 | Crawford et al. |
| 2005/0272765 A1 | 12/2005 | Feng et al. |
| 2006/0160872 A1 | 7/2006 | Norman et al. |
| 2007/0066606 A1 | 3/2007 | Stahle et al. |
| 2007/0142328 A1 | 6/2007 | Chapdelaine et al. |
| 2007/0142382 A1 | 6/2007 | Chapdelaine et al. |
| 2008/0293771 A1 | 11/2008 | Zhou et al. |
| 2009/0018112 A1 | 1/2009 | Chapdelaine et al. |
| 2009/0036454 A1 | 2/2009 | Chapdelaine et al. |
| 2009/0181963 A1 | 7/2009 | Dehnhardt et al. |
| 2009/0253161 A1 | 10/2009 | Franz et al. |
| 2009/0264384 A1 | 10/2009 | Didsbury et al. |
| 2010/0179147 A1 | 7/2010 | Chang et al. |
| 2010/0286190 A1 | 11/2010 | Mitchell et al. |

FOREIGN PATENT DOCUMENTS

| | | |
|---|---|---|
| AU | 9517656 | 4/1994 |
| BR | 200306016 | 12/2003 |
| CA | 1834090 | 3/2005 |
| DE | 102006025777 | 12/2007 |
| EP | 400835 | 12/1990 |
| EP | 425921 | 5/1991 |
| EP | 546358 | 6/1993 |
| EP | 631780 | 1/1995 |

(Continued)

OTHER PUBLICATIONS

PCT/US11/52857 Written Opinion of the International Search Authority—Feb. 7, 2012.
PCT/US2011/052857 search report for EP11831214 (Feb. 21, 2014).

Primary Examiner — Rebecca Anderson
(74) Attorney, Agent, or Firm — J. Scott Young

(57) ABSTRACT

This invention relates to the use of benzimidazole derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of benzimidazoles in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries. More suitably, the present invention relates to PI3Kβ selective benzimidazoles compounds for treating cancer.

4 Claims, No Drawings

(56) References Cited

FOREIGN PATENT DOCUMENTS

| | | |
|---|---|---|
| EP | 706795 | 4/1996 |
| EP | 1553091 | 7/2005 |
| EP | 1878724 | 1/2008 |
| FR | 2822463 | 3/2001 |
| FR | 2827862 | 7/2001 |
| FR | 2928924 | 3/2008 |
| JP | 08067674 | 3/1996 |
| JP | 2000/323278 | 5/1999 |
| JP | 2007/063261 | 8/2005 |
| JP | 2011003793 | 6/2009 |
| WO | WO 93/20078 | 10/1993 |
| WO | WO 93/23396 | 11/1993 |
| WO | WO 97/25041 | 7/1997 |
| WO | WO 97/31635 | 9/1997 |
| WO | WO 97/33873 | 9/1997 |
| WO | WO 98/39343 | 9/1998 |
| WO | WO 00/59905 | 10/2000 |
| WO | WO 00/66564 | 11/2000 |
| WO | WO 01/05758 | 1/2001 |
| WO | WO 01/12600 | 2/2001 |
| WO | WO 01/21634 | 3/2001 |
| WO | WO 01/40227 | 6/2001 |
| WO | WO 01/57020 | 8/2001 |
| WO | WO 02/50062 | 6/2002 |
| WO | WO 02/59088 | 8/2002 |
| WO | WO 02/072549 | 9/2002 |
| WO | WO 02/074769 | 9/2002 |
| WO | WO 02/076960 | 10/2002 |
| WO | WO 02/081463 | 10/2002 |
| WO | WO 02/085853 | 10/2002 |
| WO | WO 02/085892 | 10/2002 |
| WO | WO 02/092575 | 11/2002 |
| WO | WO 02/102978 | 12/2002 |
| WO | WO 03/007945 | 1/2003 |
| WO | WO 03/015769 | 2/2003 |
| WO | WO 03/024937 | 3/2003 |
| WO | WO 03/028650 | 4/2003 |
| WO | WO 03/030902 | 4/2003 |
| WO | WO 03/040114 | 5/2003 |
| WO | WO 03/045929 | 6/2003 |
| WO | WO 03/062392 | 7/2003 |
| WO | WO 03/068857 | 8/2003 |
| WO | WO 03/077855 | 9/2003 |
| WO | WO 03/077914 | 9/2003 |
| WO | WO 03/078421 | 9/2003 |
| WO | WO 2004/005253 | 1/2004 |
| WO | WO 2004/014905 | 2/2004 |
| WO | WO 2004/043913 | 5/2004 |
| WO | WO 2004/052862 | 6/2004 |
| WO | WO 2004/063169 | 7/2004 |
| WO | WO 2004/082621 | 9/2004 |
| WO | WO 2004/089942 | 10/2004 |
| WO | WO 2004/093912 | 11/2004 |
| WO | WO 2004/098494 | 12/2004 |
| WO | WO 2005/004607 | 1/2005 |
| WO | WO 2005/023251 | 3/2005 |
| WO | WO 2005/028447 | 3/2005 |
| WO | WO 2005/028448 | 3/2005 |
| WO | WO 2005/051928 | 6/2005 |
| WO | WO 2005/051929 | 6/2005 |
| WO | WO 2005/079791 | 9/2005 |
| WO | WO 2005/082904 | 9/2005 |
| WO | WO 2005/090303 | 9/2005 |
| WO | WO 2005/112932 | 12/2005 |
| WO | WO 2006/023400 | 3/2006 |
| WO | WO 2006/034003 | 3/2006 |
| WO | WO 2006/050053 | 5/2006 |
| WO | WO 2006/053342 | 5/2006 |
| WO | WO 2006/060737 | 6/2006 |
| WO | WO 2006/076246 | 7/2006 |
| WO | WO 2006/132625 | 12/2006 |
| WO | WO 2007/008539 | 1/2007 |
| WO | WO 2007/023880 | 3/2007 |
| WO | WO 2007/026962 | 3/2007 |
| WO | WO 2007/027594 | 3/2007 |
| WO | WO 2007/030080 | 3/2007 |
| WO | WO 2007/039285 | 4/2007 |
| WO | WO 2007/054965 | 5/2007 |
| WO | WO 2007/071965 | 5/2007 |
| WO | WO 2007/084390 | 7/2007 |
| WO | WO 2007/087066 | 8/2007 |
| WO | WO 2007/089548 | 8/2007 |
| WO | WO 2007091950 | 8/2007 |
| WO | WO 2007/101347 | 9/2007 |
| WO | WO 2007/115077 | 10/2007 |
| WO | WO 2007/134169 | 11/2007 |
| WO | WO 2007/147647 | 12/2007 |
| WO | WO 2008/009348 | 1/2008 |
| WO | WO 2008/012623 | 1/2008 |
| WO | WO 2008/019309 | 2/2008 |
| WO | WO 2008/020920 | 2/2008 |
| WO | WO 2008/051494 | 5/2008 |
| WO | WO 2008/052072 | 5/2008 |
| WO | WO 2008/063300 | 5/2008 |
| WO | WO 2008/090181 | 7/2008 |
| WO | WO 2008/096829 | 8/2008 |
| WO | WO 2008/107478 | 9/2008 |
| WO | WO 2008/108741 | 9/2008 |
| WO | WO 2008/150446 | 12/2008 |
| WO | WO 2009/000413 | 12/2008 |
| WO | WO 2009/007421 | 1/2009 |
| WO | WO 2009/007422 | 1/2009 |
| WO | WO 2009/025793 | 2/2009 |
| WO | WO 2009/027736 | 3/2009 |
| WO | WO 2009/059208 | 5/2009 |
| WO | WO 2009/068482 | 6/2009 |
| WO | WO 2009/079011 | 6/2009 |
| WO | WO 2009/087224 | 7/2009 |
| WO | WO 2009/087225 | 7/2009 |
| WO | WO 2009/092566 | 7/2009 |
| WO | WO 2009/118382 | 10/2009 |
| WO | WO 2009/118384 | 10/2009 |
| WO | WO 2009/126691 | 10/2009 |
| WO | WO 2009/147431 | 12/2009 |
| WO | WO 2009/157429 | 12/2009 |
| WO | WO 2010/003048 | 1/2010 |
| WO | WO 2010/006096 | 1/2010 |
| WO | WO 2010/085684 | 7/2010 |
| WO | WO 2010/107739 | 9/2010 |
| WO | WO 2010/108187 | 9/2010 |
| WO | WO 2010099527 | 9/2010 |
| WO | WO 2010106072 | 9/2010 |
| WO | WO 2010/112874 | 10/2010 |
| WO | WO 2010/114726 | 10/2010 |
| WO | WO 2010/118208 | 10/2010 |
| WO | WO 2010/126922 | 11/2010 |
| WO | WO 2010/135524 | 11/2010 |
| WO | WO 2010126745 | 11/2010 |
| WO | WO 2010/138487 | 12/2010 |
| WO | WO 2010/141360 | 12/2010 |
| WO | WO 2010144686 | 12/2010 |
| WO | WO 2011009010 | 1/2011 |
| WO | WO 2011053292 | 5/2011 |
| WO | WO 2011073492 | 6/2011 |
| WO | WO 2011074560 | 6/2011 |

BENZIMIDAZOLE DERIVATIVES AS PI3 KINASE INHIBITORS

CROSS-REFERENCE TO RELATED APPLICATIONS

This application is filed as a continuation application of U.S. Ser. No. 14/031,136 filed on Sep. 19, 2013, which is a continuation of U.S. Ser. No. 13/876,853 filed on Mar. 29, 2013 (now abandoned), which was filed pursuant to 35 USC 371 as a United States National Phase Application of International Patent Application Serial No. PCT/US2011/052857 filed on Sep. 23, 2011, which claims priority from 61/390,314 filed on Oct. 6, 2010 and 61/528,397 filed on Aug. 29, 2011 in the United States.

FIELD OF THE INVENTION

This invention relates to the use of benzimidazole derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of benzimidazoles in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries. More suitably, the present invention relates to PI3Kβ selective benzimidazoles compounds for treating cancer.

BACKGROUND OF THE INVENTION

The phosphoinositide 3-kinase (PI3K) pathway is among the most commonly activated in human cancer and the importance in carcinogenesis is well established (Samuels Y and Ericson K. Oncogenic PI3K and its role in cancer. *Current Opinion in Oncology*, 2006; 18:77-82). Initiation of signaling begins with the phosphorylation of phosphatidylinositol-4,5-bisphosphate (PIP2) to produce phosphatidylinositol-3,4,5-P3 (PIP3). PIP3 is a critical second messenger which recruits proteins that contain pleckstrin homology domains to the cell membrane where they are activated. The most studied of these proteins is AKT which promotes cell survival, growth, and proliferation.

The PI3K family consists of 15 proteins that share sequence homology, particularly within their kinase domains, but have distinct substrate specificities and modes of regulation (Vivanco I and Sawyers C L. The phosphatidylinositol 3-kinase-AKT pathway in human cancer. *Nature Reviews Cancer*, 2002; 2:489-501). Class I PI3Ks are heterodimers consisting of a p110 catalytic subunit complexed to one of several regulatory subunits collectively referred to as p85 and have been the most extensively studied in the context of tumorgenesis. The class 1A PI3K catalytic subunits comprise the p110α, p110β, and p110δ isoforms, which associate with one of five different regulatory subunits encoded by three separate genes. A single class 1B PI3K catalytic isoform p110γ interacts with one of two associated regulatory subunits (Crabbe T, Welham M J, Ward S G, The PI3k inhibitor arsenal: choose your weapon *Trends in Biochem Sci*, 2007; 32:450-456). Class 1 PI3Ks are primarily responsible for phosphorylating the critical PIP2 signaling molecule.

The link between the PI3K pathway and cancer was confirmed by a study which identified somatic mutations in the PIK3CA gene encoding the p110α protein. Subsequently, mutations in PIK3CA have been identified in numerous cancers including colorectal, breast, glioblastomas ovarian and lung. In contrast to PIK3CA, no somatic mutations in the β isoform have been identified. However, in overexpression studies, the PI3Kβ isoform has been implicated as necessary for transformation induced by the loss or inactivation of the PTEN tumor suppressor both in vitro and in vivo (Torbett N E, Luna A, Knight Z A, et al., A chemical screen in diverse breast cancer cell lines reveals genetic enhancers and suppressors of sensitivity to PI3K isotype-selective inhibition. *Biochem J* 2008; 415:97-110; Zhao J J, Liu Z, Wang L, Shin E, Loda M F, Roberts T M, The oncogenic properties of mutant p110a and p110b phosphatidylinositol 3-kinases in human mammary epithelial cells. *Proc Natl Acad Sci USA* 2005; 102: 18443-8). Consistent with this finding, overexpression of the PIK3CB gene has been identified in some bladder, colon, glioblastomas and leukemias and siRNA mediated knockdown of p110β in glioblastoma cell lines results in suppression of tumor growth in vitro and in vivo (Pu P, Kang C, Zhang Z, et al., Downregulation of PIK3CB by siRNA suppresses malignant glioma cell growth in vitro and in vivo. *Technolo Cancer Res Treat* 2006; 5:271-280). More recent data using shRNA demonstrated that downregulation of p110β and not p110α resulted in PI3K pathway inactivation and subsequent inactivation of tumor cell growth in PTEN deficient cancers cells both in vitro and in vivo (Wee S, Wiederschain, Maira S-M, Loo A, Miller C, et al., PTEN-deficient cancers depend on PIK3CB. *Proc Natl Acad Sci* 2008; 105:13057-13062). Consistent with a role of PIK3CB signaling in PTEN null tumors, p110β was reported to be essential to the transformed phenotype in a PTEN-null prostate cancer model (Jia S, Liu Z, Zhang S, Liu P, Zhang L, et al., Essential roles of PI(3)K-p110b in cell growth, metabolism and tumorgenesis. *Nature* 2008; 10:1038).

Further, it has been reported that fibrogenesis, including systemic sclerosis (SSc), arthritis, nephropahty, liver cirrhosis, and some cancers, are related to PTEN deficiency and corresponding PI3K-Akt overexpression (Parapuram, S. K., et al., Loss of PTEN expression by dermal fibroblasts causes skin fibrosis. J. of Investigative Dermatology, advance online publication 9 Jun. 2011; doi: 10.1038/jid.2011.156). Taken together, these findings indicate PI3K p110β as a promising target for cancer and other syndromes related to PTEN loss (Hollander, M. Christine; Blumenthal, Gideon M.; Dennis, Phillip P.; PTEN loss in the continuum of common cancers, rare syndromes and mouse models. *Nature Reviews/Cancer* 2011; 11: 289-301). It is therefore desirable to create a potent, selective inhibitor of PI3K-β.

SUMMARY OF THE INVENTION

This invention relates to novel compounds of formula (I):

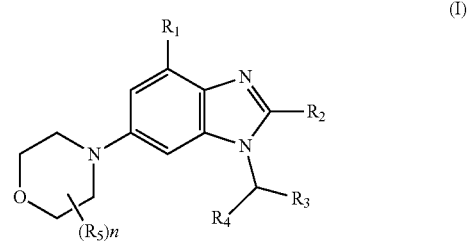

wherein

R1 is selected from H, $C_{1-6}$alkyl, alkoxy, hydroxy, halogen, —CN, —NH$_2$, —NHC(O)Ra, —NHSO$_2$Ra, —CO$_2$H, —CO$_2$Ra, —CONHRb, —CONH$_2$, —CH$_2$OH, and heteroaryl wherein the heteroaryl may be substituted by one or two $C_{1-3}$alkyl groups;

R2 is selected from H, —NHRa, alkoxy, halogen, —CF$_3$, —CHF$_2$, and $C_{1-6}$alkyl;

R3 is selected from aryl and heteroaryl, wherein said aryl or heteroaryl may be substituted by one to three Rc;

R4 is selected from H or Ra;

each R5 is independently selected from $C_{1-6}$alkyl;

each Ra is independently selected from $C_{1-3}$alkyl;

Rb is selected from $C_{1-3}$alkyl, and SO$_2$Me;

each Rc is independently selected from $C_{1-3}$alkyl, halogen, —CF$_3$, and hydroxy; and n is 0-2, or a pharmaceutically acceptable salt thereof.

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm in a mammal in need thereof.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm in a mammal in need thereof.

In another aspect of the present invention, there is provided a pharmaceutical composition comprising a compound of formula (I) (including any particular sub-generic formula described herein) or a pharmaceutically acceptable salt thereof for use in the treatment of a susceptible neoplasm in a mammal in need thereof.

DETAILED DESCRIPTION OF THE INVENTION

This invention is directed to compounds of Formula (I).

According to another embodiment, the invention includes compounds of Formula (I)(A), (I)(A)

wherein

R1 is selected from H, $C_{1-6}$alkyl, alkoxy, hydroxy, halogen, —CN, —NH$_2$, —NHC(O)Ra, —NHSO$_2$Ra, —CO$_2$H, —CO$_2$Ra, —CONHRb, —CONH$_2$, —CH$_2$OH, and heteroaryl wherein the heteroaryl may be substituted by one or two $C_{1-3}$alkyl groups, wherein the heteroaryl is selected from the group consisting of: pyrazolyl, triazolyl, tetrazolyl, oxazolyl and imidazolyl;

R2 is selected from H, —NHRa, alkoxy, halogen, —CF$_3$, —CHF$_2$, and $C_{1-6}$alkyl;

R3 is selected from aryl and heteroaryl, wherein said aryl or heteroaryl may be substituted by one to three Rc;

R4 is selected from H or Ra;

each R5 is independently selected from $C_{1-6}$alkyl;

each Ra is independently selected from $C_{1-3}$alkyl;

Rb is selected from $C_{1-3}$alkyl, and —SO$_2$Me;

each Rc is independently selected from $C_{1-3}$alkyl, halogen, —CF$_3$, and hydroxy; and n is 0-2, or a pharmaceutically acceptable salt thereof.

According to another embodiment, the invention includes compounds of Formula (I)(B), (I)(B)

wherein

R1 is selected from H, $C_{1-6}$alkyl, alkoxy, hydroxy, halogen, —CN, —NH2, —NHC(O)Ra, —NHSO$_2$Ra, —CO$_2$H, —CO$_2$Ra, —CONHRb, —CONH$_2$, —CH$_2$OH, and heteroaryl wherein the heteroaryl may be substituted by one or two $C_{1-3}$alkyl groups;

R2 is selected from H, —NHRa, alkoxy, halogen, —CF$_3$, —CHF$_2$, and $C_{1-6}$alkyl;

R3 is selected from aryl and heteroaryl, wherein said aryl or heteroaryl may be substituted by one to three Rc, and wherein the aryl or heteroaryl are selected from phenyl, naphthyl, benzothienyl, quinolinyl, isoquinolinyl, and quinazolinyl;

R4 is selected from H or Ra;

each R5 is independently selected from $C_{1-6}$alkyl;

each Ra is independently selected from $C_{1-3}$alkyl;

Rb is selected from $C_{1-3}$alkyl, and —SO$_2$Me;

each Rc is independently selected from $C_{1-3}$alkyl, halogen, —CF$_3$, and hydroxy; and n is 0-2, or a pharmaceutically acceptable salt thereof.

According to another embodiment, the invention includes compounds of Formula (I)(B) wherein each Rc is independently $C_{1-3}$alkyl, F or Cl, and n is 0.

According to another embodiment, the invention includes compounds of Formula (I)(B) wherein each Rc is independently CF$_3$ or F, and n is 0.

According to another embodiment, the invention includes the compounds of Formula (I)(C)

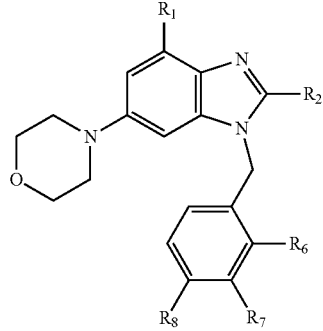

(I)(C)

wherein
R1 is selected from H, $C_{1-6}$alkyl, alkoxy, hydroxy, halogen, —CN, —NHC(O)Ra, —NHSO$_2$Ra, —CO$_2$H, —CO$_2$Ra, —CONHRb, —CONH$_2$, —CH$_2$OH, and heteroaryl wherein the heteroaryl may be substituted by one or two $C_{1-3}$alkyl groups;
R2 is selected from H, —NHRa, alkoxy or $C_{1-6}$alkyl;
each of R6, R7, and R8 is independently selected from $C_{1-3}$alkyl, halogen, —CF$_3$, and hydroxyl, or R6 and R7 combine to form a bi-cyclic aryl or heteroaryl, or R7 and R8 combine to form a bi-cyclic aryl or heteroaryl;
each Ra is independently selected from $C_{1-3}$alkyl; and
Rb is selected from $C_{1-3}$alkyl or —SO$_2$Me;
or a pharmaceutically acceptable salt thereof.

According to another embodiment, the invention includes the compounds of Formula (I)(D)

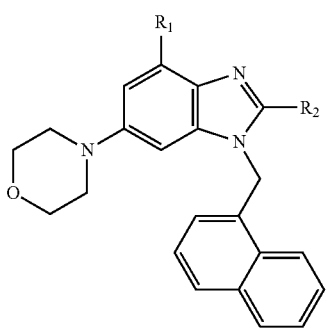

(I)(D)

wherein
R1 is selected from H, $C_{1-6}$alkyl, alkoxy, hydroxy, halogen, —CN, —NHC(O)Ra, —NHSO$_2$Ra, —CO$_2$H, —CO$_2$Ra, —CONHRb, —CONH$_2$, —CH$_2$OH, and heteroaryl wherein the heteroaryl may be substituted by one or two $C_{1-3}$alkyl groups;
R2 is selected from H, NHRa, alkoxy or $C_{1-6}$alkyl;
each Ra is independently selected from $C_{1-3}$alkyl; and
Rb is selected from $C_{1-3}$alkyl or SO$_2$Me;
or a pharmaceutically acceptable salt thereof.

According to another embodiment, the invention includes the compounds of Formula (I)(E)

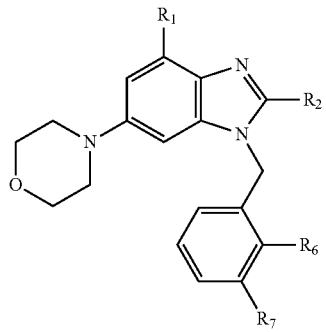

(I)(E)

wherein
R1 is selected from H, $C_{1-6}$alkyl, alkoxy, hydroxy, halogen, —CN, —NHC(O)Ra, —NHSO$_2$Ra, —CO$_2$H, —CO$_2$Ra, —CONHRb, —CONH$_2$, —CH$_2$OH, and heteroaryl wherein the heteroaryl may be substituted by one or two $C_{1-3}$alkyl groups;
R2 is H, NHRa, alkoxy or $C_{1-6}$alkyl;
each of R6 and R7 is independently selected from $C_{1-3}$alkyl, halogen, —CF$_3$, and hydroxyl;
each Ra is independently $C_{1-3}$alkyl; and
Rb is $C_{1-3}$alkyl or SO$_2$Me;
or a pharmaceutically acceptable salt thereof.

According to another embodiment, the invention includes compounds:
2-(1-methylethyl)-6-(4-morpholinyl)-1-(1-naphthalenylmethyl)-1H-benzimidazol-4-ol,
2-ethyl-6-(4-morpholinyl)-1-(1-naphthalenylmethyl)-1H-benzimidazol-4-ol,
1-[2,3-dichlorophenyl)methyl]-2-(1-methylethyl)-6-(4-morpholinyl)-1H-benzimidazol-4-ol,
1-[2,3-dichlorophenyl)methyl]-4-fluoro-2-methyl-6-(4-morpholinyl)-1H-benzimidazole,
1-[2,3-dichlorophenyl)methyl]-2-ethyl-6-(4-morpholinyl)-1H-benzimidazol-4-ol,
4-fluoro-2-methyl-6-(4-morpholinyl)-1-(1-naphthalenylmethyl)-1H-benzimidazole,
2-ethyl-4-fluoro-6-(4-morpholinyl)-1-(1-naphthalenylmethyl)-1H-benzimidazole,
2-methyl-6-(4-morpholinyl)-1-(1-naphthalenylmethyl)-1H-benzimidazole-4-carboxylic acid,
1-[2,3-dichlorophenyl)methyl]-2-ethyl-4-fluoro-6-(4-morpholinyl)-1H-benzimidazole,
2-methyl-6-(4-morpholinyl)-1-(1-naphthalenylmethyl)-4-(1H-pyrazol-5-yl)-1H-benzimidazole,
1-[2,3-dichlorophenyl)methyl]-2-methyl-6-(4-morpholinyl)-1H-benzimidazole-4-carboxylic acid,
1-[(2,3-dichlorophenyl)methyl]-2-methyl-6-(4-morpholinyl)-4-(1H-pyrazol-5-yl)-1H-benzimidazole,
2-methyl-6-(4-morpholinyl)-1-(1-naphthalenylmethyl)-4-(1H-1,2,4-triazol-3-yl)-1H-benzimidazole,
methyl 2-methyl-6-(4-morpholinyl)-1-(1-naphthalenylmethyl)-1H-benzimidazole-4-carboxylate,
1-[2,3-dichlorophenyl)methyl]-2-methyl-6-(4-morpholinyl)-1H-benzimidazole-4-carboxamide, methyl 1-[(2-fluoro-3-methylphenyl)methyl]-2-methyl-6-(4-morpholinyl)-1H-benzimidazole-4-carboxylate,
2-methyl-6-(4-morpholinyl)-1-(1-naphthalenylmethyl)-1H-benzimidazole-4-carbonitrile,
1-[2,3-dichlorophenyl)methyl]-2-methyl-6-(4-morpholinyl)-1H-benzimidazole-4-carbonitrile,
methyl 2-methyl-1-{[2-methyl-3-(trifluoromethyl)phenyl]methyl}-6-(4-morpholinyl)-1H-benzimidazole-4-carboxylate,
2-methyl-1-{[2-methyl-3-(trifluoromethyl)phenyl]methyl}-6-(4-morpholinyl)-1H-benzimidazole-4-carboxylic acid,
1-[(2-fluoro-3-methylphenyl)methyl]-2-methyl-6-(4-morpholinyl)-1H-benzimidazole-4-carboxylic acid,
2-methyl-6-(4-morpholinyl)-1-(1-naphthalenylmethyl)-1H-benzimidazole-4-carboxamide,
1-[2,3-dichlorophenyl)methyl]-2-methyl-6-(4-morpholinyl)-4-(1H-1,2,4-triazol-3-yl)-1H-benzimidazole,
methyl 2-methyl-6-(4-morpholinyl)-1-(5-quinolinylmethyl)-1H-benzimidazole-4-carboxylate,
2-methyl-6-(4-morpholinyl)-1-(5-quinolinylmethyl)-1H-benzimidazole-4-carboxylic acid,
1-[3,4-dimethylphenyl)methyl]-2-methyl-6-(4-morpholinyl)-1H-benzimidazole-4-carboxylic acid,
2-methyl-6-(4-morpholinyl)-1-(2-naphthalenylmethyl)-1H-benzimidazole-4-carboxylic acid,
1-[(3,4-dichlorophenyl)methyl]-2-methyl-6-(4-morpholinyl)-1H-benzimidazole-4-carboxylic acid,
2-methyl-1-{[2-methyl-3-(trifluoromethyl)phenyl]methyl}-6-(4-morpholinyl)-4-(1H-1,2,4-triazol-3-yl)-1H-benzimidazole,
2-methyl-4-(3-methyl-1H-1,2,4-triazol-5-yl)-6-(4-morpholinyl)-1-(1-naphthalenylmethyl)-1H-benzimidazole,
1-[2-methyl-6-(4-morpholinyl)-1-(1-naphthalenylmethyl)-1H-benzimidazol-4-yl]ethanone,
[2-methyl-6-(4-morpholinyl)-1-(1-naphthalenylmethyl)-1H-benzimidazol-4-yl]methanol,
2-methyl-N-(methylsulfonyl)-6-(4-morpholinyl)-1-(1-naphthalenylmethyl)-1H-benzimidazole-4-carboxamide,
methyl 5-(4-morpholinyl)-2-(trifluoromethyl)-1H-benzimidazole-7-carboxylate,
methyl 1-{[2-methyl-3-(trifluoromethyl)phenyl]methyl}-6-(4-morpholinyl)-2-(trifluoromethyl)-1H-benzimidazole-4-carboxylate,
1-{[2-methyl-3-(trifluoromethyl)phenyl]methyl}-6-(4-morpholinyl)-2-(trifluoromethyl)-1H-benzimidazole-4-carboxylic acid,
6-(4-morpholinyl)-1-(1-naphthalenylmethyl)-2-(trifluoromethyl)-1H-benzimidazole-4-carboxylic acid,
methyl 1-[(3-chloro-2-methylphenyl)methyl]-6-(4-morpholinyl)-2-(trifluoromethyl)-1H-benzimidazole-4-carboxylate,
1-[2,3-dichlorophenyl)methyl]-6-(4-morpholinyl)-2-(trifluoromethyl)-1H-benzimidazole-4-carboxylic acid,
1-{[2-methyl-3-(trifluoromethyl)phenyl]methyl}-6-(4-morpholinyl)-2-(trifluoromethyl)-1H-benzimidazole-4-carboxamide,
methyl 6-(4-morpholinyl)-1-(1-naphthalenylmethyl)-2-(trifluoromethyl)-1H-benzimidazole-4-carboxylate,
methyl 1-[(2,3-dichlorophenyl)methyl]-6-(4-morpholinyl)-2-(trifluoromethyl)-1H-benzimidazole-4-carboxylate,
1-{[2-methyl-3-(trifluoromethyl)phenyl]methyl}-6-(4-morpholinyl)-4-(1H-1,2,4-triazol-3-yl)-2-(trifluoromethyl)-1H-benzimidazole,
1-[(3-chloro-2-methylphenyl)methyl]-6-(4-morpholinyl)-2-(trifluoromethyl)-1H-benzimidazole-4-carboxylic acid,
1-[2,3-dichlorophenyl)methyl]-6-(4-morpholinyl)-4-(1H-1,2,4-triazol-3-yl)-2-(trifluoromethyl)-1H-benzimidazole,
1-[(3-chloro-2-methylphenyl)methyl]-6-(4-morpholinyl)-4-(1H-1,2,4-triazol-3-yl)-2-(trifluoromethyl)-1H-benzimidazole,
2-methyl-6-(4-morpholinyl)-1-(1-naphthalenylmethyl)-4-(1H-tetrazol-5-yl)-1H-benzimidazole,
[2-methyl-1-{[2-methyl-3-(trifluoromethyl)phenyl]methyl}-6-(4-morpholinyl)-1H-benzimidazol-4-yl]methanol,
1-[(3-chloro-2-methylphenyl)methyl]-2-methyl-6-(4-morpholinyl)-1H-benzimidazole-4-carboxylic acid,
2-methyl-1-[(2-methylphenyl)methyl]-6-(4-morpholinyl)-1H-benzimidazole-4-carboxylic acid,
ethyl 2-methyl-1-{[2-methyl-3-(trifluoromethyl)phenyl]methyl}-6-(4-morpholinyl)-1H-benzimidazole-4-carboxylate,
4-bromo-2-methyl-6-(4-morpholinyl)-1H-benzimidazole,
4-bromo-2-methyl-1-{[2-methyl-3-(trifluoromethyl)phenyl]methyl}-6-(4-morpholinyl)-1H-benzimidazole,
2-methyl-1-{[2-methyl-3-(trifluoromethyl)phenyl]methyl}-6-(4-morpholinyl)-4-(1,3-oxazol-2-yl)-1H-benzimidazole,
methyl 2-chloro-5-(4-morpholinyl)-1H-benzimidazole-7-carboxylate,
methyl 2-chloro-1-{[2-methyl-3-(trifluoromethyl)phenyl]methyl}-6-(4-morpholinyl)-1H-benzimidazole-4-carboxylate,
2-chloro-1-{[2-methyl-3-(trifluoromethyl)phenyl]methyl}-6-(4-morpholinyl)-1H-benzimidazole-4-carboxylic acid
methyl 2-(difluoromethyl)-5-(4-morpholinyl)-1H-benzimidazole-7-carboxylate,
2-(difluoromethyl)-6-(4-morpholinyl)-1-(1-naphthalenylmethyl)-1H-benzimidazole-4-carboxylic acid,
2-(difluoromethyl)-1-{[2-methyl-3-(trifluoromethyl)phenyl]methyl}-6-(4-morpholinyl)-1H-benzimidazole-4-carboxylic acid,
1-[2,3-dichlorophenyl)methyl]-2-(difluoromethyl)-6-(4-morpholinyl)-1H-benzimidazole-4-carboxylic acid,
1-[3-chloro-2-methylphenyl)methyl]-2-(difluoromethyl)-6-(4-morpholinyl)-1H-benzimidazole-4-carboxylic acid,
1-(1-benzothien-7-ylmethyl)-2-methyl-6-(4-morpholinyl)-1H-benzimidazole-4-carboxylic acid,
1-[2,3-dimethylphenyl)methyl]-2-methyl-6-(4-morpholinyl)-1H-benzimidazole-4-carboxylic acid,
1-[3-fluoro-2-methylphenyl)methyl]-2-methyl-6-(4-morpholinyl)-1H-benzimidazole-4-carboxylic acid,
2,4-dimethyl-1-{[2-methyl-3-(trifluoromethyl)phenyl]methyl}-6-(4-morpholinyl)-1H-benzimidazole,
1-[1-(3-chloro-2-methylphenyl)ethyl]-2-methyl-6-(4-morpholinyl)-1H-benzimidazole-4-carboxylic acid,
2-methyl-1-{[2-methyl-3-(trifluoromethyl)phenyl]methyl}-6-(4-morpholinyl)-4-(1,3-thiazol-2-yl)-1H-benzimidazole,
4-(2-furanyl)-2-methyl-1-{[2-methyl-3-(trifluoromethyl)phenyl]methyl}-6-(4-morpholinyl)-1H-benzimidazole and
2-methyl-4-[(methyloxy)methyl]-1-{[2-methyl-3-(trifluoromethyl)phenyl]methyl}-6-(4-morpholinyl)-1H-benzimidazole.

DEFINITIONS

By the term "aryl" as used herein, unless otherwise defined, is meant aromatic, hydrocarbon, ring system. The ring system may be monocyclic or fused polycyclic (e.g. bicyclic, tricyclic, etc.). In various embodiments, the monocyclic aryl ring is C5-C10, or C5-C7, or C5-C6, where these carbon numbers refer to the number of carbon atoms that form the ring system. A C6 ring system, i.e. a phenyl ring is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group.

By the term "heteroaryl" as used herein, unless otherwise defined, is meant an aromatic ring system containing carbon(s) and at least one heteroatom. Heteroaryl may be monocyclic or polycyclic. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include: benzofuran, benzothiene, benzothiophene, furan, imidazole, indole, isothiazole, oxazole, pyrazine, pyrazole, pyridazine, pyridine, pyrimidine, pyrrole, quinoline, isoquinoline, quinazoline, quinoxaline, thiazole, and thiophene. According to an alternative embodiment, heteroaryls may be substituted with one to three alkyl groups.

By the term "alkoxy" as used herein is meant —O(alkyl) including —OCH$_3$, —OCH$_2$CH$_3$ and —OC(CH$_3$)$_3$ where alkyl is as described herein.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—(CH$_2$)$_n$", "—(CH$_2$)$_m$" and the like, is meant a linear or branched, saturated or unsaturated hydrocarbon chain, and unless otherwise defined, the carbon chain will contain from 1 to 12 carbon atoms.

By the term "co-administering" and derivatives thereof as used herein is meant either simultaneous administration or any manner of separate sequential administration of a PI3 kinase inhibiting compound, as described herein, and a further active ingredient or ingredients. The term further active ingredient or ingredients, as used herein, includes any compound or therapeutic agent known to or that demonstrates advantageous properties when administered to a patient in need of treatment. Suitably, if the administration is not simultaneous, the compounds are administered in a close time proximity to each other. Furthermore, it does not matter if the compounds are administered in the same dosage form, e.g. one compound may be administered topically and another compound may be administered orally.

The term "compound" as used herein includes all isomers of the compound. Examples of such isomers include: enantiomers, tautomers, rotamers.

In formulas where a "dotted" bond is drawn between two atoms, it is meant that such bond can be either single or double bond. A ring system containing such bonds can be aromatic or non-aromatic.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by Formula (I) above as well as any wholly or partially equilibrated mixtures thereof. The present invention also covers the individual isomers of the compounds represented by the formulas above as mixtures with isomers thereof in which one or more chiral centers are inverted. The present invention also includes isotopomers of the compounds of Formula (I). Examples of such isotopomers include but not limited to compounds with one of more deuterium atoms.

Compounds of Formula (I) are included in the pharmaceutical compositions of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

It will be appreciated by those skilled in the art that the compounds of formula (I) may be utilized as a pharmaceutically acceptable salt version thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanol amine, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate (methanesulfonate), methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate (methylbenzenesulfonate), triethiodide, trimethylammonium and valerate. Other salts, such as oxalic and trifluoroacetic, which are not themselves pharmaceutically acceptable, may be useful in the preparation of salts useful as intermediates in obtaining compounds of this invention and these form a further aspect of the invention. In one embodiment, the compound of formula (I) is in the form of the free base. In one embodiment, the compound of formula (I) is in the form of the tris salt, i.e. tris (hydroxymethyl)aminomethane. In one embodiment, the compound of formula (I) is in the form of the sulfate salt. In one embodiment, the compound of formula (I) is in the form of the hydrochloride salt. In one embodiment, the compound of formula (I) is in the form of the sodium salt. Certain salt versions of the compounds may be solvates, particularly hydrates. In one embodiment, the compound of formula (I) or a pharmaceutically acceptable salt thereof is in the form of a mono-, di-, tri- or hemi-hydrate.

It has now been found that compounds of the present invention are inhibitors of the Phosphatoinositides 3-kinases (PI3Ks). When the phosphatoinositides 3-kinase (PI3K) enzyme is inhibited by a compound of the present invention, PI3K is unable to exert its enzymatic, biological and/or pharmacological effects. The compounds of the present invention are therefore useful in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

Compounds according to Formula (I) are suitable for the modulation, notably the inhibition of the activity of phosphatoinositides 3-kinases (PI3K) and, more particularly, selective inhibitors of the beta isoform of phosphatoinositides 3-kinase (PI3Kβ). Therefore the compounds of the present invention are also useful for the treatment of disorders which are mediated by PI3Ks. Said treatment involves the modulation—notably the inhibition or the down regulation—of the phosphatoinositides 3-kinases.

Because the pharmaceutically active compounds of the present invention are active as PI3 kinase inhibitors, particularly the compounds that inhibit PI3Kβ, either selectively or in conjunction with one or more of PI3δ, PI3Kα, and/or PI3Kγ, they exhibit therapeutic utility in treatment of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

As used herein, the term "treatment" or "treating" in the context of therapeutic methods, refers to alleviating the specified condition, eliminating or reducing the symptoms of the condition, slowing or eliminating the progression, invasion, or metastatic spread of the condition and preventing or delaying the reoccurrence of the condition in a previously afflicted subject. The present invention further provides use of the compounds of the invention for the preparation of a medicament for the treatment of several conditions in a mammal (e.g., human) in need thereof.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which are exhibit mutation of PTEN, or mutation of an upstream activator of PI3Kβ kinase or overexpression of an upstream activator of PI3Kβ kinase, and are therefore susceptible to treatment with an PI3Kβ inhibitor are known in the art, and include both primary and metastatic tumors and cancers. According to one embodiment, description of the treatment of a susceptible neoplasm may be used interchangeably with description of the treatment of a cancer.

According to one embodiment, "susceptible neoplasms" includes, but are not limited to PTEN-deficient neoplasms listed as follows:
brain (gliomas),
glioblastomas,
leukemias,
Bannayan-Zonana syndrome,
Cowden disease,
Lhermitte-Duclos disease,
breast cancer,
inflammatory breast cancer,
colorectal cancer
Wilm's tumor,
Ewing's sarcoma,
Rhabdomyosarcoma,
ependymoma,
medulloblastoma,
colon cancer,
head and neck cancer,
kidney cancer,
lung cancer,
liver cancer,
melanoma,
squamous cell carcinoma,
ovarian cancer,
pancreatic cancer,
prostate cancer,
sarcoma cancer,
osteosarcoma,
giant cell tumor of bone,
thyroid cancer,
lymphoblastic T cell leukemia,
chronic myelogenous leukemia,
chronic lymphocytic leukemia,
hairy-cell leukemia,
acute lymphoblastic leukemia,
acute myelogenous leukemia,
chronic neutrophilic leukemia,
acute lymphoblastic T cell leukemia,
Plasmacytoma,
Immunoblastic large cell leukemia,
Mantle cell leukemia,
Multiple myeloma,
Megakaryoblastic leukemia,
multiple myeloma,
Acute megakaryocytic leukemia,
promyelocytic leukemia,
Erythroleukemia,
malignant lymphoma,
hodgkins lymphoma,
non-hodgkins lymphoma,
lymphoblastic T cell lymphoma,
Burkitt's lymphoma,
follicular lymphoma,
neuroblastoma,
bladder cancer,
urothelial cancer,
vulval cancer,
cervical cancer,
endometrial cancer,
renal cancer,
mesothelioma,
esophageal cancer,
salivary gland cancer,
hepatocellular cancer,
gastric cancer,
nasopharangeal cancer,
buccal cancer,
cancer of the mouth,
GIST (gastrointestinal stromal tumor),
and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including trip-negative breast cancer, and glioma. PTEN deficiency has been correlated to such cancers as demonstrated in a number of published resources, e.g. Am J Clin Pathol. 2009 February; 131(2):257-63 (glioblastoma), J Clin Neurosci. 2010 December; 17(12): 1543-7 (glioblastoma), Nat. Genet. 2009 May; 41(5):619-24 (prostate cancer), Br J Cancer. 2008 Oct. 21; 99(8):1296-301 (prostate cancer), Int J Cancer. 2007 Mar. 15; 120(6):1284-92 (prostate cancer), J Invest Dermatol. 2006 January; 126(1):154-60 (melanoma), J Clin Oncol. 2006 Jan. 10; 24(2):288-95 (melanoma), Am J Clin Pathol. 2005 October; 124(4):528-36 (melanoma), Int J Oncol. 2009 April; 34(4):983-93 (breast cancer), Epigenetics. 2011 May 1; 6(5):638-49 (breast cancer), Gynecol Oncol. 2009 February; 112(2):307-13 (ovarian cancer), Mod Pathol. 2010 October; 23(10):1316-24 (ovarian cancer), J Pathol.

2010 February; 220(3):392-400 (ovarian cancer), Lung. 2009 March-April; 187(2):104-9 (lung cancer), Anticancer Res. 2007 January-February; 27(1B):575-81 (lung cancer), Am J. Surg. 2008 June; 195(6):719-25 (colon cancer), J Clin Oncol. 2009 Dec. 10; 27(35):5924-30 (colon cancer), Gynecol Oncol. 2004 June; 93(3):621-7 (cervical cancer), and J Oral Pathol Med. 2002 August; 31(7):379-84 (head and neck cancer).

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating fibrosis in a mammal in need thereof, comprising administering to the mammal a therapeutically effective amount of a compound of formula (I) (including any particular sub-generic formula described herein) or a pharmaceutically acceptable salt thereof. Fibrosis includes, alternatively or collectively, systemic sclerosis (SSc), arthritis, nephropahty, and liver cirrhosis.

In another aspect of the present invention, there is provided a method of treating hormone refractory prostate cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating non-small-cell lung cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating endometrial cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating gastric cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating melanoma in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating head and neck cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating trip-negative breast cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating glioma in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm in a mammal in need thereof.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm in a mammal in need thereof.

In another aspect of the present invention, there is provided a pharmaceutical composition comprising a compound of formula (I) (including any particular sub-generic formula described herein) or a pharmaceutically acceptable salt thereof for use in the treatment of a susceptible neoplasm in a mammal in need thereof.

When a compound of Formula (I) is administered for the treatment of cancer, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present PI3 kinase inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl. Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)-N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-respectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

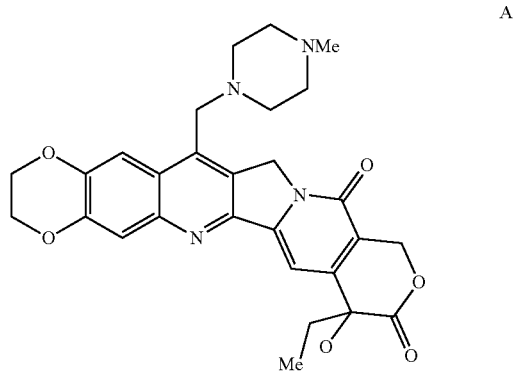 [SMILES: CCC1(O)C(=O)OCc2c1cc1n(c2=O)Cc2c-1nc1cc3c(cc1c2CN1CCN(C)CC1)OCCO3]

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChem. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention Inhibitors of angiogenesis related VEGFR and TIE2 are discussed above in regard to signal transduction inhibitors (both receptors are receptor tyrosine kinases). Accordingly, non-receptor tyrosine kinase inhibitors may be used in combination with the inhibitors of the present invention. For example, anti-VEGF antibodies, which do not recognize VEGFR (the receptor tyrosine kinase), but bind to the ligand; small molecule inhibitors of integrin (alpha beta$_3$) that will inhibit angiogenesis; endostatin and angiostatin (non-RTK) may also prove useful in combination with the disclosed family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt, hydrate, solvate or pro-drug thereof and at least one antineoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a PI3K inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. According to one embodiment, the oral dosage for human administration contains 100 to 1000 mg per day. Oral administration, which uses lower dosages is preferred. Parenteral administration, at high dosages, however, also can be used when safe and convenient for the patient.

Optimal dosages to be administered may be readily determined by those skilled in the art, and will vary with the particular PI3 kinase inhibitor in use, the strength of the preparation, the mode of administration, and the advancement of the disease condition. Additional factors depending on the particular patient being treated will result in a need to adjust dosages, including patient age, weight, diet, and time of administration. Exemplary dosages include oral formulations equivalent to 10 mg, 25 mg, and 100 mg of the compound of formula (I), to be administered alone, in multiples, or in combination. Another exemplary dosage includes oral formulations of the tris(hydroxymethyl)aminomethane salt of 2-methyl-1-{[2-methyl-3-(trifluoromethyl)phenyl]methyl}-6-(4-morpholinyl)-1H-benzimidazole-4-carboxylic acid equivalent to 10 mg, 25 mg, or 100 mg of the free base of 2-methyl-1-{[2-methyl-3-(trifluoromethyl)phenyl]methyl}-6-(4-morpholinyl)-1H-benzimidazole-4-carboxylic acid.

The method of this invention of inducing PI3 kinase inhibitory activity in mammals, including humans, comprises administering to a subject in need of such activity an effective PI3 kinase modulating/inhibiting amount of a pharmaceutically active compound of the present invention.

The invention also provides for the use of a compound of Formula (I) in the manufacture of a medicament for use as a PI3 kinase inhibitor.

The invention also provides for the use of a compound of Formula (I) in the manufacture of a medicament for use in therapy.

The invention also provides for the use of a compound of Formula (I) in the manufacture of a medicament for use in treating autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The invention also provides for a pharmaceutical composition for use as a PI3 inhibitor which comprises a compound of Formula (I) and a pharmaceutically acceptable carrier.

The invention also provides for a pharmaceutical composition for use in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, which comprises a compound of Formula (I) and a pharmaceutically acceptable carrier.

In addition, the pharmaceutically active compounds of the present invention can be co-administered with further active ingredients, including compounds known to have utility when used in combination with a PI3 kinase inhibitor.

Without further elaboration, it is believed that one skilled in the art can, using the preceding description, utilize the present invention to its fullest extent. The following examples are, therefore, to be construed as merely illustrative and not a limitation of the scope of the present invention in any way.

EXPERIMENTAL PROCEDURES

Compounds of Formula (I) may be prepared using the general schemes I-VII, as described below.

Scheme I (R2=Me)

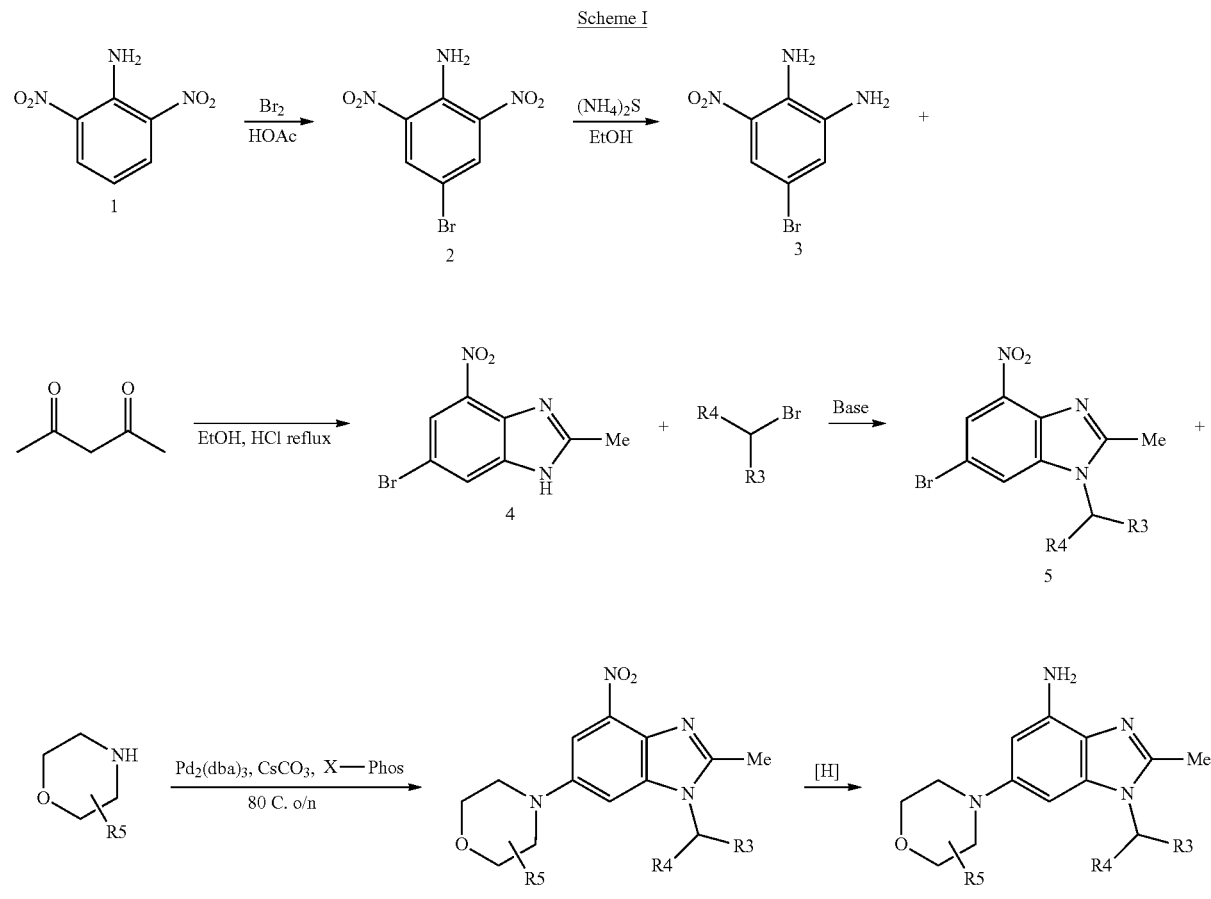

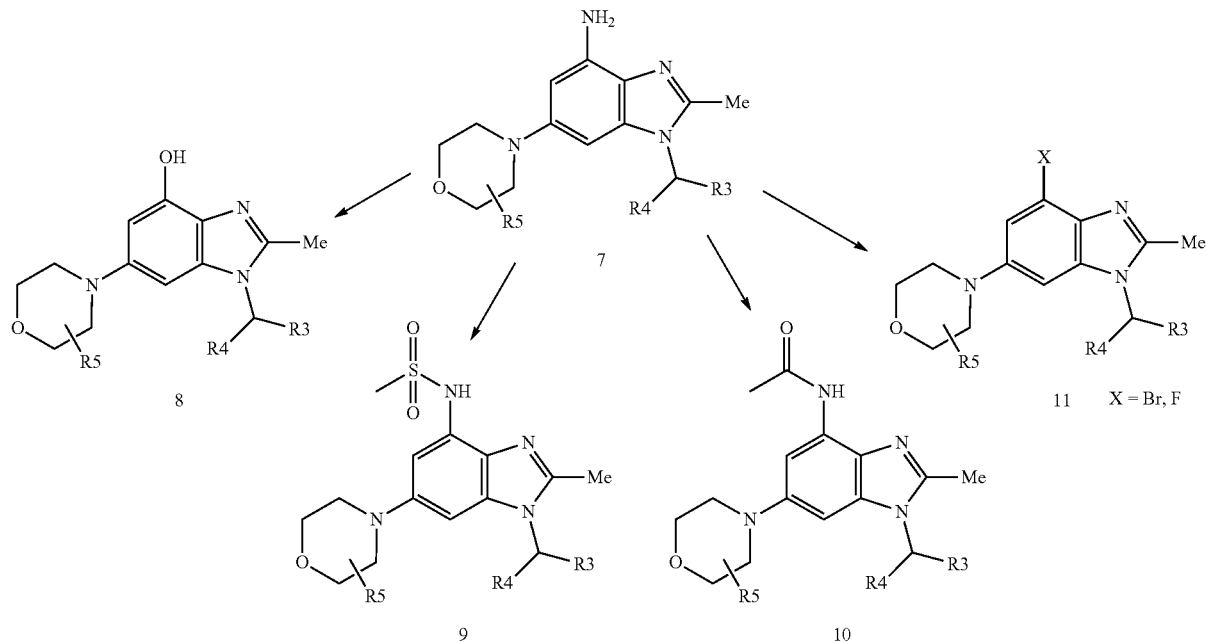

(R2 = Me)

2,6-dinitro aniline 1 can be brominated with bromine in acetic acid to provide 4-bromo-2,6-dinitroaniline 2 that can be reduced to the di-amino nitro benzene 3 with $(NH_4^+)_2S$. Subsequent reaction of 3 with 2,4-pentanedione in the presence of strong acid at reflux temperatures, in an alcoholic solvent, affords nitrobenzimidazole 4. Alkylation to afford substituted benzimidazole 5 can be accomplished with a suitably substituted alkyl halide with a base, such as $K_2CO_3$, in a polar aprotic solvent, such as DMF. Palladium-catalyzed displacement of the aromatic bromine with morpholine can then afford substituted nitrobenzimidazole 6 which can then be reduced to the amino benzimidazole 7. Amino benzimidazole 7 can then be converted into hydroxyl analog 8, sulfonamide 9, amide 10, and halo analog 11, using standard organic manipulations.

Scheme II

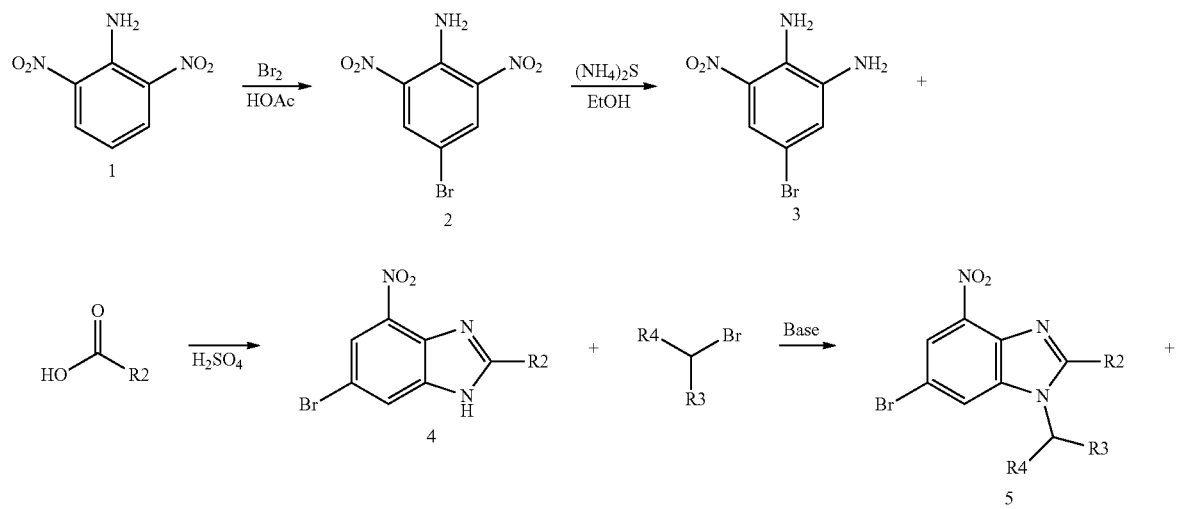

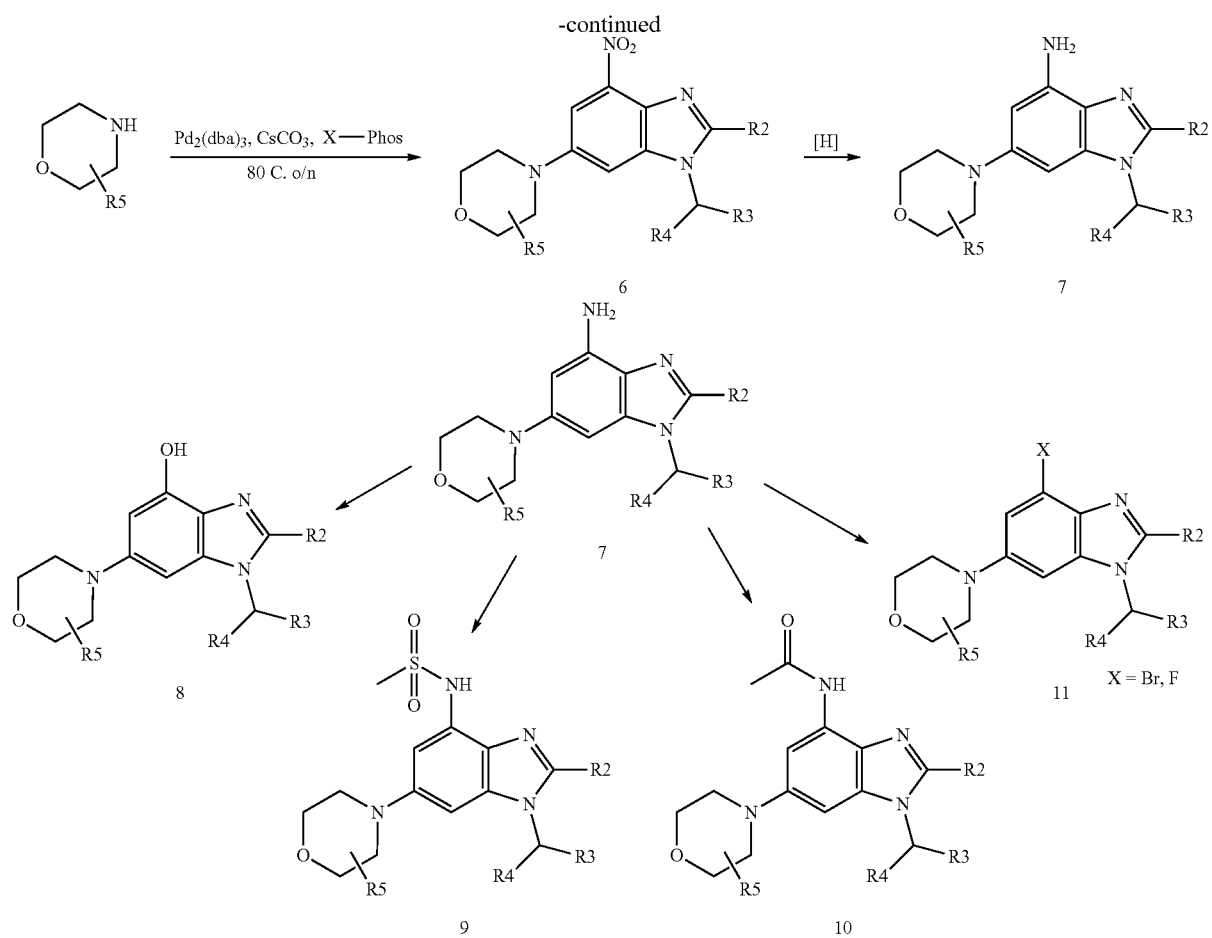

2,6-dinitro aniline 1 can be brominated with bromine in acetic acid to provide 4-bromo-2,6-dinitroaniline 2 that can be reduced to the di-amino nitro benzene 3 with $(NH_4^+)_2S$. Subsequent reaction of 3 with a carboxylic acid in the presence of strong acid at elevated temperatures affords nitrobenzimidazole 4. Alkylation to afford substituted benzimidazole 5 can be accomplished with a suitably substituted alkyl halide with a base, such as $K_2CO_3$, in a polar aprotic solvent, such as DMF. Palladium-catalyzed displacement of the aromatic bromine with morpholine can then afford substituted nitrobenzimidazole 6 which can then be reduced to the amino benzimidazole 7. Amino benzimidazole 7 can then be converted into hydroxyl analog 8, sulfonamide 9, amide 10, and halo analog 11, using standard organic manipulations.

Scheme III

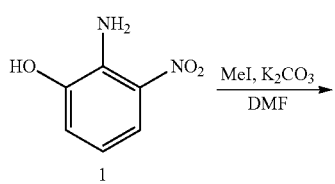

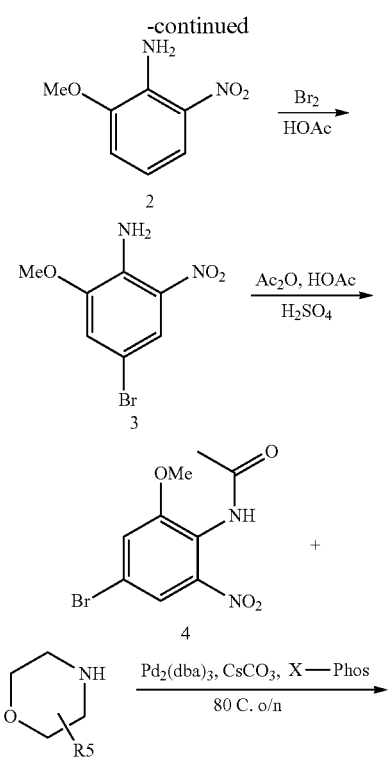

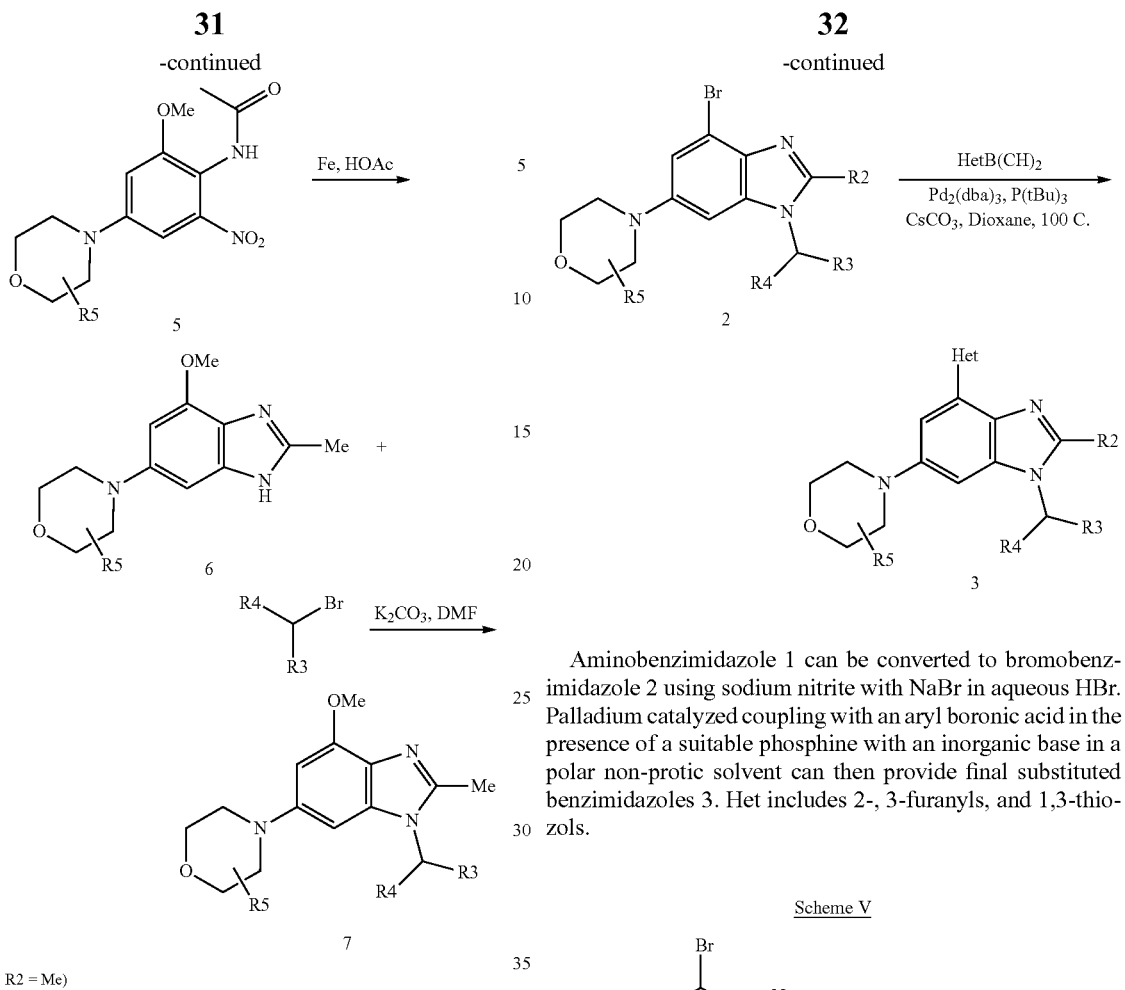

2-amino-3-nitrophenol 1 can be methylated with MeI and K₂CO₃ in DMF to afford methoxy nitro aniline 2. Bromination, with bromine in acetic acid, followed by acetylation with acetic anhydride in acetic acid and sulfuric acid, can provide intermediate 4. Palladium-catalyzed displacement of the aromatic bromide with morpholine can then afford intermediate 5. Iron-induced nitro reduction followed by ring closure can then provide benzimidazole 6 that can be alkylated with a suitably substituted alkyl bromide using a base, such as K₂CO₃, in a polar aprotic solvent such as DMF, to afford final products 7.

Aminobenzimidazole 1 can be converted to bromobenzimidazole 2 using sodium nitrite with NaBr in aqueous HBr. Palladium catalyzed coupling with an aryl boronic acid in the presence of a suitable phosphine with an inorganic base in a polar non-protic solvent can then provide final substituted benzimidazoles 3. Het includes 2-, 3-furanyls, and 1,3-thiozols.

Scheme V

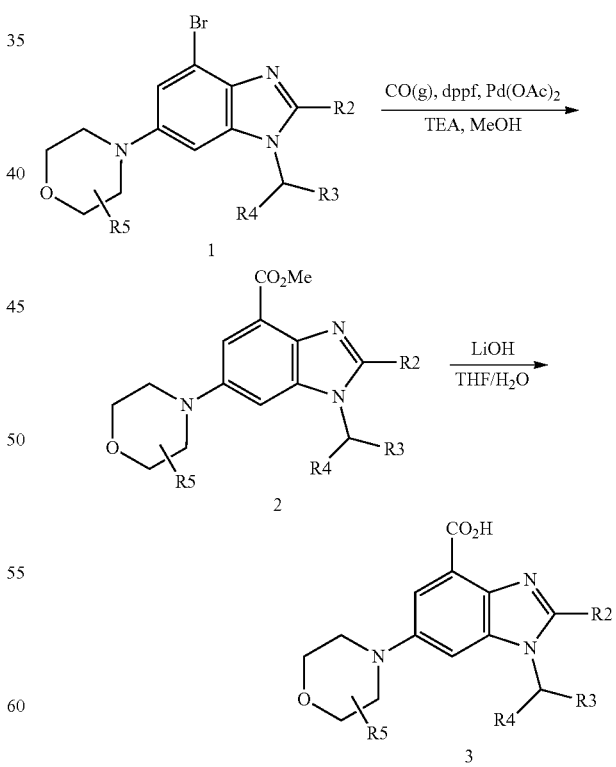

Palladium catalyzed carbonylaton of bromo-benzimidazole 1 can be accomplished by bubbling carbon-monoxide gas in methanol with triethylamine to provide methyl ester 2.

Scheme IV

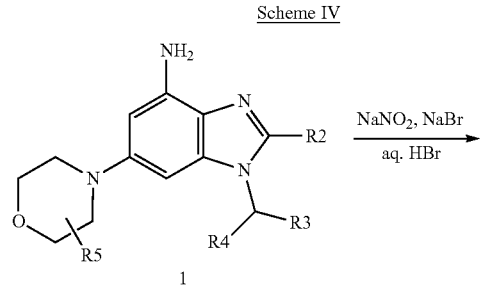

Ester hydrolysis can then be accomplished with lithium hydroxide in THF/water to provide final product benzimidazole acid 3.

DMA can provide intermediate 4 that can then be cyclized to triazole analogs 5 with hydrazine in acetic acid.

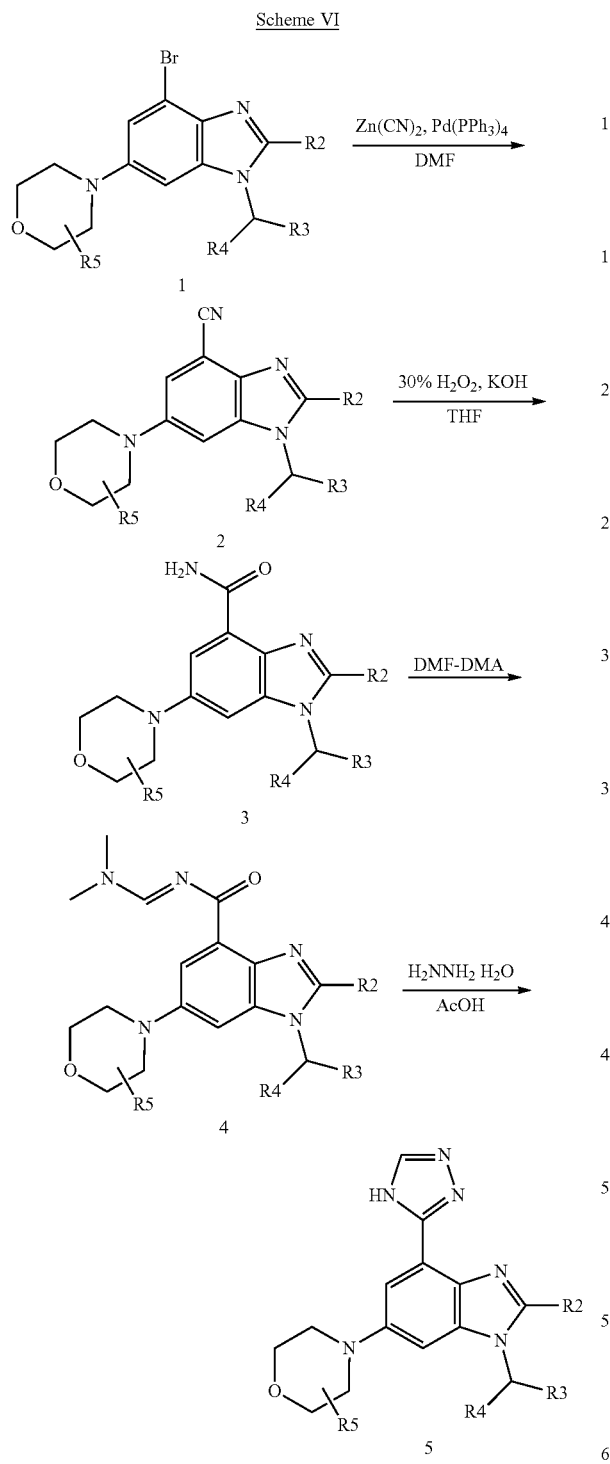

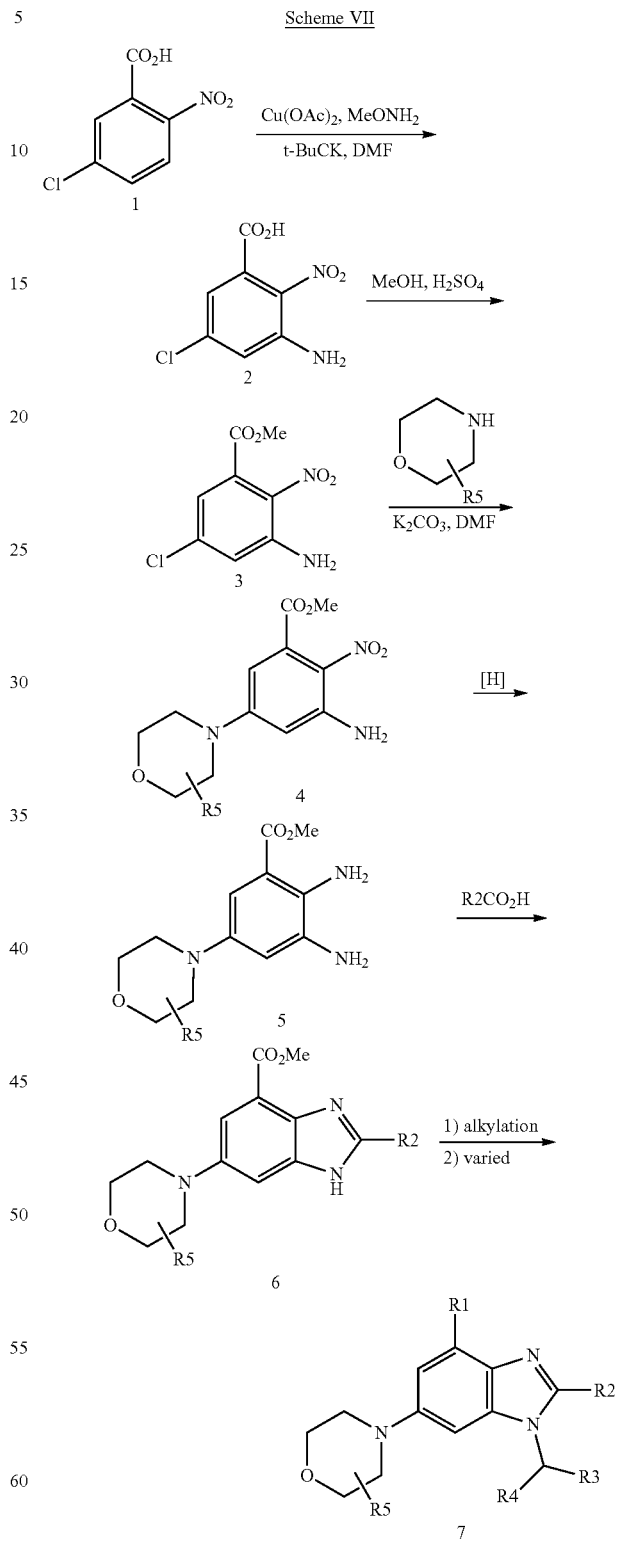

Palladium catalyzed cyanation of bromo-benzimidazole 1 can be accomplished with zinc cyanide in DMF to provide benzimidazole nitrile 2. The nitrile can be converted to the primary carboxamide with KOH and peroxide in THF to provide amide 3. Treatment of the carboxamide 3 with DMF- Amination of 5-chloro-2-nitrobenzoic acid with O-methyl hydroxylamine and t-butoxide in the presence of copper acetate can provide 3-amino-5-chloro-2-nitrobenzoic acid 2.

Esterification can be accomplished with methanol and sulfuric acid to provide methyl ester 3 that can be reacted with morpholine in DMF with $K_2CO_3$ to provide phenyl morpholine analog 4. Nitro reduction can be accomplished using a variety of metal reductions to provide diamine 5. Condensation of 5 with a variety of carboxylic acids can provide benzimidazole methylester 6 that can be further converted to final products 7 (R1=$CO_2$Me, $CO_2$H, $CONH_2$, CN, triazole, tetrazole) after alkylation with an alkyl halide, followed by standard organic manipulations as previously described.

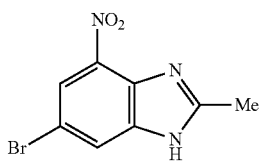 [SMILES: Cc1nc2c([N+](=O)[O-])cc(Br)cc2[nH]1]

Preparation of
5-bromo-2-methyl-7-nitro-1H-benzimidazole a) 4-bromo-2,6-dinitrobenzenamine

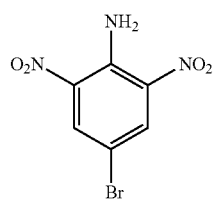 [SMILES: Nc1c([N+](=O)[O-])cc(Br)cc1[N+](=O)[O-]]

A stirred suspension of 2,6-dinitroaniline (5 g, 27.3 mmol) in glacial acetic acid (50 mL) was added bromine (1.5 mL, 30 mmol) dropwise and heated at 120° C. for 2 h. After cooling to ambient temperature, the resultant mixture was poured into water (50 mL). The precipitate solid was collected by filtration and washed with water then dried in-vacuo. The solid was re-dissolved in EtOAC, washed with water and saturated brine. The organic layer was collected and concentrated in-vacuo to give the desired product (6.88 g, 95%). $^1$H NMR (300 MHz, DMSO-$d_6$) δ ppm 8.37 (br s, 2H), 8.58 (s, 2H).

b) 5-bromo-3-nitrobenzene-1,2-diamine

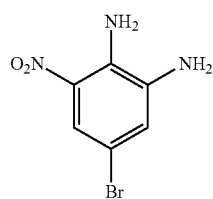 [SMILES: Nc1cc(Br)cc([N+](=O)[O-])c1N]

4-bromo-2,6-dinitrobenzenamine was dissolved in EtOH (50 mL) and $(NH_4)_2S$ (2.2 mL) was added to the mixture. The reaction mixture was heated to 90° C. for 1 h. TLC showed a new compound and some remaining starting material remained. Additionally, another batch $(NH_4)_2S$ (2.5 mL) was added. After 1 h, TLC analysis showed little starting material remained. The reaction mixture was concentrated to give a deep red solid. It was then purified by silica gel chromatography eluted with DCM to afford the desired product as a red solid (578 mg, 50%). $^1$H NMR (300 MHz, $CDCl_3$) δ ppm 3.50 (br s, 2H), 5.93 (br s, 2H), 7.04 (d, 1H, J=1.8 Hz), 7.87 (d, 1H, J=1.8 Hz); LC-MS: m/e=232 [M+1]$^+$.

c) 6-bromo-2-methyl-4-nitro-1H-benzo[d]imidazole

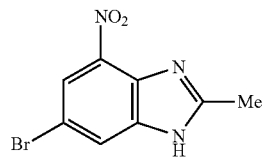

A mixture of 5-bromo-3-nitrobenzene-1,2-diamine (464 mg) and pentane-2,4-dione (400 mg) in EtOH (27 mL) and 5 N HCl (7.4 mL) was refluxed for 3 h. The mixture was cooled to room temperature and the solvent was removed in-vacuo. The residue was dissolved in EtOAc and washed with aqueous $NaHCO_3$ solution and brine. The organic layer was concentrated to afford the desired product as a solid (460 mg, 90%). $^1$H NMR (300 MHz, $CDCl_3$) δ ppm 2.73 (s, 3H), 8.11 (d, 1H, J=1.8 Hz), 8.24 (d, 1H, J=1.8 Hz), 10.20 (s, 1H, s); LC-MS: m/e=256 [M+1]$^+$

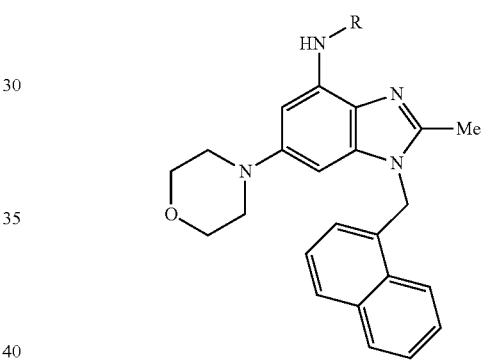

Preparation of 2-methyl-6-(4-morpholinyl)-1-(1-naphthalenylmethyl)-1H-benzimidazol-4-amine and N-(2-Methyl-6-morpholin-4-yl-1-naphthalen-1-ylmethyl-1H-benzoimidazol-4-yl)-acetamide a) 6-bromo-2-methyl-1-(naphthalen-1-ylmethyl)-4-nitro-1H-benzo[d]imidazole

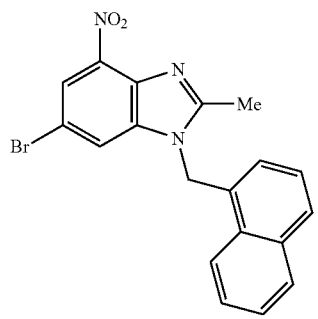 [SMILES: Cc1nc2c([N+](=O)[O-])cc(Br)cc2n1Cc1cccc2ccccc12]

A mixture of 6-bromo-2-methyl-4-nitro-1H-benzo[d]imidazole (prepared following the same procedure as Example 1) (3 g), 1-(bromomethyl)naphthalene (2.85 g) and $K_2CO_3$ (3.23 g) in DMF (100 mL) was stirred at 80° C. overnight. It was cooled to room temperature and filtered. The filtrate was then poured into water. It was then filtered to afford a solid and the solid was washed with water and then dried in-vacuo to afford the desired product (4.63 g, 100%). $^1$H NMR (300 MHz, DMSO-d$_6$) δ ppm 2.54 (s, 3H), 6.16 (s, 2H), 6.32 (d, 1H, J=7.5 Hz), 7.33 (t, 1H, J=7.5 Hz), 7.61-7.72 (m, 2H), 7.87 (d, 1H, J=7.5 Hz), 8.01 (d, 1H, J=7.5 Hz), 8.14 (d, 1H, J=1.8 Hz), 8.19 (d, 1H, J=7.5 Hz), 8.28 (d, 1H, J=1.8 Hz); LC-MS: m/e=296 [M+1]$^+$.

b) 4-(2-methyl-3-(naphthalen-1-ylmethyl)-7-nitro-3H-benzo[d]imidazol-5-yl)morpholine

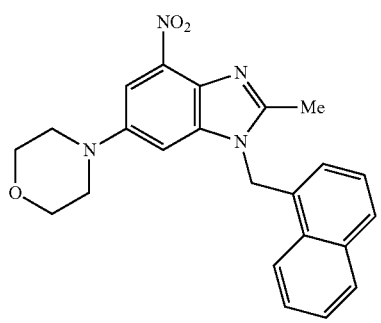 [SMILES: Cc1nc2c([N+](=O)[O-])cc(N3CCOCC3)cc2n1Cc1cccc2ccccc12]

A mixture of 6-bromo-2-methyl-1-(naphthalen-1-ylmethyl)-4-nitro-1H-benzo[d]imidazole (4.63 g), morpholine (3.05 g), Pd$_2$(dba)$_3$ (1.05 g), Cs$_2$CO$_3$ (5.72 g) and X-Phos (1.09 g) in dioxane (100 mL) was degassed with nitrogen and then stirred at 80° C. overnight. The mixture was cooled to room temperature and the solvent was removed in-vacuo. The residue was then purified by silica gel chromatography eluted with EtOAc:Petrolium ether=1:1 to afford the desired product as a yellow solid (2.8 g, 60%). $^1$H NMR (300 MHz, DMSO-d6) δ ppm 2.46 (s, 3H), 3.12 (t, 4H, J=4.8 Hz). 3.70 (t, 4H, J=4.8 Hz), 6.09 (s, 2H), 6.31 (d, 1H, J=7.5 Hz), 7.34 (t, 1H, J=7.5 Hz), 7.53 (d, 1H, J=2.1 Hz), 7.62-7.70 (m, 3H), 7.86 (d, 1H, J=8.1 Hz), 8.01 (d, 1H, J=7.5 Hz), 8.23 (d, 1H, J=8.1 Hz); LC-MS: m/e=403 [M+1]+.

c) 2-methyl-6-morpholino-1-(naphthalen-1-ylmethyl)-1H-benzo[d]imidazol-4-amine and N-(2-Methyl-6-morpholin-4-yl-1-naphthalen-1-ylmethyl-1H-benzoimidazol-4-yl)-acetamide To a refluxing mixture of 4-(2-methyl-3-(naphthalen-1-ylmethyl)-7-nitro-3H-benzo[d]imidazol-5-yl)morpholine (804 mg) in HOAc (50 mL) was added iron powder (336 mg) and the mixture was continued to reflux for 3 h. The mixture was cooled to room temperature and HOAc was removed in-vacuo. The residue was then neutralized with aqueous NaHCO$_3$ solution. It was extracted with DCM and the organic layer was washed with brine, dried over anhydrous Na$_2$SO$_4$, filtered and concentrated in-vacuo. The residue was purified by silica gel chromatography eluted with MeOH:DCM=1:30 to afford Example 2 (350 mg, 47%) and Example 3 (350 mg, 42%). Example 2 $^1$H NMR (300 MHz, DMSO-d$_6$) δ ppm 2.33 (s, 3H), 2.91 (t, 4H J=4.8 Hz), 3.64 (t, 4H J=4.8 Hz), 5.15 (br s, 2H), 5.83 (s, 2H), 6.10 (d, 1H, J=2.1 Hz), 6.12 (d, 1H, J=2.1 Hz), 6.38 (d, 1H, J=7.5 Hz), 7.34 (t, 1H, J=7.5 Hz), 7.58-7.68 (m, 2H), 7.84 (d, 1H, J=8.4 Hz), 8.01 (d, 1H, J=7.5 Hz), 8.23 (d, 1H, J=8.4 Hz); LC-MS: m/e=373 [M+1]+; Example 3 $^1$H NMR (300 MHz, DMSO-d$_6$) δ ppm 2.18 (s, 3H), 2.40 (s, 3H, s), 2.96 (t, 4H, J=4.8 Hz), 3.67 (t, 4H, J=4.8 Hz), 5.95 (s, 2H), 6.34 (d, 1H, J=7.5 Hz), 6.68 (s, 1H), 7.34 (t, 1H, J=7.5 Hz), 7.59-7.70 (m, 2H), 7.76 (s, 1H), 7.85 (d, 1H, J=7.5 Hz), 8.01 (d, 1H, J=7.5 Hz), 8.23 (d, 1H, J=7.5 Hz), 9.81 (s, 1H); LC-MS: m/e=415 [M+1]+

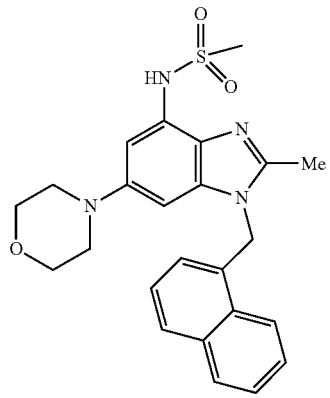 [SMILES: Cc1nc2c(NS(C)(=O)=O)cc(N3CCOCC3)cc2n1Cc1cccc2ccccc12]

Preparation of N-[2-methyl-6-(4-morpholinyl)-1-(1-naphthalenylmethyl)-1H-benzimidazol-4-yl]methanesulfonamide a) 2-methyl-6-morpholino-1-(naphthalen-1-ylmethyl)-1H-benzo[d]imidazol-4-amine

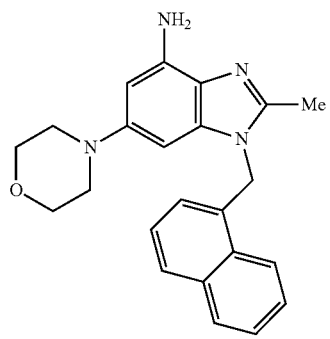

A mixture of 4-(2-methyl-3-(naphthalen-1-ylmethyl)-7-nitro-3H-benzo[d]imidazol-5-yl)morpholine (804 mg), prepared as described in Example 2, iron powder (168 mg) and FeSO$_4$ (84 mg) in ethanol (30 mL) and H$_2$O (30 mL) was stirred at reflux temperature overnight. The mixture was cooled to room temperature and the solvent was removed in-vacuo. The residue was dissolved in DCM and filtered. The filtrate was then washed with brine, dried over anhydrous Na$_2$SO$_4$, filtered and concentrated in-vacuo to afford the desired product as a solid (720 mg, 97%). $^1$H NMR (300 MHz, DMSO-d$_6$) δ ppm 2.33 (s, 3H), 2.91 (t, 4H J=4.8 Hz), 3.64 (t, 4H J=4.8 Hz), 5.15 (br s, 2H), 5.83 (s, 2H), 6.10 (d, 1H, J=2.1 Hz), 6.12 (d, 1H, J=2.1 Hz), 6.38 (d, 1H, J=7.5 Hz), 7.34 (t, 1H, J=7.5 Hz), 7.58-7.68 (m, 2H), 7.84 (d, 1H, J=8.4 Hz), 8.01 (d, 1H, J=7.5 Hz), 8.23 (d, 1H, J=8.4 Hz); LC-MS: m/e=373 [M+1]+ b) N-(2-methyl-6-morpholino-1-(naphthalen-1-ylmethyl)-1H-benzo[d]imidazol-4-yl)methanesulfonamide To a solution of 2-methyl-6-morpholino-1-(naphthalen-1-ylmethyl)-1H-benzo[d]imidazol-4-amine (186 mg), Et$_3$N (0.15 mL) and DCM (20 mL) was added a solution of methanesulfonyl chloride (69 mg) in DCM at 0° C. and then the mixture was stirred at room temperature for 1 h. The mixture was diluted with DCM and washed with brine, dried over anhydrous $Na_2SO_4$, filtered and concentrated in-vacuo. The residue was then purified by silica gel chromatography eluted with MeOH:DCM=1:30 to afford the desired product as a solid (180 mg, 80%). $^1$H NMR (300 MHz, DMSO-$d_6$) δ ppm 2.40 (s, 3H), 2.98 (t, 4H, J=4.8 Hz), 3.21 (s, 3H), 3.68 (t, 4H, J=4.8 Hz), 5.96 (s, 2H), 6.37 (d, 1H, J=8.1 Hz), 6.80 (s, 2H), 7.35 (t, 1H, J=8.1 Hz), 7.60-7.71 (m, 2H), 7.85 (d, 1H, J=8.1 Hz), 8.01 (d, 1H, J=8.1 Hz), 8.24 (d, 1H, J=8.1 Hz), 9.49 (br s, 1H); LC-MS: m/e=451 [M+1]+.

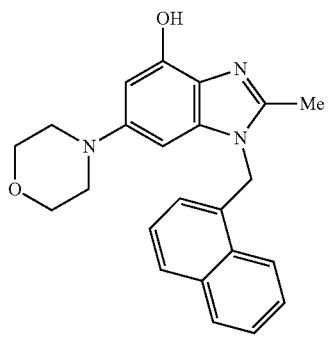 [SMILES: Cc1nc2c(O)cc(N3CCOCC3)cc2n1Cc1cccc2ccccc12]

Preparation of 2-methyl-6-(4-morpholinyl)-1-(1-naphthalenylmethyl)-1H-benzimidazol-4-ol a) 2-methyl-6-morpholino-1-(naphthalen-1-ylmethyl)-1H-benzo[d]imidazol-4-amine

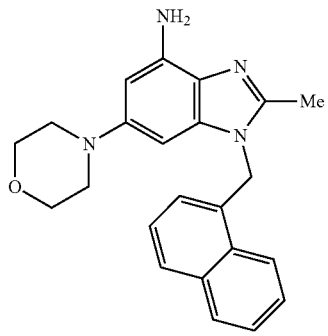

$TiCl_3$ (19.7 mL) was added to a solution of 4-(2-methyl-3-(naphthalen-1-ylmethyl)-7-nitro-3H-benzo[d]imidazol-5-yl)morpholine (1.82 g), prepared following the same procedure as in Example 4, and $NH_4OAc$ (4.85 g) in MeOH (150 mL). After stirring for 7 min at room temperature, TLC showed no starting material remaining. The pH of the mixture was made basic by adding aqueous $Na_2CO_3$ solution. The solvent was removed under reduced pressure and the residue was extracted with DCM (250 mL×2). The combined organic layers were washed with brine, dried over anhydrous $Na_2SO_4$, filtered and concentrated in-vacuo to afford the desired product as a white solid (1.52 g, 91%). $^1$H NMR (300 MHz, $CDCl_3$) δ ppm 2.47 (s, 3H), 3.02 (t, 4H, J=4.8 Hz), 3.78 (t, 4H, J=4.8 Hz), 4.30 (s, 2H), 5.68 (s, 2H), 6.05 (d, 1H, J=1.8 Hz), 6.25 (d, 1H, J=1.8 Hz), 6.56 (d, 1H, J=7.5 Hz), 7.27 (t, 1H, J=7.5 Hz), 7.55-7.66 (m, 2H), 7.77 (d, 1H, J=8.1 Hz), 7.93 (d, 1H, J=8.1 Hz), 8.05 (d, 1H, J=8.1 Hz); LC-MS: m/e=373 [M+1]+.

b) 2-methyl-6-morpholino-1-(naphthalen-1-ylmethyl)-1H-benzo[d]imidazol-4-ol

To a solution of 2-methyl-6-morpholino-1-(naphthalen-1-ylmethyl)-1H-benzo[d]imidazol-4-amine (842 mg) in $H_2O$ (20 mL), MeOH (1 mL) and conc. $H_2SO_4$ (3 mL) was added aqueous $NaNO_2$ (344 mg) solution drop-wise at 0° C. The mixture was stirred at 0° C. for 15 min and then stirred at reflux temperature for 1 h. The mixture was cooled to room temperature and the pH neutralized with aqueous $NaHCO_3$ solution. It was extracted with DCM (100 mL×3). The combined organic layers were washed with brine, dried over anhydrous $Na_2SO_4$, filtered and concentrated in-vacuo. The residue was then purified by silica gel chromatography eluted with MeOH:DCM=1:60 and then by Prep-HPLC to afford crude desired product LC-MS: m/e=374 [M+1]+ containing an impurity that was removed by the two-step sequence described below.

c) 4-{[(1,1-dimethylethyl)(diphenyl)silyl]oxy}-2-methyl-6-(4-morpholinyl)-1-(1-naphthalenylmethyl)-1H-benzimidazole

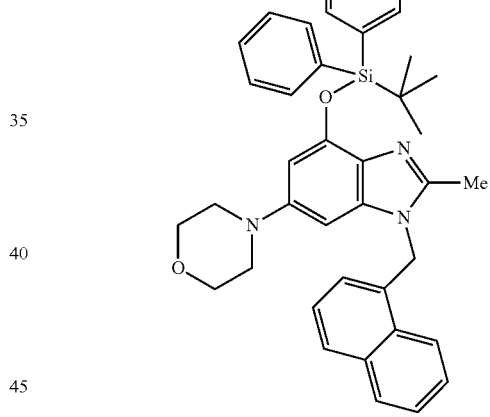

A mixture of crude 2-methyl-6-morpholino-1-(naphthalen-1-ylmethyl)-1H-benzo[d]imidazol-4-ol (200 mg), imidazole (73 mg) and TBDPSCl (162 mg) in dry DCM (30 mL) was stirred at room temperature for 1 h. LCMS analysis showed desired product so the solvent was removed in-vacuo. The residue was purified by silica gel chromatography eluted with EtOAc:petroleum ether=1:2 to afford the TBDP ether desired product as a white solid (260 mg, 79%). $^1$H NMR (300 MHz, $CDCl_3$) δ ppm 1.24 (s, 9H), 2.53-2.56 (m, 7H), 3.55 (t, 4H, J=4.8 Hz), 5.69 (s, 2H), 5.92 (d, 1H, J=1.8 Hz), 6.12 (d, 1H, J=1.8 Hz), 6.55 (d, 1H, J=7.5 Hz), 7.25-7.45 (m, 7H), 7.56-7.67 (m, 2H), 7.78 (d, 1H, J=8.7 Hz), 7.84-7.87 (m 4H), 7.94 (d, 1H, J=7.5 Hz), 8.06 (d, 1H, J=8.7 Hz); LC-MS: m/e=612 [M+1]+.

d) 2-methyl-6-morpholino-1-(naphthalen-1-ylmethyl)-1H-benzo[d]imidazol-4-ol

To a solution of 4-{[(1,1-dimethylethyl)(diphenyl)silyl]oxy}-2-methyl-6-(4-morpholinyl)-1-(1-naphthalenylmethyl)-1H-benzimidazole in THF (50 mL) was added TBAF (0.64 mL, 1 mol/L) at room temperature and the mixture was stirred for 1 h. TLC showed consumption of starting material. The solvent was removed in-vacuo and the residue was purified by silica gel chromatography eluted with MeOH: DCM=1:60 to afford the desired product as a white solid (150 mg, 94%). $^1$H NMR (300 MHz, DMSO-d$_6$) δ ppm 2.36 (s, 3H), 2.94 (t, 4H, J=4.8 Hz), 3.65 (t, 4H, J=4.8 Hz), 5.87 (s, 2H), 6.30 (d, 1H, J=1.8 Hz), 6.35 (d, 1H, J=1.8 Hz), 6.39 (d, 1H, J=7.5 Hz), 7.35 (t, 1H, J=7.5 Hz), 7.60-7.71 (m, 2H), 7.86 (d, 1H, J=8.4 Hz), 8.01 (d, 1H, J=7.5 Hz), 8.23 (d, 1H, J=8.4 Hz); LC-MS: m/e=374[M+1]+

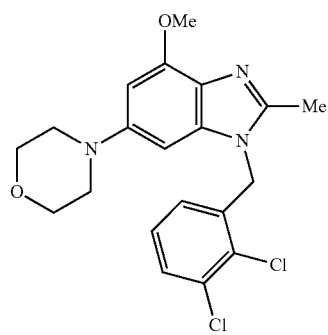 [SMILES: COc1cc(N2CCOCC2)cc2c1nc(C)n2Cc1cccc(Cl)c1Cl]

Preparation of 1-[(2,3-dichlorophenyl)methyl]-2-methyl-4-(methyloxy)-6-(4-morpholinyl)-1H-benzimidazole a) 2-methoxy-6-nitrobenzenamine

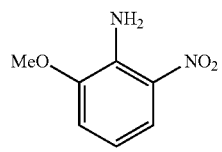

To a mixture of 2-amino-3-nitrophenol (19.25 g) and K$_2$CO$_3$ (19 g) in DMF (100 mL) was added MeI (11 mL) at room temperature and the mixture was stirred over night and then poured into water. The resulting precipitate was collected by filtration and the solid was washed with water to afford the desired product (19 g, 90%). $^1$H NMR (300 MHz, CDCl$_3$) δ ppm 3.92 (s, 1H), 6.43 (br s, 1H), 6.61 (dd, 1H, J=7.5, 9.0 Hz), 6.89 (dd, 1H, J=0.9, 7.5 Hz), 7.73 (dd, 1H, J=0.9, 9.0 Hz); LC-MS: m/e=169 [M+1]+ b) 4-bromo-2-methoxy-6-nitrobenzenamine

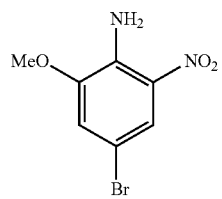 [SMILES: COc1cc(Br)cc([N+](=O)[O-])c1N]

NaOAc (17.6 g) and Br$_2$ (6.76 mL) was added to a solution of 2-methoxy-6-nitrobenzenamine (21.74 g) in HOAc (250 mL). The mixture was stirred at room temperature for 20 min. The resulting precipitate was filtered, washed with water and dried in-vacuo to afford the desired product as a yellow solid (26.43 g, 83%). $^1$H NMR (300 MHz, DMSO-d$_6$) δ 3.91 (s, 3H), 7.18 (d, 1H, J=1.8 Hz), 7.70 (d, 1H, J=1.8 Hz); LC-MS: m/e=247 [M+1]+ c) N-(4-bromo-2-methoxy-6-nitrophenyl)acetamide

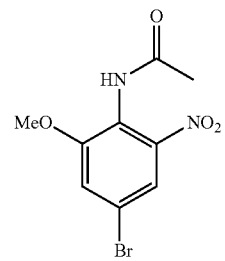 [SMILES: COc1cc(Br)cc([N+](=O)[O-])c1NC(C)=O]

To a solution of 4-bromo-2-methoxy-6-nitrobenzenamine (27.85 g) in HOAc (150 mL) and Ac$_2$O (17 mL) was added conc. H$_2$SO$_4$ at 70° C. and the mixture was stirred at 70° C. for 30 min and kept at rt overnight. The formed precipitate was collected by filtration and washed with hexane to afford the desired product as a light yellow solid (24.45 g, 75%). $^1$H NMR (300 MHz, DMSO-d6) δ ppm 2.01 (s, 3H), 3.92 (s, 3H), 7.61 (d, 1H, J=1.8 Hz), 7.65 (d, 1H, J=1.8 Hz), 9.91 (s, 1H); LC-MS: m/e=289 [M+1]+ d) N-(2-methoxy-4-morpholino-6-nitrophenyl)acetamide

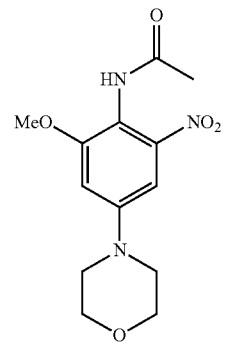

A mixture of N-(4-bromo-2-methoxy-6-nitrophenyl)acetamide (2.89 g), morpholine (2.61 g), BINAP (1.21 g) and t-BuOK (1.53 g) in dioxane (50 mL) was degassed with N$_2$ and the mixture was stirred at 110° C. in a sealed tube overnight. It was cooled to room temperature and filtered. The filtrate was concentrated in-vacuo. The residue was purified by silica gel chromatography eluted with MeOH/DCM=1/50 to afford the desired product (1.03 g, 35%) $^1$H NMR (300

MHz, CDCl$_3$) δ ppm 2.15 (s, 1H), 3.18 (t, 4H, J=4.8 Hz), 3.85 (t, 4H, J=4.8 Hz), 3.88 (s, 3H), 6.63 (d, 1H, J=2.7 Hz), 6.96 (d, 1H, J=2.7 Hz).

e) 4-(7-methoxy-2-methyl-3H-benzo[d]imidazol-5-yl)morpholine

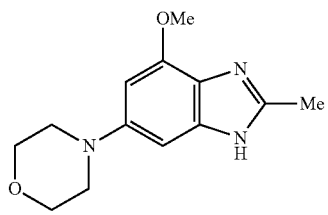 [SMILES: COc1cc(N2CCOCC2)cc2[nH]c(C)nc12]

To a refluxing solution of combined batches of N-(2-methoxy-4-morpholino-6-nitrophenyl)acetamide (2.06 g) in HOAc (60 mL) was added iron powder (1.18 g) and the mixture was stirred at reflux temperature overnight. It was cooled to room temperature and filtered. The filtrate was concentrated in-vacuo and the residue was washed with EtOAc:petroleum ether=1:1 to afford crude product as a solid (1.73 g, 100%). $^1$H NMR (300 MHz, DMSO-d$_6$) δ ppm 2.56 (s, 3H), 3.12 (t, 4H, J=4.8 Hz), 3.88 (t, 4H, J=4.8 Hz), 3.94 (s, 3H), 6.39 (s, 1H), 6.62 (s, 1H); LC-MS: m/e=248 [M+1]+ f) 1-[(2,3-dichlorophenyl)methyl]-2-methyl-4-(methyloxy)-6-(4-morpholinyl)-1H-benzimidazole A mixture of 18 (1.73 g), 1-(bromomethyl)-2,3-dichlorobenzene (1.68 g) and K$_2$CO$_3$ (1.93 g) in DMF (50 mL) was stirred at 80° C. for 72 h. The mixture was cooled to room temperature and poured into water. It was extracted with EtOAc and the organic layer was washed with brine, dried over anhydrous Na$_2$SO$_4$, filtered and concentrated in vacuo. The residue was then purified by silica gel chromatography eluted with 100% EtOAc and then MeOH:DCM=1:30 to afford the desired product as a white solid (360 mg, 9%) $^1$H NMR (CDCl$_3$, TMS, 300 MHz) δ ppm 2.48 (s, 3H), 3.11 (t, 4H, J=4.8 Hz), 3.85 (t, 4H, J=4.8 Hz), 4.02 (s, 3H), 5.31 (s, 2H), 6.19 (d, 1H, J=1.8 Hz), 6.30 (d, 1H, J=7.5 Hz), 6.42 (d, 1H, J=1.8 Hz), 7.03 (t, 1H, J=7.5 Hz), 7.41 (d, 1H, J=7.5 Hz); LC-MS: m/e=406 [M+1]+

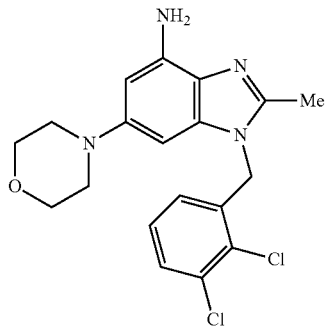

Preparation of 1-[(2,3-dichlorophenyl)methyl]-2-methyl-6-(4-morpholinyl)-1H-benzimidazol-4-amine a) 6-bromo-1-(2,3-dichlorobenzyl)-2-methyl-4-nitro-1H-benzo[d]imidazole

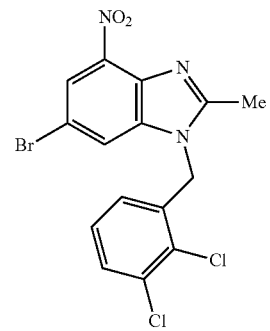

A mixture of Example 1 (1.17 g) (prepared as described previously), 1-(bromomethyl)-2,3-dichlorobenzene (1.19 g) and K$_2$CO$_3$ (1.27 g) in DMF (80 mL) was stirred at 80° C. for 3 h. When TLC showed no starting material, the mixture was cooled to room temperature and filtered. The filtrate was then poured into water. It was then filtered to afford a solid and the solid was washed with water and then dried in-vacuo to afford the desired product (1.59 g, 83%) $^1$H NMR (300 MHz, CDCl$_3$) δ ppm 2.67 (s, 3H), 5.45 (m, 2H), 6.24 (t, 1H, J=7.8 Hz), 7.10 (t, 1H, J=7.8 Hz), 7.47 (t, 1H, J=7.8 Hz), 7.59 (d, 1H, J=1.8 Hz), 8.24 (d, 1H, J=1.8 Hz); LC-MS: m/e=416 [M+1]+.

b) 4-(3-(2,3-dichlorobenzyl)-2-methyl-7-nitro-3H-benzo[d]imidazol-5-yl)morpholine

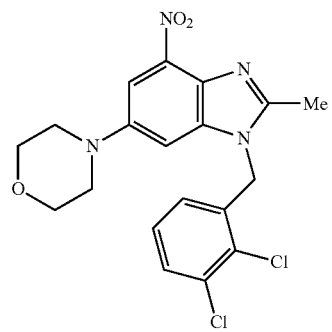 [SMILES: Cc1nc2c(N)cc(N3CCOCC3)cc2n1Cc1cccc(Cl)c1Cl]

A mixture of 6-bromo-1-(2,3-dichlorobenzyl)-2-methyl-4-nitro-1H-benzo[d]imidazole (1.69 g), morpholine (1.07 g), Pd$_2$(dba)$_3$ (376 mg), Cs$_2$CO$_3$ (2 g) and X-Phos (383 mg) in dioxane (80 mL) was degassed with nitrogen and then stirred at 80° C. for 3 h. When TLC showed complete consumption of starting material, the mixture was cooled to room temperature and the solvent was removed in-vacuo. The remaining residue was extracted with EtOAc. The organic layer was washed with brine, dried over anhydrous Na$_2$SO$_4$, filtered and concentrated in-vacuo. The residue was then purified by silica gel chromatography eluted with EtOAc:Petrolium ether=1:1 to afford the desired product as a yellow solid (831 mg, 48%). $^1$H NMR (300 MHz, CDCl$_3$) δ ppm 2.62 (s, 3H), 3.18 (t, 4H, J=4.8 Hz), 3.87 (t, 4H, J=4.8 Hz), 5.41 (s, 2H), 6.28 (d, 1H, J=7.8 Hz), 6.86 (d, 1H, J=2.4 Hz), 7.08 (t, 1H, J=7.8 Hz), 7.46 (d, 1H, J=7.8 Hz), 7.79 (d, 1H, J=2.4 Hz); LC-MS: m/e=421 [M+1]+ c) 1-[2,3-dichlorophenyl)methyl]-2-methyl-6-(4-morpholinyl)-1H-benzimidazol-4-amine A mixture of 4-(3-(2,3-dichlorobenzyl)-2-methyl-7-nitro-3H-benzo[d]imidazol-5-yl)morpholine (210 mg), iron powder (56 mg) and FeSO$_4$ (152 mg) in ethanol (25 mL) and H$_2$O (25 mL) was stirred at reflux temperature for 3 h. When TLC showed consumption of all starting material, the mixture was cooled to room temperature and filtered. The filtrate was concentrated in-vacuo and the residue was then purified by silica gel chromatography eluted with MeOH:DCM:NH$_3$.H$_2$O=1:60:0.5% to afford the desired product as a yellow solid (137 mg, 70%). $^1$H NMR (300 MHz, DMSO-d$_6$) δ ppm 2.32 (s, 1H), 2.94 (t, 4H, J=4.8 Hz), 3.68 (t, 4H, J=4.8 Hz), 5.16 (br, s, 2H), 5.40 (s, 2H), 6.09 (d, 1H, J=1.8 Hz), 6.13 (d, 1H, J=1.8 Hz), 6.32 (dd, 1H, J=1.5, 7.5 Hz), 7.25 (t, 1H, J=7.5 Hz), 7.58 (dd, 1H, J=1.5, 7.5 Hz); LC-MS: m/e=391 [M+1]+.

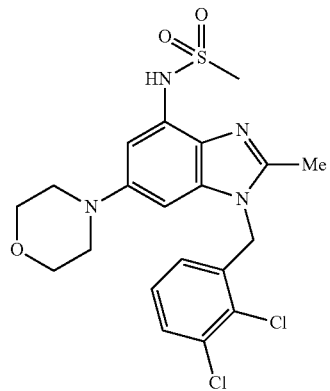 [SMILES: Cc1nc2c(NS(C)(=O)=O)cc(N3CCOCC3)cc2n1Cc1cccc(Cl)c1Cl]

Preparation of N-[1-[(2,3-dichlorophenyl)methyl]-2-methyl-6-(4-morpholinyl)-1H-benzimidazol-4-yl]methanesulfonamide To a solution of Example 7 (82 mg) and Et$_3$N (42 mg) and dry DCM (20 mL) was added a solution of methanesulfonyl chloride (40 mg) in DCM at 0° C. and then the mixture was stirred at room temperature for 30 min. TLC showed no starting material remaining and some di-mesylated product was detected by LC-MS: m/e=547 [M+1]+. The solvent was removed in vacuo, THF (10 mL) and 2N aqueous NaOH solution (10 mL) was added. The mixture was stirred at room temperature for 2 h. The desired product was detected as the main product on LC-MS. It was extracted with DCM (75 mL×2) and the combined organic layers were concentrated in-vacuo. The residue was purified by silica gel chromatography eluted with MeOH:DCM:NH$_3$.H$_2$O=1:60:0.5% to afford the desired product as a yellow solid (25 mg, 26%). $^1$H NMR (300 MHz, DMSO-d$_6$) δ 2.40 ppm (s, 1H), 3.03-3.04 (m, 4H), 3.09 (s, 3H), 3.70-3.75 (m, 4H), 5.5-5.56 (m, 2H), 6.31-6.34 (m, 1H), 6.80-6.82 (m, 2H), 7.25-7.30 (m, 1H), 7.60-7.62 (m, 1H), 9.50 (s, 1H); LC-MS: m/e=469 [M+1]+

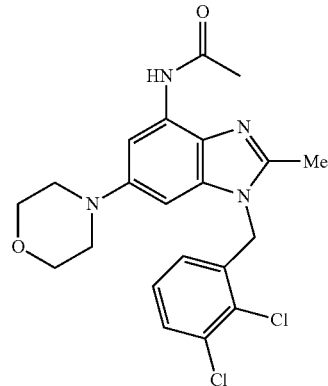 [SMILES: CC(=O)Nc1cc(N2CCOCC2)cc2c1nc(C)n2Cc1cccc(Cl)c1Cl]

Preparation of N-[1-[(2,3-dichlorophenyl)methyl]-2-methyl-6-(4-morpholinyl)-1H-benzimidazol-4-yl]acetamide To a solution of Example 7 (78 mg) and Et$_3$N (30 mg) in dry DCM (30 mL) was added a solution of Ac$_2$O (20 mg) in DCM at 0° C. and then the mixture was stirred at room temperature for 2 h. The mixture was then stirred at reflux temperature for until TLC showed no starting material. The mixture was cooled to room temperature and diluted with DCM (150 mL) and washed with brine (100 mL×2). The organic layer was concentrated in-vacuo and the residue was purified by silica gel chromatography eluted with MeOH:DCM=1:60 and then by Prep-HPLC to afford the desired product as a yellow solid (21 mg, 24%). $^1$H NMR (300 MHz, CDCl$_3$) δ ppm 2.28 (s, 3H), 2.48 (s, 3H), 3.14 (t, 4H, J=4.8 Hz), 3.84 (t, 4H, J=4.8 Hz), 5.33 (s, 2H), 6.28-6.30 (m, 2H), 7.05 (t, 1H, J=8.1 Hz), 7.42 (dd, 1H, J=1.2 Hz, J=8.1 Hz), 8.08 (d, 1H, J=1.8 Hz), 8.27 (br s, 1H); LC-MS: m/e=433 [M+1]+.

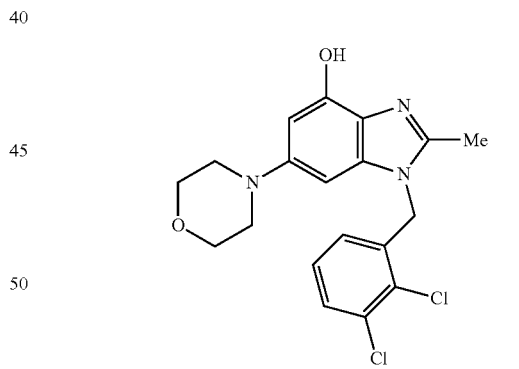

Preparation of 1-[(2,3-dichlorophenyl)methyl]-2-methyl-6-(4-morpholinyl)-1H-benzimidazol-4-ol The titled compound was prepared following the same procedure as Example 5 replacing 1-(bromomethyl)naphthalene with 1-(bromomethyl)-2,3-dichlorobenzene. (130 mg, 69%). $^1$H NMR (300 MHz, DMSO-d$_6$) δ ppm 2.35 (s, 3H), 2.97 (t, 4H, J=4.8 Hz), 3.68 (t, 4H, J=4.8 Hz), 5.44 (s, 2H), 6.24 (d, 1H, J=2.1 Hz), 6.31 (dd, 1H, J=1.2, 7.8 Hz), 6.38 (d, 1H, J=2.1 Hz), 7.26 (t, 1H, J=7.8 Hz), 7.59 (dd, 1H, J=1.2, 7.8 Hz), 9.61 (s, 1H); LC-MS: m/e=392[M+1]+.

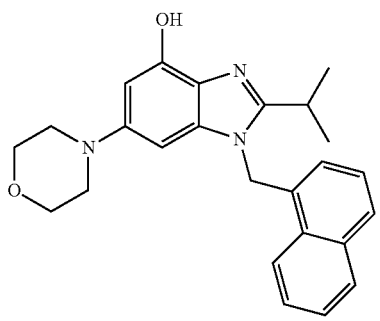 [SMILES: CC(C)c1nc2c(O)cc(N3CCOCC3)cc2n1Cc1cccc2ccccc12]

Preparation of 2-(1-methylethyl)-6-(4-morpholinyl)-1-(1-naphthalenylmethyl)-1H-benzimidazol-4-ol a) 6-bromo-2-isopropyl-4-nitro-1H-benzo[d]imidazole

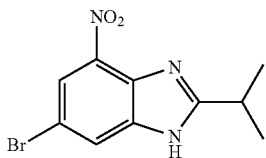 [SMILES: CC(C)c1nc2c([N+](=O)[O-])cc(Br)cc2[nH]1]

A mixture of 5-bromo-3-nitrobenzene-1,2-diamine (prepared following the same procedure as for Example 1, 5.0 g) in isobutyric acid (20 mL) was stirred at 120° C. overnight. The mixture was cooled to room temperature and poured into water (100 mL). The pH was neutralized with aqueous Na₂CO₃ solution. It was then extracted with EtOAc and the organic layer was washed with water and brine, dried over anhydrous MgSO₄, filtered and concentrated in-vacuo. The residue was then purified by silica gel chromatography eluted with EtOAc:petroleum ether=1:1 to afford the desired product as a yellow solid (4.7 g, 77%). ¹H NMR (300 MHz, CDCl₃) δ ppm 1.51 (m, 6H, J=6.9 Hz), 3.32 (m, 1H, J=6.9 Hz), 8.16 (d, 1H, J=1.5 Hz), 8.25 (d, 1H, J=1.5 Hz), 10.26 (br s, 1H); LC-MS: m/e=284 [M+1]+ b) 6-bromo-2-(1-methylethyl)-1-(1-naphthalenylmethyl)-4-nitro-1H-benzimidazole

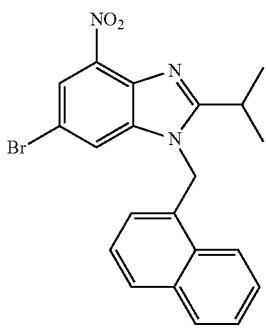 [SMILES: CC(C)c1nc2c([N+](=O)[O-])cc(Br)cc2n1Cc1cccc2ccccc12]

A mixture of 6-bromo-2-isopropyl-4-nitro-1H-benzo[d]imidazole (4.7 g), 1-(bromomethyl)naphthalene (4.01 g) and K₂CO₃ (4.55 g) in DMF (150 mL) was stirred at 80° C. for 2 h. It was cooled to room temperature and filtered. The filtrate was then poured into water (1 L). It was then filtered to afford a solid that was washed with water and then dried in-vacuo to afford the crude product (7.2 g). LC-MS: m/e=425 [M+1]+ c) 2-(1-methylethyl)-6-(4-morpholinyl)-1-(1-naphthalenylmethyl)-4-nitro-1H-benzimidazole

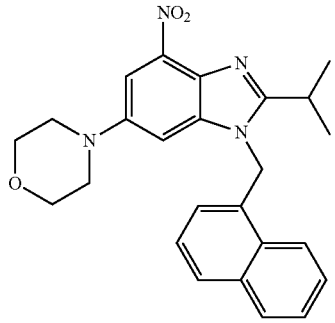 [SMILES: CC(C)c1nc2c([N+](=O)[O-])cc(N3CCOCC3)cc2n1Cc1cccc2ccccc12]

A mixture of 6-bromo-2-(1-methylethyl)-1-(1-naphthalenylmethyl)-4-nitro-1H-benzimidazole (2.05 g), morpholine (1.26 g), Pd₂(dba)₃ (0.46 g), Cs₂CO₃ (2.36 g) and X-Phos (0.41 g) in dioxane (30 mL) was degassed with nitrogen and then stirred at 80° C. overnight. The mixture was cooled to room temperature and the solvent was removed in-vacuo. The residue was then purified by silica gel chromatography eluted with (EtOAc:petroleum ether=1:1) to afford the desired product as a yellow solid (1.6 g, 77%). LC-MS: m/e=431 [M+1]+ d) 2-(1-methylethyl)-6-(4-morpholinyl)-1-(1-naphthalenylmethyl)-1H-benzimidazol-4-amine

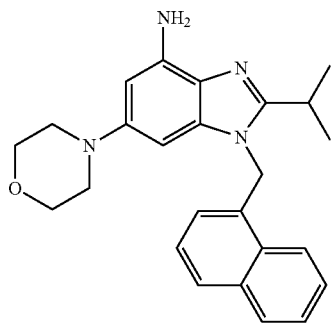

TiCl₃ (16.3 mL) was added to a solution of 2-(1-methylethyl)-6-(4-morpholinyl)-1-(1-naphthalenylmethyl)-4-nitro-1H-benzimidazole (1.6 g) and NH₄OAc (4 g) in MeOH (40 mL). After stirring for 4 h at room temperature, TLC showed no starting material. The pH of the mixture was made basic by adding Na₂CO₃ aqueous solution. The solvent was evaporated off under reduced pressure and the residue was extracted with DCM (250 mL×2). The combined organic layers were washed with brine, dried over anhydrous Na₂SO₄, filtered and concentrated in-vacuo to afford the desired product as a white solid (1.2 g, 81%). LC-MS: m/e=401 [M+1]+.

e) 2-(1-methylethyl)-6-(4-morpholinyl)-1-(1-naphthalenylmethyl)-1H-benzimidazol-4-ol To a solution of 2-(1-methylethyl)-6-(4-morpholinyl)-1-(1-naphthalenylmethyl)-1H-benzimidazol-4-amine (300 mg) in H$_2$O (20 mL), and conc. H$_2$SO$_4$ (1 mL) was added aqueous NaNO$_2$ (78 mg) solution dropwise at 0° C. The mixture was stirred at 0° C. for 15 min and then heated to reflux for 1 h. The mixture was cooled to room temperature and the pH neutralized with aqueous NaHCO$_3$ solution. The solution was extracted with DCM (250 mL×3). The combined organic layers were washed with brine, dried over anhydrous Na$_2$SO$_4$, filtered and concentrated in-vacuo. The residue was then purified by silica gel chromatography eluted with EtOAc:petroleum ether=1:1 to afford the desired product as a solid (80 mg, 27%). $^1$H NMR (300 MHz, DMSO-d$_6$) δ ppm 1.21 (d, 6H, J=6.6 Hz), 2.91 (t, 4H, J=7.5 Hz), 3.03 (m, 1H, J=6.6 Hz), 3.64 (t, 4H, J=7.5 Hz), 5.89 (s, 2H), 6.27-6.34 (m, 3H), 7.32 (t, 1H, J=7.5 Hz), 7.59-7.70 (m, 2H), 7.83 (d, 1H, J=7.5 Hz), 8.00 (d, 1H, J=7.5 Hz), 8.27 (d, 1H, J=7.5 Hz), 9.55 (s, 1H); LC-MS: m/e=402 [M+1]+.

Example 12

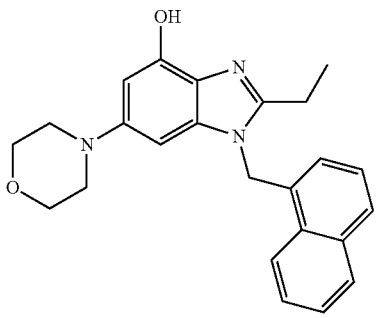

Preparation of 2-ethyl-6-(4-morpholinyl)-1-(1-naphthalenylmethyl)-1H-benzimidazol-4-ol The titled compound was prepared following the same procedure as Example 11 replacing isobutyric acid with propionic acid. $^1$H NMR (300 MHz, DMSO-d$_6$) δ ppm 1.20 (t, 3H, J=7.5 Hz), 2.67 (q, 2H, J=7.5 Hz), 2.93 (t, 4H, J=4.5 Hz), 3.64 (t, 4H, J=4.5 Hz), 5.86 (s, 2H), 6.26 (s, 1H), 6.33-6.34 (m, 2H), 7.32 (t, 1H, J=7.5 Hz), 7.57-7.68 (m, 2H), 7.82 (d, 1H, J=8.1 Hz), 7.98 (d, 1H, J=7.5 Hz), 8.23 (d, 1H, J=8.1 Hz), 9.54 (s, 1H); LC-MS: m/e=388 [M+1]+.

Example 13

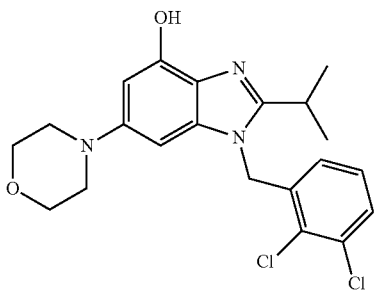

Preparation of 1-[(2,3-dichlorophenyl)methyl]-2-(1-methylethyl)-6-(4-morpholinyl)-1H-benzimidazol-4-ol The titled compound was prepared following the same procedure as Example 11 replacing 1-(bromomethyl)naphthalene with 1-(bromomethyl)-2,3-dichlorobenzene. $^1$H NMR (300 MHz, CDCl$_3$) δ ppm 1.20 (d, 6H, J=6.9 Hz), 2.94-3.06 (m, 2H), 3.67 (t, 4H, J=4.5 Hz), 5.45 (s, 2H), 6.24-6.26 (m, 2H), 6.34 (s, 1H), 7.23 (d, 1H, J=7.8 Hz), 7.56 (d, 1H, J=7.8 Hz), 9.54 (s, 1H); LC-MS: m/e=420 [M+1]+.

Example 14

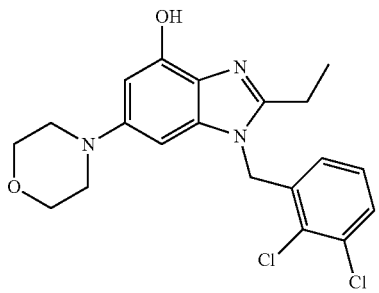

Preparation of 1-[(2,3-dichlorophenyl)methyl]-2-ethyl-6-(4-morpholinyl)-1H-benzimidazol-4-ol The titled compound was prepared following the same procedure as Example 12 replacing 1-(bromomethyl)naphthalene with 1-(bromomethyl)-2,3-dichlorobenzene. $^1$H NMR (300 MHz, CDCl$_3$) δ ppm 1.29 (t, 3H, J=7.5 Hz), 2.86 (q, 2H, J=7.5 Hz), 3.10 (t, 4H, J=4.8 Hz), 3.82 (t, 4H, J=4.8 Hz), 5.32 (s, 2H), 6.10 (d, 1H, J=2.4 Hz), 6.37 (dd, 2H, J=1.5, 7.8 Hz), 6.54 (d, 1H, J=2.4 Hz), 7.04 (t, 1H, J=7.8 Hz), 7.4 (dd, 1H, J=1.5, 7.8 Hz); LC-MS: m/e=406 [M+1]+

Example 15

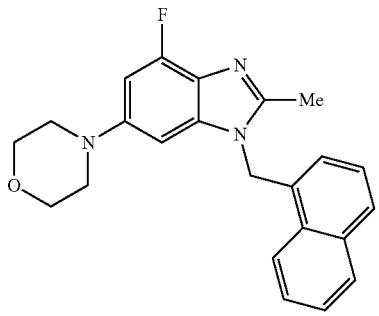

Preparation of 4-fluoro-2-methyl-6-(4-morpholinyl)-1-(1-naphthalenylmethyl)-1H-benzimidazole To a solution of 2-methyl-6-morpholino-1-(naphthalen-1-ylmethyl)-1H-benzo[d]imidazol-4-amine (prepared following the same procedure used for Example 2) (200 mg) in 70% HF/pyridine (2 mL) in a Teflon reactor was added NaNO$_2$ (56 mg) at −50° C. and the mixture was stirred at −50° C. for 30 min and then heated to 70° C. for 1 h. The mixture was cooled to room temperature and the pH neutralized with aqueous Na$_2$CO$_3$ solution. It was then extracted with DCM (100 mL×2). The combined organic layers were concentrated in-vacuo and the residue was purified by Prep-TLC developed with EtOAc:petroleum ether=1:1 to afford the desired product as a solid (10 mg, 5%). $^1$H NMR (300 MHz, CDCl$_3$) δ ppm 2.54 (s, 3H), 3.05 (t, 4H, J=4.8 Hz), 3.79 (t, 4H, J=4.8

Hz), 5.75 (s, 2H), 6.37 (d, 1H, J=1.8 Hz), 6.53 (d, 1H, J=7.5 Hz), 6.66-6.71 (m, 1H), 7.30 (t, 1H, J=7.5 Hz), 7.59-7.69 (m, 2H), 7.81 (d, 1H, J=9.0 Hz), 7.96 (d, 1H, J=7.5 Hz), 8.05 (d, 1H, J=7.8 Hz); LC-MS: m/e=376 [M+1]⁺.

Example 16

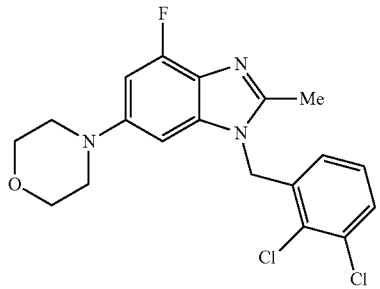

Preparation of 1-[(2,3-dichlorophenyl)methyl]-4-fluoro-2-methyl-6-(4-morpholinyl)-1H-benzimidazole To a solution of 1-[(2,3-dichlorophenyl)methyl]-2-methyl-6-(4-morpholinyl)-1H-benzimidazol-4-amine (prepared following the same procedure as for Example 7, 200 mg) in 70% HF/pyridine (4 mL) in a Teflon reactor was added NaNO₂ (53 mg) at −50° C. and the mixture was stirred at −50° C. for 30 min and then heated to 70° C. for 1 h. The mixture was cooled to room temperature and the pH was neutralized with aqueous Na₂CO₃ solution. It was then extracted with DCM (100 mL×2). The combined organic layers were concentrated in-vacuo and the residue was purified by Prep-TLC developed with MeOH:DCM=1:30 to afford the desired product as a solid (40 mg, 20%). ¹H NMR (300 MHz, CDCl₃) δ 2.49 ppm (s, 3H), 3.09 (t, 4H, J=4.5 Hz), 3.83 (t, 4H, J=4.5 Hz), 5.32 (s, 2H), 6.29-6.33 (m, 2H), 6.66 (d, 1H, J=7.8 Hz), 7.06 (t, 1H, J=7.8 Hz), 7.42 (d, 1H, J=7.8 Hz); LC-MS: m/e=394 [M+1]⁺

Example 17

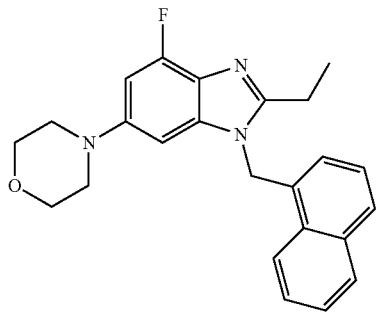

Preparation of 2-ethyl-4-fluoro-6-(4-morpholinyl)-1-(1-naphthalenylmethyl)-1H-benzimidazole To a solution of 2-ethyl-6-(4-morpholinyl)-1-(1-naphthalenylmethyl)-1H-benzimidazol-4-amine (prepared following the same procedure as for Example 12, 200 mg, 0.49 mmol) in 70% HF/pyridine (3 mL) was added NaNO₂ (50 mg, 0.73 mmol) at −50° C. and the resulting mixture was further stirred for 1 h. Then the mixture was heated to 70° C. for 1 h. The mixture was cooled to rt and extracted with DCM (30 mL×3). The combined organic layers were dried over Na₂SO₄, concentrated in-vacuo. The resulting residue was purified by Prep-TLC to give the product (20 mg, 10%), as a white solid. ¹H NMR (300 MHz, DMSO-d₆) δ ppm 1.22 (t, 3H, J=7.5 Hz), 2.69 (q, 2H, J=7.5 Hz), 3.02 (t, 4H, J=3.9 Hz), 3.66 (t, 4H, J=3.9 Hz), 5.97 (s, 2H), 6.32 (d, 1H, J=7.8 Hz), 6.74-6.79 (m, 2H), 7.34 (t, 1H, J=7.8 Hz), 7.60-7.70 (m, 2H), 7.85 (d, 1H, J=8.4 Hz), 8.00 (d, 1H, J=7.8 Hz), 8.24 (d, 1H, J=7.8 Hz); LC-MS: m/e=390 [M+1]⁺.

Example 18

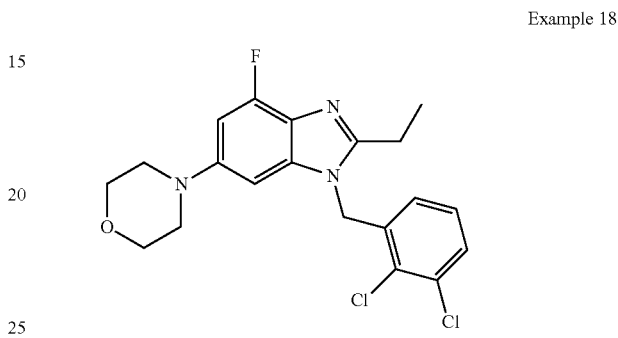

Preparation of 1-[(2,3-dichlorophenyl)methyl]-2-ethyl-4-fluoro-6-(4-morpholinyl)-1H-benzimidazole To a solution of 1-[(2,3-dichlorophenyl)methyl]-2-ethyl-6-(4-morpholinyl)-1H-benzimidazol-4-amine (prepared following the same procedure as for Example 14, 203 mg) in 70% HF/pyridine (2 mL) in a Teflon reactor was added NaNO₂ (52 mg) at −50° C. and the mixture was stirred at −50° C. for 30 min and then heated to 70° C. for 1 h. The mixture was cooled to room temperature and the pH neutralized with aqueous Na₂CO₃ solution. It was then extracted with DCM (100 mL×2). The combined organic layers were concentrated in-vacuo and the residue was purified by Prep-TLC developed with EtOAc:peterolium ether=1:1 to afford the desired product as a solid (5 mg, 4%). ¹H NMR (300 MHz, CDCl₃): δ 1.39 ppm (t, 3H, J=7.5 Hz), 2.80 (q, 2H, J=7.5 Hz), 3.10 (t, 4H, J=4.8 Hz), 3.84 (t, 4H, J=4.8 Hz), 5.34 (s, 2H), 6.29-6.34 (m, 2H), 6.68 (dd, 1H, J=1.8, 12.6 Hz), 7.06 (t, 1H, J=7.8 Hz), 7.43 (d, 1H, J=7.8 Hz); LC-MS: m/e=408 [M+1]⁺.

Example 19

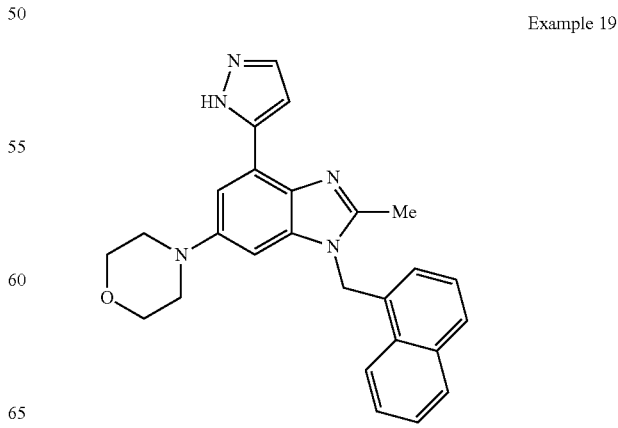

Preparation of 2-methyl-6-(4-morpholinyl)-1-(1-naphthalenylmethyl)-4-(1H-pyrazol-5-yl)-1H-benzimidazole a) 4-bromo-2-methyl-6-(4-morpholinyl)-1-(1-naphthalenylmethyl)-1H-benzimidazole

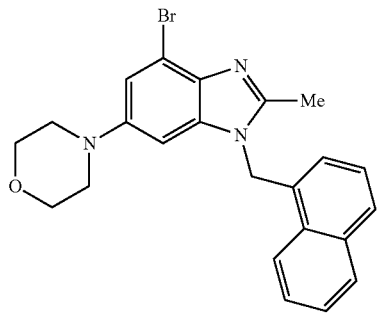 [SMILES: Cc1nc2c(Br)cc(N3CCOCC3)cc2n1Cc1cccc2ccccc12]

To a solution of 2-methyl-6-(4-morpholinyl)-1-(1-naphthalenylmethyl)-1H-benzimidazol-4-amine (prepared following the same procedure as for Example 2, 1.1 g, 3 mmol) in aqueous HBr (50 mL) was added aqueous NaNO$_2$ (214 mg, 3.1 mmol) solution dropwise at 0-5° C. After addition the mixture was stirred at 0° C. for 5 minutes, it was added to another solution of NaBr (927 mg, 9 mmol) in aqueous HBr (50 mL) dropwise at 60° C. The resulting mixture was then heated to 80° C. for 30 minutes and then cooled to room temperature. The solution pH was neutralized with aqueous NaHCO$_3$ (600 mL) and extracted with DCM (500 mL×3). The combined organic layers were concentrated in vacuum and the residue was purified by silica gel chromatography eluted with petroleum ether:EtOAc=1:1 to give the desired product (725 mg, 55%) as a white solid. $^1$H NMR (300 MHz, CDCl$_3$) δ 2.55 ppm (s, 3H), 3.05 (t, 4H, J=4.8 Hz), 3.79 (t, 4H, J=4.8 Hz), 5.73 (s, 2H), 6.50 (dd, 1H, J=1.2, 7.5 Hz), 6.53 (d, 1H, J=1.8 Hz), 7.15 (d, 1H, J=1.8 Hz), 7.28 (t, 1H, J=7.5 Hz), 7.60-7.67 (m, 2H), 7.81 (d, 1H, J=8.4 Hz), 7.96 (d, 1H, J=7.5 Hz), 8.06 (d, 1H, J=8.4 Hz); LC-MS: m/e=436 [M+1]$^+$.

b) 2-methyl-6-(4-morpholinyl)-1-(1-naphthalenylmethyl)-4-(1H-pyrazol-5-yl)-1H-benzimidazole A mixture of 4-bromo-2-methyl-6-(4-morpholinyl)-1-(1-naphthalenylmethyl)-1H-benzimidazole (200 mg, 0.46 mmol), 1H-pyrazol-5-ylboronic acid (100 mg, 0.92 mmol), Pd(dba)$_2$ (40 mg, 0.046 mmol), Cs$_2$CO$_3$ (300 mg, 0.92 mmol) and P(t-Bu)$_3$ (10 wt % in hexane, 20 mg, 0.092 mmol) in dioxane (20 mL) and water (10 mL), was stirred at 100° C. for 18 h under a nitrogen atmosphere. The reaction mixture was cooled and then concentrated. The resulting residue was purified by silica gel chromatography eluted with EtOAc to give the product (140 mg 72%), as a white solid. $^1$H NMR showed this compound is in a form of tautomeric mixture (major tautomer/minor tautomer=5/3) $^1$H NMR of the major tautomer (300 MHz, DMSO-d$_6$) δ ppm 2.45 (s, 3H), 3.08 (s, 4H), 3.71 (s, 4H), 6.00 (s, 2H), 6.37 (d, 1H, J=7.2 Hz), 6.96 (s, 1H), 7.24-7.72 (m, 6H), 7.83-7.87 (m, 1H), 8.01 (d, 1H, J=7.2 Hz), 8.25 (d, 1H, J=4.2 Hz), 13.24 (br s, 1H); LC-MS: m/e=424 [M+1]$^+$ Example 20

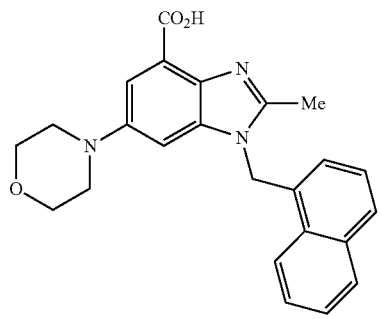

Preparation of 2-methyl-6-(4-morpholinyl)-1-(1-naphthalenylmethyl)-1H-benzimidazole-4-carboxylic acid a) methyl 2-methyl-6-(4-morpholinyl)-1-(1-naphthalenylmethyl)-1H-benzimidazole-4-carboxylate

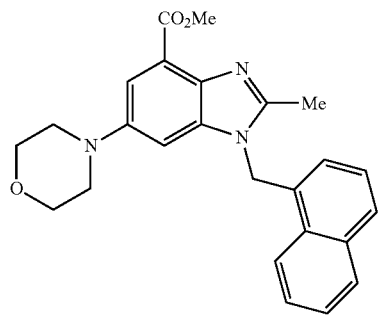 [SMILES: COC(=O)c1cc(N2CCOCC2)cc2c1nc(C)n2Cc1cccc2ccccc12]

A mixture of intermediate 4-bromo-2-methyl-6-(4-morpholinyl)-1-(1-naphthalenylmethyl)-1H-benzimidazole, prepared following the same procedure as for Example 19 (400 mg, 0.92 mmol), dppf (51 mg, 0.092 mmol), Pd(AcO)$_2$ (20.6 mg, 0.092 mmol) and triethylamine (111 mg, 1.1 mmol) in methanol (50 mL), was degassed with CO(g). Then the reaction mixture was stirred at 60° C. for 18 h under a CO(g) atmosphere. The reaction mixture was cooled, concentrated. The resulting residue was purified by silica gel chromatography eluted with EA to give the desired product (170 mg, 45%), as a white solid. $^1$H NMR (300 MHz, DMSO-d$_6$) δ ppm 2.42 (s, 3H), 3.05 (t, 4H, J=4.8 Hz), 3.69 (t, 4H, J=4.8 Hz), 3.90 (s, 3H), 6.02 (s, 2H), 6.28 (d, 1H, J=8.4 Hz), 7.29-7.39 (m, 3H), 7.60-7.71 (m. 2H), 7.85 (d, 1H, J=8.4 Hz), 8.01 (d, 1H, J=8.4 Hz), 8.24 (d, 1H, J=8.4 Hz); LC-MS: m/e=416 [M+1]$^+$ b) 2-methyl-6-(4-morpholinyl)-1-(1-naphthalenylmethyl)-1H-benzimidazole-4-carboxylic acid A mixture of methyl 2-methyl-6-(4-morpholinyl)-1-(1-naphthalenylmethyl)-1H-benzimidazole-4-carboxylate (170 mg, 0.41 mmol) and LiOH (172 mg, 4.1 mmol) in THF (15 mL) and water (10 mL), was stirred at 50° C. for 1 h. Then the pH of the reaction mixture was neutralized with 1N aq. HCl. Then the mixture was stirred at rt for 1 h, filtered to give the desired product (150 mg, 91%), as a white solid. $^1$H NMR (300 MHz, DMSO-d6) δ ppm 2.51 (s, 3H), 3.07 (t, 4H, J=4.8

Hz), 3.70 (t, 4H, J=4.8 Hz), 6.09 (s, 2H), 6.38 (d, 1H, J=7.8 Hz), 7.32-7.46 (m. 3H), 7.60-7.73 (m, 2H), 7.87 (d, 1H, J=7.8 Hz), 8.02 (d, 1H, J=8.4 Hz), 8.23 (d, 1H, J=8.1 Hz); LC-MS: m/e=402 [M+1]⁺

Example 21

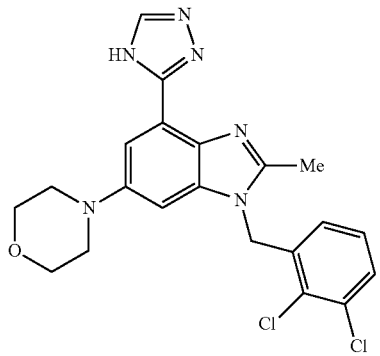

Preparation of 1-[(2,3-dichlorophenyl)methyl]-2-methyl-6-(4-morpholinyl)-4-(1H-1,2,4-triazol-3-yl)-1H-benzimidazole a) 4-bromo-1-[(2,3-dichlorophenyl)methyl]-2-methyl-6-(4-morpholinyl)-1H-benzimidazole

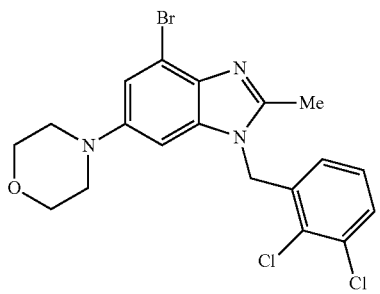 [SMILES: Cc1nc2c(Br)cc(N3CCOCC3)cc2n1Cc1cccc(Cl)c1Cl]

A solution of NaNO₂ (0.37 g, 5.4 mmol) in water (0.5 ml) was added to a solution of 1-[(2,3-dichlorophenyl)methyl]-2-methyl-6-(4-morpholinyl)-1H-benzimidazol-4-amine (prepared following the same procedure as for Example 7, 2.0 g, 5 mmol) in HBr (60 mL) at 0-5° C. and stirred for 15 min. The mixture was added dropwise to a solution of NaBr (1.5 g, 15 mmol) in HBr (60 ml) at 60° C., and then heated to 80° C. for 30 min. The mixture was cooled to rt and poured into a Na₂CO₃ solution (200 ml). The mixture was extracted with DCM (100 mL×3). The combined organic layers were dried over Na₂SO₄, filtered, concentrated. The residue was purified by silica gel chromatography eluted with EtOAc to give the product (1 g, 44%), as a white solid. ¹H NMR (300 MHz, DMSO-d₆) δ ppm 2.39 (s, 3H), 3.06 (t, 4H, J=4.8 Hz), 3.70 (t, 4H, J=4.8 Hz), 5.53 (s, 2H), 6.31 (dd, 1H, J=1.2, 7.8 Hz), 7.02 (d, 1H, J=2.1 Hz), 7.09 (d, 1H, J=2.1 Hz), 7.26 (t, 1H, J=7.8 Hz), 7.60 (dd, 1H, J=1.2 Hz, 7.8 Hz); LC-MS: m/e=455 [M+1]⁺.

b) 1-[(2,3-dichlorophenyl)methyl]-2-methyl-6-(4-morpholinyl)-1H-benzimidazole-4-carbonitrile

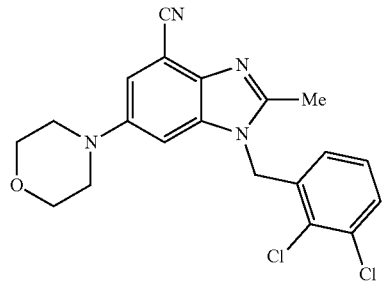 [SMILES: Cc1nc2c(C#N)cc(N3CCOCC3)cc2n1Cc1cccc(Cl)c1Cl]

A mixture of 4-bromo-1-[(2,3-dichlorophenyl)methyl]-2-methyl-6-(4-morpholinyl)-1H-benzimidazole (1 g, 2.2 mmol), Pd(dba)₂ (161 mg, 0.22 mmol), dppf (244 mg, 0.44 mmol), Zn(CN)₂ (1030 mg, 8.8 mmol), water (1 mL), Fe(OAc)₂ (191 mg, 1.1 mmol) and Zn powder (429 mg, 6.6 mmol) in DMF (50 mL) was stirred at 100° C. under N₂ for 20 h. When TLC showed no starting material remaining, the reaction mixture was quenched with water and extracted with EtOAc (100 mL×3). The organic layer was washed with brine, dried over MgSO₄, concentrated. The resulting residue was purified by silica gel chromatography eluted with EtOAc to give the product (400 mg, 45%), as a white solid. ¹H NMR (300 MHz, DMSO-d₆) δ ppm 2.43 (s, 3H), 3.11 (t, 4H, J=4.8 Hz), 3.72 (t, 4H, J=4.8 Hz), 5.60 (s, 2H), 6.30 (dd, 1H, J=1.2, 8.1 Hz), 7.25 (t, 1H, J=8.1 Hz), 7.35 (d, 1H, J=2.1 Hz), 7.42 (d, 1H, J=2.1 Hz), 7.60 (dd, 1H, J=1.2, 8.1 Hz); LC-MS: m/e=401 [M+1]⁺.

c) 11-[(2,3-dichlorophenyl)methyl]-2-methyl-6-(4-morpholinyl)-1H-benzimidazole-4-carboxamide

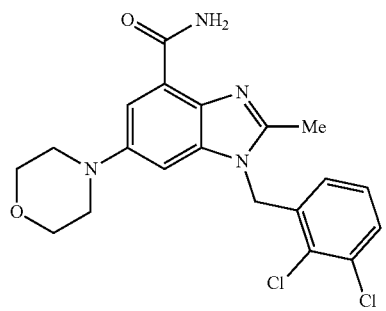 [SMILES: Cc1nc2c(C(N)=O)cc(N3CCOCC3)cc2n1Cc1cccc(Cl)c1Cl]

A solution of KOH (78 mg, 1.4 mmol) in water (10 mL) was added dropwise to solution of 1-[(2,3-dichlorophenyl)methyl]-2-methyl-6-(4-morpholinyl)-1H-benzimidazole-4-carbonitrile (280 mg, 0.7 mmol) and 30% H₂O₂ (3 mL) in THF (10 mL) at rt. The mixture was heated at 50° C. for 2 h. When TLC showed no starting material left, the pH of the mixture was acidified to pH ca. 5 and extracted with EtOAc (50 mL×3). The organic layer was washed with brine, dried over MgSO₄, concentrated. The resulting residue was purified by silica gel chromatography eluted with EtOAc to give the product (150 mg, 51%), as a white solid. $^1$H NMR (300 Mhz, DMSO-d$_6$) δ ppm 2.44 (s, 3H), 3.11 (t, 4H, J=4.8 Hz), 3.71 (t, 4H, J=4.8 Hz), 5.60 (s, 2H), 6.31 (d, 1H, J=8.1 Hz), 7.16 (br s, 2H), 7.25 (t, 1H, J=8.1 Hz), 7.35 (d, 1H, J=1.8 Hz), 7.41 (d, 1H, J=1.8 Hz), 7.60 (d, 1H, J=8.1 Hz); LC-MS: m/e=419 [M+1]$^+$ d) 1-[(2,3-dichlorophenyl)methyl]-N-[(1E)-(dimethylamino)methylidene]-2-methyl-6-(4-morpholinyl)-1H-benzimidazole-4-carboxamide

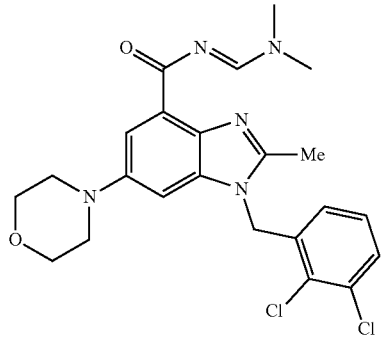 [SMILES: Cc1nc2c(C(=O)/N=C/N(C)C)cc(N3CCOCC3)cc2n1Cc1cccc(Cl)c1Cl]

A solution of combined batches of 11-[(2,3-dichlorophenyl)methyl]-2-methyl-6-(4-morpholinyl)-1H-benzimidazole-4-carboxamide (220 mg, 0.52 mmol) in DMF-DMA (15 ml) was stirred at 130° C. for 2 h. When TLC showed no starting material remaining, the mixture was cooled to rt and the solvent was removed under reduced pressure to give the crude product (JS211561-105A1, 220 mg, 89%), as a yellow solid. LC-MS: m/e=474 [M+1]$^+$ e) 1-[(2,3-dichlorophenyl)methyl]-2-methyl-6-(4-morpholinyl)-4-(1H-1,2,4-triazol-3-yl)-1H-benzimidazole Hydrazine monohydrate (2 mL) was added to a solution of 1-[(2,3-dichlorophenyl)methyl]-N-[(1E)-(dimethylamino)methylidene]-2-methyl-6-(4-morpholinyl)-1H-benzimidazole-4-carboxamide (220 mg, 0.46 mmol) in acetic acid (5 mL) and stirred at 130° C. for 20 min. The reaction mixture was cooled to rt and poured into saturated NaHCO$_3$ solution (15 mL). The mixture was extracted with DCM (30 mL×3). The combined organic layers were dried over MgSO$_4$, filtered and concentrated. The resulting residue was purified by silica gel chromatography eluted with DCM:MeOH=30:1 to give the desired product (110 mg, 53%), as a white solid. $^1$H NMR (300 MHz, DMSO-d$_6$) δ ppm 2.50 (s, 3H), 3.12 (t, 4H, J=4.8 Hz), 3.75 (t, 4H, J=4.8 Hz), 5.62 (s, 2H), 6.36 (d, 1H, J=8.1 Hz), 7.21 (s, 1H), 7.27 (t, 1H, J=8.1 Hz), 7.54 (s, 1H), 7.61 (d, 1H, J=8.1 Hz), 8.08 (s, 1H), 13.80 (s, 1H); LC-MS: m/e=443 [M+1]$^+$.

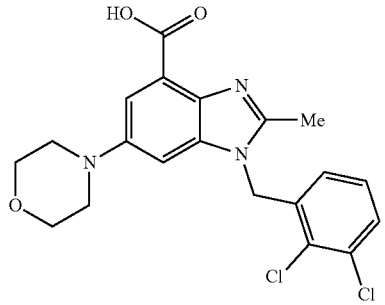 [SMILES: Cc1nc2c(C(=O)O)cc(N3CCOCC3)cc2n1Cc1cccc(Cl)c1Cl]

Preparation of 1-[(2,3-dichlorophenyl)methyl]-2-methyl-6-(4-morpholinyl)-1H-benzimidazole-4-carboxylic acid a) methyl 1-[(2,3-dichlorophenyl)methyl]-2-methyl-6-(4-morpholinyl)-1H-benzimidazole-4-carboxylate

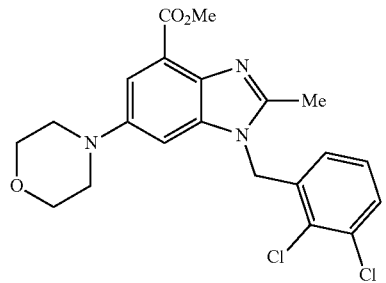 [SMILES: COC(=O)c1cc(N2CCOCC2)cc2c1nc(C)n2Cc1cccc(Cl)c1Cl]

A mixture of 4-bromo-1-[(2,3-dichlorophenyl)methyl]-2-methyl-6-(4-morpholinyl)-1H-benzimidazole (prepared following the same procedure as for Example 21, 150 mg, 0.33 mmol), dppf (18 mg, 0.033 mmol), Pd(AcO)$_2$ (14.8 mg, 0.066 mmol) and triethylamine (37 mg, 0.363 mmol) in methanol (30 mL), was degassed with CO(g). Then the reaction mixture was stirred at 60° C. for 4 h under a CO(g) atmosphere. The reaction mixture was cooled, concentrated. The resulting residue was purified by silica gel chromatography eluted with petroleum ether:EtOAc=1:1 to give the desired product (65 mg, 45%), as a white solid. $^1$H NMR (300 MHz, CDCl$_3$) δ 2.58 ppm (s, 3H), 3.16 (t, 4H, J=4.8 Hz), 3.86 (t, 4H, J=4.8 Hz), 4.07 (s, 3H), 5.38 (s, 2H), 6.24 (d, 1H, J=7.8 Hz), 6.77 (d, 1H, J=2.4 Hz), 7.03 (t, 1H, J=7.8 Hz), 7.42 (d, 1H, J=7.8 Hz), 7.67 (d, 1H, J=2.4 Hz); LC-MS: m/e=434 [M+1]$^+$ b) 1-[(2,3-dichlorophenyl)methyl]-2-methyl-6-(4-morpholinyl)-1H-benzimidazole-4-carboxylic acid A mixture of methyl 1-[(2,3-dichlorophenyl)methyl]-2-methyl-6-(4-morpholinyl)-1H-benzimidazole-4-carboxylate (65 mg, 0.15 mmol) and LiOH (19 mg, 0.5 mmol) in THF (5 mL) and water (5 mL), was stirred overnight at rt. Then the pH of the reaction mixture was neutralized with 1N aq. HCl. Then the mixture was stirred at rt for 1 h, filtered to give the product (47 mg, 74%, with about 10% monochloride as the impurity) as a white solid. $^1$H NMR (300 MHz, DMSO-d$_6$) δ ppm 2.53 (s, 3H), 3.12 (t, 4H, J=4.5 Hz), 3.73 (t, 4H, J=4.5 Hz), 5.66 (s, 2H), 6.42 (d, 1H, J=7.8 Hz), 7.26 (t, 1H, J=7.8 Hz), 7.42 (s, 1H), 7.48 (s, 1H), 7.62 (d, 1H, J=7.8 Hz); LC-MS: m/e=420 [M+1]$^+$

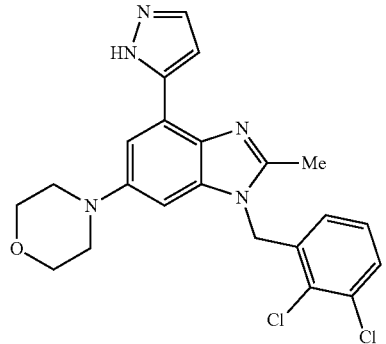 [SMILES: Cc1nc2c(-c3ccn[nH]3)cc(N3CCOCC3)cc2n1Cc1cccc(Cl)c1Cl]

Preparation of 1-[(2,3-dichlorophenyl)methyl]-2-methyl-6-(4-morpholinyl)-4-(1H-pyrazol-5-yl)-1H-benzimidazole A mixture of 4-bromo-1-[(2,3-dichlorophenyl)methyl]-2-methyl-6-(4-morpholinyl)-1H-benzimidazole (prepared following the same procedure as for Example 21, 250 mg, 0.55 mmol), 1H-pyrazol-5-ylboronic acid (64 mg, 0.57 mmol), Pd(dba)$_2$ (32 mg, 0.055 mmol), Cs$_2$CO$_3$ (358 mg, 1.1 mmol) and P(t-Bu)$_3$ (10 wt % in hexane, 110 mg, 0.055 mmol) in dioxane (16 mL) and water (8 mL), was stirred at 80° C. for 3 h under a nitrogen atmosphere. The reaction mixture was cooled and then concentrated. The resulting residue was purified by silica gel chromatography eluted with petroleum ether:EtOAc=1:1 to give the crude product (122 mg). The crude product was purified by Prep-HPLC to the pure product (72 mg, 30%), as a white solid. $^1$H NMR showed this compound is in a form of tautomeric mixture (major tautomer/minor tautomer=5/3) $^1$H NMR of the major tautomer (300 MHz, DMSO-d$_6$) δ ppm 2.46 (s, 3H), 3.12-3.14 (m, 4H), 3.73-3.76 (m, 4H), 5.57 (s, 2H), 6.36 (d, 1H, J=7.8 Hz), 6.97 (s, 1H), 7.20-7.28 (m, 2H), 7.37 (s, 1H), 7.53-7.61 (m, 2H), 13.17 (s, 1H); LC-MS: m/e=442 [M+1]$^+$

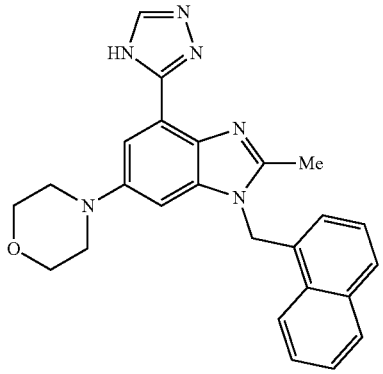

Preparation of 2-methyl-6-(4-morpholinyl)-1-(1-naphthalenylmethyl)-4-(1H-1,2,4-triazol-3-yl)-1H-benzimidazole a) 2-methyl-6-(4-morpholinyl)-1-(1-naphthalenylmethyl)-1H-benzimidazole-4-carboxamide

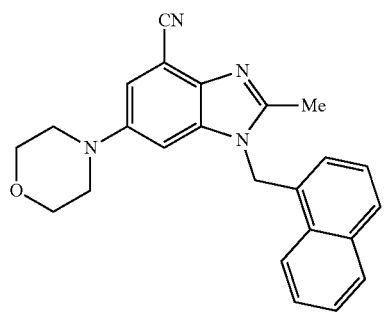 [SMILES: Cc1nc2c(C#N)cc(N3CCOCC3)cc2n1Cc1cccc2ccccc12]

Preparation of 2-methyl-6-(4-morpholinyl)-1-(1-naphthalenylmethyl)-1H-benzimidazole-4-carbonitrile A mixture of 4-bromo-2-methyl-6-(4-morpholinyl)-1-(1-naphthalenylmethyl)-1H-benzimidazole (prepared following the same procedure as for Example 19, 300 mg, 0.69 mmol), Pd(PPh3)4 (80 mg, 0.069 mmol) and Zn(CN)$_2$ (162 mg, 1.38 mmol) in DMF (30 mL) was stirred at 80° C. under N$_2$ for 18 h. After cooling to rt, the mixture was poured into water and filtered. The filter cake was purified by silica gel chromatography eluted with petroleum ether:EtOAc=1:1 to give the product (180 mg, 68%), as a white solid. $^1$H NMR (300 MHz, DMSO-d$_6$): δ 2.44 (s, 3H), 3.07 (t, 4H, J=4.5 Hz), 3.68 (t, 4H, J=4.5 Hz), 6.04 (s, 2H), 6.32 (d, 1H, J=7.2 Hz), 7.31-7.40 (m, 3H), 7.60-7.71 (m, 2H), 7.86 (d, 1H, J=8.4 Hz), 8.01 (d, 1H, J=7.2 Hz), 8.22 (d, 1H, J=8.4 Hz); LC-MS: m/e=383 [M+1]$^+$

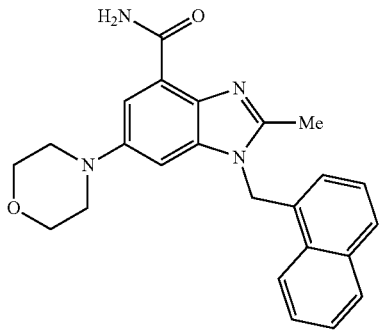 [SMILES: Cc1nc2c(C(N)=O)cc(N3CCOCC3)cc2n1Cc1cccc2ccccc12]

A solution of KOH (45 mg, 0.8 mmol) in water (10 mL) was added dropwise to solution of 2-methyl-6-(4-morpholinyl)-1-(1-naphthalenylmethyl)-1H-benzimidazole-4-carbonitrile (prepared using the same procedure as Example 24, 150 mg, 0.4 mmol) and 30% H$_2$O$_2$ (3 ml) in THF (15 mL) at rt. The mixture was heated to 35° C. for 1 h. When TLC showed no starting material remaining, water (50 mL) was added, then it was filtered. The filter cake was purified by silica gel chromatography eluted with petroleum ether:EtOAc=1:2 to give the product (115 mg, 72%), as a white solid. $^1$H NMR (300 MHz, DMSO-d$_6$): δ ppm 2.47 (s, 3H), 3.05 (t, 4H, J=4.8 Hz), 3.69 (t, 4H, J=4.8 Hz), 6.05 (s, 2H), 6.34 (d, 1H, J=7.2 Hz), 7.25 (d, 1H, J=2.4 Hz), 7.34 (t, 1H, J=7.8 Hz), 7.53 (d, 1H, J=2.4 Hz), 7.63-7.70 (m, 2H), 7.77 (d, 1H, J=3.0 Hz), 7.86 (d, 1H, J=8.1 Hz), 8.01 (d, 1H, J=7.2 Hz), 8.24 (d, 1H, J=8.1 Hz), 9.24 (d, 1H, J=3.0 Hz); LC-MS: m/e=401 [M+1]$^+$ b) N-[(1E)-(dimethylamino)methylidene]-2-methyl-6-(4-morpholinyl)-1-(1-naphthalenylmethyl)-1H-benzimidazole-4-carboxamide

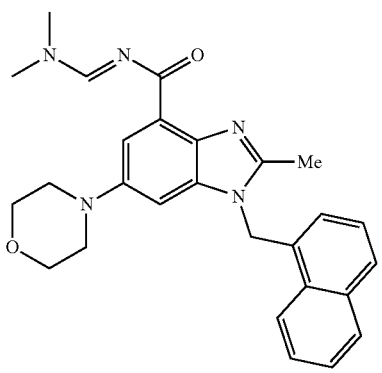 [SMILES: Cc1nc2c(C(=O)/N=C/N(C)C)cc(N3CCOCC3)cc2n1Cc1cccc2ccccc12]

A solution of combined batches of 2-methyl-6-(4-morpholinyl)-1-(1-naphthalenylmethyl)-1H-benzimidazole-4-carboxamide (150 mg, 0.38 mmol) in DMF-DMA (10 mL) was stirred at 130° C. for 2 h. When TLC showed no starting material remaining, the mixture was cooled to rt and the solvent was removed under reduced pressure to give the crude product (130 mg, 76%), as a yellow solid. $^1$H NMR (300 MHz, DMSO-$d_6$): δ ppm 2.39 (s, 3H), 3.02 (t, 4H, J=4.5 Hz), 3.13 (s, 3H), 3.20 (s, 3H), 3.69 (t, 4H, J=4.5 Hz), 5.99 (s, 2H), 6.30 (d, 1H, J=7.8 Hz), 7.12 (d, 1H, J=2.4 Hz), 7.33 (t, 1H, J=7.8 Hz), 7.54 (d, 1H, J=2.4 Hz), 7.60-7.71 (m, 2H), 7.85 (d, 1H, J=7.8 Hz), 8.01 (d, 1H, J=7.8 Hz), 8.25 (d, 1H, J=7.8 Hz), 8.54 (s, 1H); LC-MS: m/e=456 [M+1]$^+$ c) 2-methyl-6-(4-morpholinyl)-1-(1-naphthalenylmethyl)-4-(1H-1,2,4-triazol-3-yl)-1H-benzimidazole Hydrazine hydrate (3 mL) was added to a solution of N-[(1E)-(dimethylamino)methylidene]-2-methyl-6-(4-morpholinyl)-1-(1-naphthalenylmethyl)-1H-benzimidazole-4-carboxamide (130 mg, 0.29 mmol) in acetic acid (10 mL) and stirred at 130° C. for 30 min. The reaction mixture was cooled to rt and poured into saturated Na$_2$CO$_3$ solution (20 mL). A filtration was performed, and the filter cake was purified by silica gel chromatography eluted with EtOAc to give the product (88 mg, 72%), as a white solid. $^1$H NMR (300 MHz, DMSO-$d_6$): δ ppm 2.50 (s, 3H), 3.09 (s, 4H), 3.71 (s, 4H), 6.06 (s, 2H), 6.37 (d, 1H, J=7.8 Hz), 7.20 (s, 1H), 7.34 (t, 1H, J=7.8 Hz), 7.54 (s, 1H), 7.61-7.72 (m, 2H), 7.86 (d, 1H, J=8.4 Hz), 8.02 (d, 1H, J=7.8 Hz), 8.09 (s, 1H), 8.25 (d, 1H, J=8.4 Hz), 13.85 (s, 1H); LC-MS: m/e=425 [M+1]$^+$

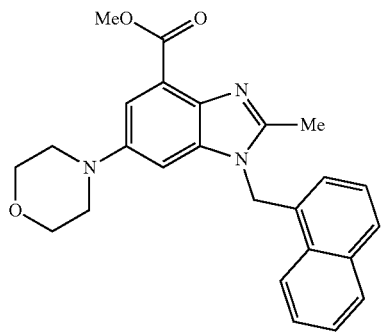 [SMILES: COC(=O)c1cc(N2CCOCC2)cc2c1nc(C)n2Cc1cccc2ccccc12]

Preparation of methyl 2-methyl-6-(4-morpholinyl)-1-(1-naphthalenylmethyl)-1H-benzimidazole-4-carboxylate a) 3-amino-5-chloro-2-nitrobenzoic acid

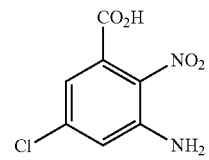

Under nitrogen, to a solution of t-BuOK (156.8 g) and Cu(OAc)$_2$ (3.6 g) in DMF (1.2 L) was added a solution of 5-chloro-2-nitrobenzoic acid (40.0 g) and MeONH$_2$HCl (33.2 g) in DMF (300 mL) at 0° C. After 3 h the reaction was quenched by addition of H$_2$O (2.5 L) and acidified with 10% HCl solution to pH=1. The mixture was extracted with EA (2 L×2) and the combined organic layers were then washed with brine, dried over anhydrous Na$_2$SO$_4$, filtered and concentrated in-vacuo to afford the crude product as a yellow solid (43.2 g, yield 100%). $^1$H NMR (300 MHz, CDCl$_3$): δ ppm 6.88 (s, 1H, J=2.4 Hz), 6.91 (d, 1H, J=2.4 Hz), 8.08 (br s, 2H); LC-MS: m/e=217 [M+1]$^+$.

b) methyl 3-amino-5-chloro-2-nitrobenzoate

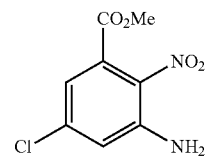 [SMILES: COC(=O)c1cc(Cl)cc(N)c1[N+](=O)[O-]]

A mixture of 3-amino-5-chloro-2-nitrobenzoic acid (43.2 g) and HATU (2-(1H-7-Azabenzotriazol-1-yl)-1,1,3,3-tetramethyl uronium hexafluorophosphate Methanaminium, commercially available) (76 g) in MeOH (81 mL), Et$_3$N (83 mL) and THF (300 mL) was stirred at room temperature for 3 h. When TLC showed no starting material, the solvent was removed in-vacuo and the residue was then diluted with EtOAc (2 L). It was then washed with brine (1 L×3) and dried over anhydrous Na$_2$SO$_4$, filtered and concentrated in-vacuo. The residue was then purified by silica gel chromatography eluted with EtOAc:petroleum ether=1:8 to afford the desired product as a yellow solid (29.5 g, yield 64%). $^1$H NMR (300 MHz, CDCl$_3$): δ ppm 3.90 (s, 3H, s), 5.85 (br s, 2H), 6.80 (d, 1H, J=2.4 Hz), 6.90 (d, 1H, J=2.4 Hz); LC-MS: m/e=231 [M+1]$^+$.

c) methyl 3-amino-5-(4-morpholinyl)-2-nitrobenzoate

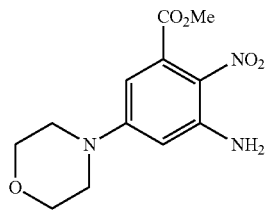 [SMILES: COC(=O)c1cc(N2CCOCC2)cc(N)c1[N+](=O)[O-]]

A mixture of combined batches of methyl 3-amino-5-chloro-2-nitrobenzoate (39 g), morpholine (29.5 g) and K$_2$CO$_3$ (47 g) was stirred in DMF (200 ml) at 110° C. for 5 h.

The mixture was cooled to room temperature and poured into water (1 L). It was extracted with EtOAc (500 mL×3). The combined organic layers were washed with brine, dried over anhydrous Na$_2$SO$_4$, filtered and concentrated in-vacuo to afford the desired product as a yellow solid (22 g, yield 46%). $^1$H NMR (300 MHz, CDCl$_3$): δ ppm 3.31 (t, 4H, J=4.8 Hz), 3.82 (t, 4H, J=4.8 Hz), 3.89 (s, 3H), 6.03 (d, 1H, J=2.4 Hz), 6.34 (d, 1H, J=2.4 Hz); LC-MS: m/e=282 [M+1]$^+$.

d) methyl 2-methyl-5-(4-morpholinyl)-1H-benzimidazole-7-carboxylate

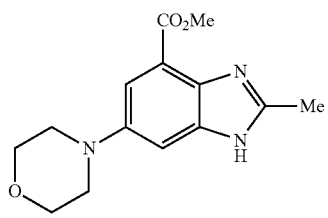 [SMILES: COC(=O)c1cc(N2CCOCC2)cc2[nH]c(C)nc12]

To a solution of methyl 3-amino-5-(4-morpholinyl)-2-nitrobenzoate (22 g) stirring at reflux in HOAc (400 mL) was added iron powder in portions (13 g). After the addition, the mixture was stirred at reflux for 5 h. It was cooled to room temperature and the solvent was removed in-vacuo. The residue was neutralized with aqueous Na$_2$CO$_3$ solution (1 L). It was extracted with EtOAc (500 mL×3). The combined organic layers were then concentrated in-vacuo and the residue was purified by silica gel chromatography eluted with MeOH:DCM=1:30 to afford the desired product as a solid (16.6 g, yield 77%). $^1$H NMR (300 MHz, CDCl$_3$): δ ppm 2.67 (s, 3H), 3.17 (t, 4H, J=4.8 Hz), 3.90 (t, 4H, J=4.8 Hz), 3.98 (s, 3H), 7.44 (d, 1H, J=1.8 Hz), 7.54 (d, 1H, J=1.8 Hz); LC-MS: m/e=276 [M+1]$^+$.

e) methyl 2-methyl-6-(4-morpholinyl)-1-(1-naphthalenylmethyl)-1H-benzimidazole-4-carboxylate A mixture of methyl 2-methyl-5-(4-morpholinyl)-1H-benzimidazole-7-carboxylate (4.125 g), 1-(bromomethyl)naphthalene (5 g) and K$_2$CO$_3$ (6.2 g) was stirred at 80° C. for 3 h. When TLC showed no starting material remaining, the mixture was cooled to room temperature and then poured into water (500 mL). It was extracted with EtOAc (500 mL×3) and the combined organic layers were washed with brine (500 mL×3) and then concentrated in-vacuo. The residue was purified by silica gel chromatography eluted with MeOH:DCM=1:100 to afford the desired product as a yellow solid (4.6 g, 74%). $^1$H NMR (300 MHz, DMSO-d$_6$): δ ppm 2.42 (s, 3H), 3.04 (t, 4H, J=4.8 Hz), 3.68 (t, 4H, J=4.8 Hz), 3.90 (s, 3H), 6.02 (s, 1H), 6.28 (d, 1H, J=7.5 Hz), 7.29 (d, 1H, J=2.4 Hz), 7.32 (d, 1H, J=7.5 Hz), 7.39 (d, 1H, J=2.4), 7.60-7.71 (m, 2H), 7.84 (d, 1H, J=8.4 Hz), 8.01 (d, 1H, J=7.5 Hz), 8.24 (d, 1H, J=7.5 Hz); LC-MS: m/e=416 [M+1]$^+$.

Example 27

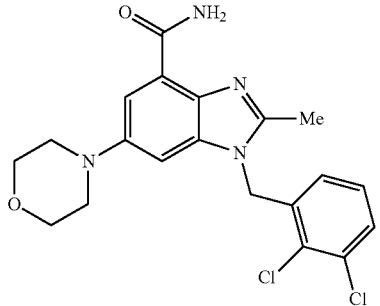 [SMILES: Cc1nc2c(C(N)=O)cc(N3CCOCC3)cc2n1Cc1cccc(Cl)c1Cl]

Preparation of 11-[(2,3-dichlorophenyl)methyl]-2-methyl-6-(4-morpholinyl)-1H-benzimidazole-4-carboxamide The titled compound was prepared from 1-[2,3-dichlorophenyl)methyl]-2-methyl-6-(4-morpholinyl)-1H-benzimidazole-4-carbonitrile using the same procedure described in Example 21, step c. $^1$H NMR (300 Mhz, DMSO-d$_6$) δ ppm 2.44 (s, 3H), 3.11 (t, 4H, J=4.8 Hz), 3.71 (t, 4H, J=4.8 Hz), 5.60 (s, 2H), 6.31 (d, 1H, J=8.1 Hz), 7.16 (br s, 2H), 7.25 (t, 1H, J=8.1 Hz), 7.35 (d, 1H, J=1.8 Hz), 7.41 (d, 1H, J=1.8 Hz), 7.60 (d, 1H, J=8.1 Hz); LC-MS: m/e=419 [M+1]$^+$

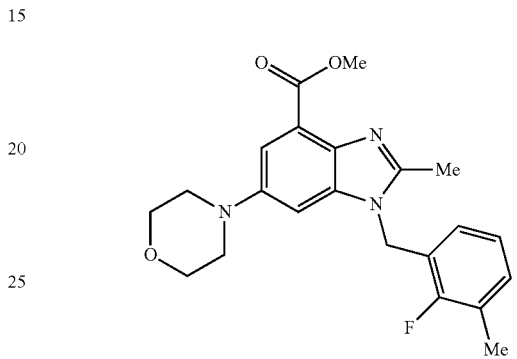

Preparation of methyl 1-[(2-fluoro-3-methylphenyl)methyl]-2-methyl-6-(4-morpholinyl)-1H-benzimidazole-4-carboxylate A mixture of methyl 2-methyl-5-(4-morpholinyl)-1H-benzimidazole-7-carboxylate prepared as described in Example 26, step d (500 mg, 1.82 mmol), K$_2$CO$_3$ (502 mg, 3.64 mmol) and 1-(bromomethyl)-2-fluoro-3-methylbenzene (389 mg, 1.91 mmol) in DMF (25 mL) was stirred at 80° C. for 18 h. The reaction mixture was cooled, poured into water (100 mL) and extracted with EtOAc (50 mL×3). The combined organic layers were dried over Na$_2$SO$_4$ and concentrated. The resulting residue was purified by silica gel chromatography eluted with EtOAc:MeOH=100:1 to give the desired product (350 mg, 48%) as a red solid. $^1$H NMR (300 MHz, DMSO-d$_6$): δ ppm 2.24 (d, 3H, J=1.8 Hz), 2.47 (s, 3H), 3.09 (t, 4H, J=4.8 Hz), 3.75 (t, 4H, J=4.8 Hz), 3.86 (s, 3H), 5.51 (s, 2H), 6.62 (t, 1H, J=7.5 Hz), 7.00 (t, 1H, J=7.5 Hz), 7.22 (t, 1H, J=7.5 Hz), 7.32 (d, 1H, J=2.4 Hz), 7.36 (d, 1H, J=2.4 Hz); LC-MS: m/e=398 [M+1]$^+$

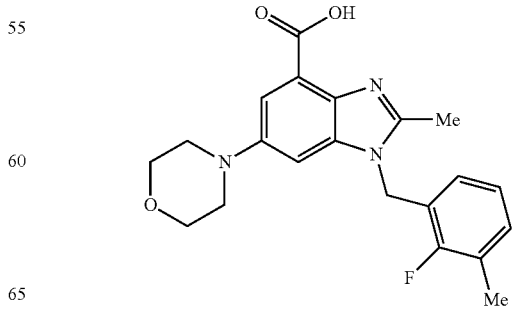

Preparation of 1-[(2-fluoro-3-methylphenyl)methyl]-2-methyl-6-(4-morpholinyl)-1H-benzimidazole-4-carboxylic acid A mixture of methyl 1-[(2-fluoro-3-methylphenyl)methyl]-2-methyl-6-(4-morpholinyl)-1H-benzimidazole-4-carboxylate, prepared as described in Example 28 (240 mg, 0.6 mmol) and 2 N LiOH (1.8 mL, 3.6 mmol) in THF (20 mL), was stirred at 45° C. for 16 h. The solution was filtered; the filter cake was then dissolved in water (20 mL) and added into formic acid to adjust the pH of the solution to 3-4. Then a filtration was performed to provide the product (160 mg, 70%), as a white solid. $^1$H NMR (300 MJz, DMSO-$d_6$): δ ppm 2.24 (d, 3H, J=1.8 Hz), 2.50 (s, 3H), 3.12 (t, 4H, J=4.8 Hz), 3.75 (t, 4H, J=4.8 Hz), 5.57 (s, 2H), 6.74 (t, 1H, J=7.5 Hz), 7.03 (t, 1H, J=7.5 Hz), 7.24 (t, 1H, J=7.5 Hz), 7.40 (d, 1H, J=2.4 Hz), 7.42 (d, 1H, J=2.4 Hz); LC-MS: m/e=384 [M+1]$^+$

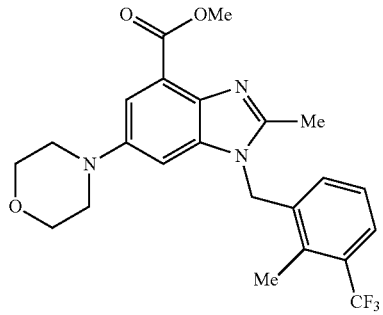 [SMILES: COC(=O)c1cc(N2CCOCC2)cc2c1nc(C)n2Cc1cccc(C(F)(F)F)c1C]

Preparation of methyl 2-methyl-1-{[2-methyl-3-(trifluoromethyl)phenyl]methyl}-6-(4-morpholinyl)-1H-benzimidazole-4-carboxylate A solution of methyl 2-methyl-5-(4-morpholinyl)-1H-benzimidazole-7-carboxylate prepared as described in Example 26, step d (500 mg, 1.8 mmol), 1-(bromomethyl)-2-methyl-3-(trifluoromethyl)benzene (483 mg, 1.9 mmol) and $K_2CO_3$ (497 mg, 3.6 mmol) in DMF (50 mL) was stirred at 80° C. for 3 h. The reaction mixture was cooled to rt and poured into water (50 mL), extracted with EtOAc (30 mL×3). The combined organic layers were washed with brine, dried over $Na_2SO_4$ and concentrated. The resulting residue was purified by silica gel chromatography eluted with DCM:MeOH=50:1 to give the crude product (230 mg, yield 29%), as a white solid. $^1$H NMR (300 MHz, DMSO-$d_6$): δ ppm 2.39 (s, 3H), 2.54 (s, 3H), 3.08 (t, 4H, J=4.8 Hz), 3.72 (t, 4H, J=4.8 Hz), 3.89 (s, 3H), 5.57 (s, 2H), 6.27 (d, 1H, J=7.5 Hz), 7.22 (t, 1H, J=7.5 Hz), 7.27 (d, 1H, J=2.4 Hz), 7.38 (d, 1H, J=2.4 Hz) 7.60 (d, 1H, J=7.5 Hz); LC-MS: m/e=448 [M+1]$^+$

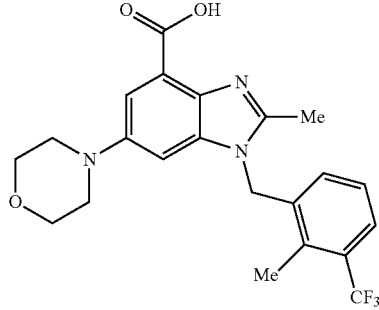

Preparation of 2-methyl-1-{[2-methyl-3-(trifluoromethyl)phenyl]methyl}-6-(4-morpholinyl)-1H-benzimidazole-4-carboxylic acid An aqueous solution of 2 N LiOH (1.2 mL) was added to a solution of methyl 2-methyl-1-{[2-methyl-3-(trifluoromethyl)phenyl]methyl}-6-(4-morpholinyl)-1H-benzimidazole-4-carboxylate, prepared as described in Example 30 (180 mg, 0.4 mmol) in THF (10 mL) and stirred at 50° C. for 1 h. When TLC showed no starting material remaining, the mixture was cooled to rt and THF was removed under reduced pressure. The pH of the mixture was acidified to pH 3. The suspension was filtered and the filtrate was collected, and washed with water (10 mL) to give the product as a white solid (152 mg, yield 88%). $^1$H NMR (300 MHz, DMSO-$d_6$): δ ppm 2.46 (s, 3H), 2.54 (s, 3H), 3.10 (t, 4H, J=4.8 Hz), 3.73 (t, 4H, J=4.8 Hz), 5.63 (s, 2H), 6.37 (d, 1H, J=7.8 Hz), 7.26 (t, 1H, J=7.8 Hz), 7.35 (d, 1H, J=2.4 Hz), 7.44 (d, 1H, J=2.4 Hz), 7.62 (d, 1H, J=7.8 Hz); LC-MS: m/e=434 [M+1]$^+$.

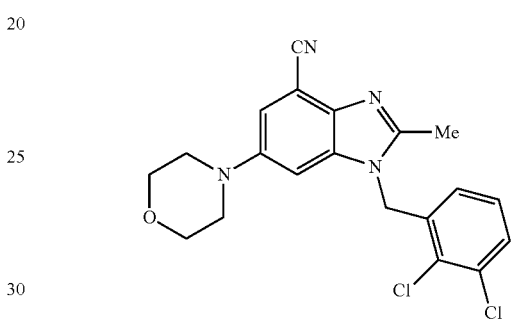

Preparation of 1-[(2,3-dichlorophenyl)methyl]-2-methyl-6-(4-morpholinyl)-1H-benzimidazole-4-carbonitrile The titled compound was prepared from 4-bromo-1-[(2,3-dichlorophenyl)methyl]-2-methyl-6-(4-morpholinyl)-1H-benzimidazole using the same procedure as described in Example 21, step b. $^1$H NMR (300 MHz, DMSO-$d_6$) δ ppm 2.43 (s, 3H), 3.11 (t, 4H, J=4.8 Hz), 3.72 (t, 4H, J=4.8 Hz), 5.60 (s, 2H), 6.30 (dd, 1H, J=1.2, 8.1 Hz), 7.25 (t, 1H, J=8.1 Hz), 7.35 (d, 1H, J=2.1 Hz), 7.42 (d, 1H, J=2.1 Hz), 7.60 (dd, 1H, J=1.2, 8.1 Hz); LC-MS: m/e=401 [M+1]$^+$.

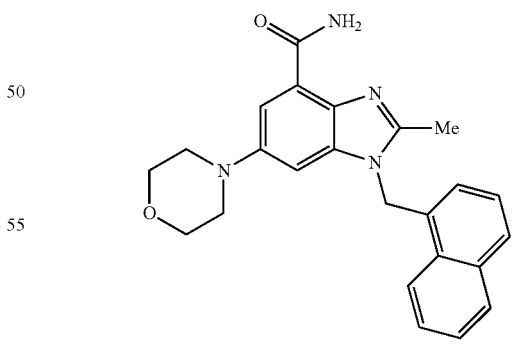

Preparation of 2-methyl-6-(4-morpholinyl)-1-(1-naphthalenylmethyl)-1H-benzimidazole-4-carboxamide To a solution of 2-methyl-6-(4-morpholinyl)-1-(1-naphthalenylmethyl)-1H-benzimidazole-4-carboxylic acid, prepared as described in Example 20 (100 mg) in DCM (20 mL) was added a drop of DMF. The solution was then cooled to 0° C. and then Oxalyl chloride (64 mg) was then added. The mixture was stirred at room temperature for 30 min. The solvent was removed in-vacuo to afford a white solid that used directly in the next step. To the solid dissolved in dry DCM (20 mL) was bubbled in NH₃ at 0° C. for 5 min. The mixture was then concentrated in-vacuo to afford the desired product as a white solid (79 mg, 79%). ¹H NMR (300 MHz, DMSO-$d_6$): δ ppm 2.47 (s, 3H), 3.05 (t, 4H, J=4.5 Hz), 3.69 (t, 4H, J=4.5 Hz), 6.05 (s, 2H), 6.35 (d, 1H, J=7.5 Hz), 7.23 (s, 1H), 7.34 (t, 1H, J=7.5 Hz), 7.53 (s, 1H), 7.60-7.74 (m, 3H), 7.86 (d, 1H, J=7.5 Hz), 8.01 (d, 1H, J=9.0 Hz), 8.24 (d, 1H, J=9.0 Hz), 9.22 (s, 1H); LC-MS: m/e=401 [M+1]⁺.

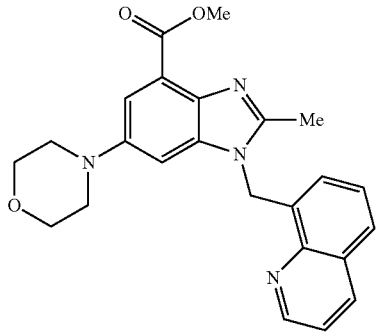 [SMILES: COC(=O)c1cc(N2CCOCC2)cc2c1nc(C)n2Cc1cccc2cccnc12]

Preparation of methyl 2-methyl-6-(4-morpholinyl)-1-(8-quinolinylmethyl)-1H-benzimidazole-4-carboxylate A mixture of methyl 2-methyl-5-(4-morpholinyl)-1H-benzimidazole-7-carboxylate, prepared as described in Example 26, step d (500 mg, 1.82 mmol), K₂CO₃ (502 mg, 3.64 mmol) and 5-(bromomethyl)quinoline (424 mg, 1.91 mmol) in DMF (25 mL) was stirred at 80° C. for 18 h. The reaction mixture was cooled, poured into water (100 mL) and extracted with EtOAc (50 mL×3). The combined organic layers were dried by Na₂SO₄ and concentrated. The resulting residue was purified by silica gel chromatography eluted with EtOAc: MeOH=100:1 to give the crude product (350 mg, 46%), finally it was purified by Prep-HPLC to give the product (180 mg, 24%) as a red solid. ¹H NMR (300 MHz, DMSO-$d_6$): δ ppm 2.52 (s, 3H), 3.03 (t, 4H, J=4.8 Hz), 3.70 (t, 4H, J=4.8 Hz), 3.88 (s, 3H), 6.08 (s, 2H), 6.87 (d, 1H, J=7.5 Hz), 7.31 (d, 1H, J=2.1 Hz), 7.36 (d, 1H, J=2.1 Hz), 7.48 (t, 1H, J=7.5 Hz), 7.66 (dd, 1H, J=4.2, 8.4 Hz), 7.93 (d, 1H, J=7.5 Hz), 8.44 (dd, 1H, J=1.8, 8.4 Hz), 9.05 (dd, 1H, J=1.8, 4.2 Hz); LC-MS: m/e=417 [M+1]⁺

Example 35

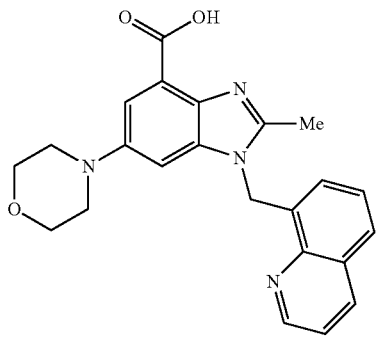 [SMILES: Cc1nc2c(C(=O)O)cc(N3CCOCC3)cc2n1Cc1cccc2cccnc12]

Preparation of 2-methyl-6-(4-morpholinyl)-1-(8-quinolinylmethyl)-1H-benzimidazole-4-carboxylic acid A mixture of methyl 2-methyl-6-(4-morpholinyl)-1-(8-quinolinylmethyl)-1H-benzimidazole-4-carboxylate, prepared as described in Example 34 (300 mg, 0.72 mmol) and 2 N LiOH (2.2 mL, 4.3 mmol) in THF (10 mL), was stirred at 45° C. for 16 h. It was filtered and the filter cake was dissolved in water (20 mL) and then added into formic acid to adjust the pH of the solution to 3-4. Then a filtration was performed to give the product (200 mg, 69%), as a white solid. ¹H NMR (300 MHz, DMSO-$d_6$): δ ppm 2.61 (s, 3H), 3.06 (t, 4H, J=4.8 Hz), 3.71 (t, 4H, J=4.8 Hz), 6.13 (s, 2H), 7.03 (d, 1H, J=7.5 Hz), 7.41 (s, 2H), 7.51 (t, 1H, J=7.5 Hz), 7.66 (dd, 1H, J=4.2, 8.4 Hz), 7.95 (d, 1H, J=7.5 Hz), 8.45 (dd, 1H, J=1.8, 8.4 Hz), 9.05 (dd, 1H, J=1.8, 4.2 Hz); LC-MS: m/e=403 [M+1]⁺

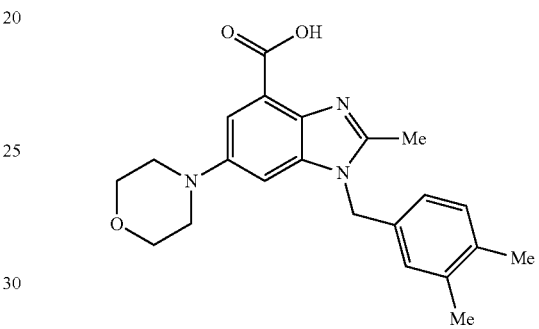

Preparation of 1-[(3,4-dimethylphenyl)methyl]-2-methyl-6-(4-morpholinyl)-1H-benzimidazole-4-carboxylic acid a) methyl 1-[(3,4-dimethylphenyl)methyl]-2-methyl-6-(4-morpholinyl)-1H-benzimidazole-4-carboxylate

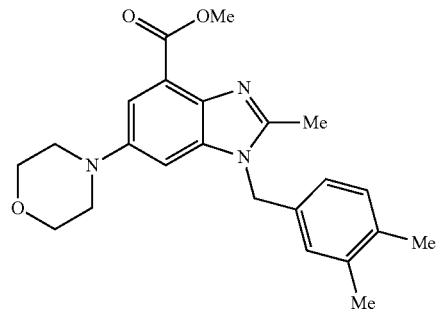 [SMILES: COC(=O)c1cc(N2CCOCC2)cc2c1nc(C)n2Cc1ccc(C)c(C)c1]

To a solution of methyl 2-methyl-5-(4-morpholinyl)-1H-benzimidazole-7-carboxylate prepared as described in Example 26, step d (0.22 g, 0.799 mmol) in N,N-Dimethylformamide (DMF) (10 mL) was added in 4-(chloromethyl)-1,2-dimethylbenzene (0.185 g, 1.199 mmol) and potassium carbonate (0.331 g, 2.397 mmol). The resulting reaction mixture was stirred at 80° C. for 3 h. It was cooled to room temperature and poured into water (30 mL). The mixture was extracted with EtOAc (50 mL×3). The combined organic phases were washed with brine (50 mL) and concentrated. The crude material was subjected to normal phase purification (0~40% EtOAc/Hexane) then (0~1% MeOH/DCM) to give the product (0.24 g, 76%). MS (ES+) m/e 394.0 [M+H]+.

b) 1-[(3,4-dimethylphenyl)methyl]-2-methyl-6-(4-morpholinyl)-1H-benzimidazole-4-carboxylic acid To a mixture of methyl 1-[(3,4-dimethylphenyl)methyl]-2-methyl-6-(4-morpholinyl)-1H-benzimidazole-4-carboxylate (0.24 g, 0.61 mmol) in Tetrahydrofuran (THF) (10 mL) was added in lithium hydroxide (5.99 mL, 11.99 mmol). The reaction was stirred at 50° C. for 2 h. The reaction was cooled to room temperature. The organic solvent was removed in-vacuo. The precipitate was collected by filtration. Water (20 mL) was added in. The mixture was acidified with 1 N HCl. The resulting solid was filtered and washed with water and dried to give the product (0.16 g, 66%). $^1$H NMR (400 MHz, DMSO-$d_6$) δ ppm 2.18 (s, 6H), 2.58-2.75 (s, 3H), 3.06-3.22 (m, 4H), 3.71-3.82 (m, 4H), 5.55 (s, 2H), 6.94 (m, 1H), 7.04 (s, 1H), 7.11 (d, 1H, J=7.83 Hz), 7.52 (m, 2H). MS (ES+) m/e 380.2[M+H]+

Example 37

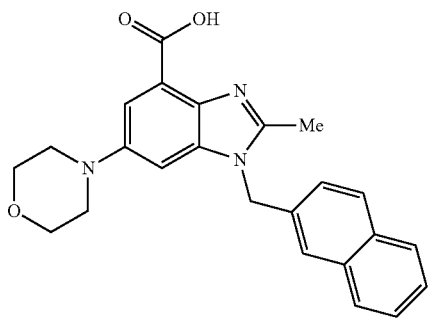 [SMILES: Cc1nc2c(C(=O)O)cc(N3CCOCC3)cc2n1Cc1ccc2ccccc2c1]

Preparation of 2-methyl-6-(4-morpholinyl)-1-(2-naphthalenylmethyl)-1H-benzimidazole-4-carboxylic acid The titled compound was prepared following the same procedure as Example 36 replacing 4-(chloromethyl)-1,2-dimethylbenzene with 2-(bromomethyl)naphthalene in the first step. $^1$H NMR (400 MHz, DMSO-$d_6$) δ ppm 2.73 (br. s., 3H), 3.11-3.21 (m, 4H), 3.70-3.78 (m, 4H), 5.82 (br. s., 2H), 7.40 (d, J=7.83 Hz, 1H), 7.48-7.63 (m, 4H), 7.72 (s, 1H), 7.82-7.97 (m, 3H). MS (ES+) m/e 401.9 [M+H]+.

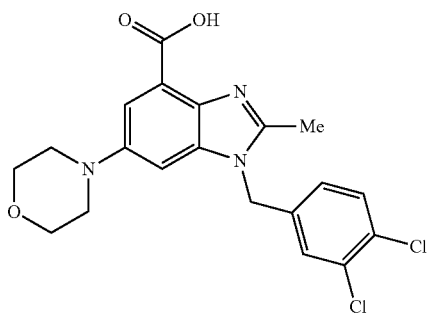 [SMILES: Cc1nc2c(C(=O)O)cc(N3CCOCC3)cc2n1Cc1ccc(Cl)c(Cl)c1]

Preparation of 1-[(3,4-dichlorophenyl)methyl]-2-methyl-6-(4-morpholinyl)-1H-benzimidazole-4-carboxylic acid The titled compound was prepared following the same procedure as Example 36 replacing 4-(chloromethyl)-1,2-dimethylbenzene with 4-(bromomethyl)-1,2-dichlorobenzene in the first step. $^1$H NMR (400 MHz, DMSO-$d_6$) δ ppm 2.55 (s, 3H), 3.00-3.18 (m, 4H), 3.61-3.83 (m, 4H), 5.56 (s, 2H), 7.02 (dd, J=8.34, 2.02 Hz, 1H), 7.44 (s, 2H), 7.50 (d, J=2.02 Hz, 1H), 7.60 (d, 1H). MS (ES+) m/e 420.2 [M+H]+

Example 39

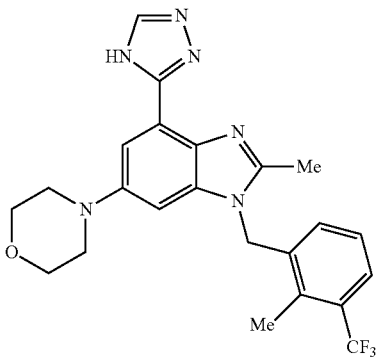 [SMILES: Cc1c(Cn2c(C)nc3c(-c4nnc[nH]4)cc(N4CCOCC4)cc32)cccc1C(F)(F)F]

Preparation of 2-methyl-1-{[2-methyl-3-(trifluoromethyl)phenyl]methyl}-6-(4-morpholinyl)-4-(1H-1,2,4-triazol-3-yl)-1H-benzimidazole a) 2-methyl-1-{[2-methyl-3-(trifluoromethyl)phenyl]methyl}-6-(4-morpholinyl)-1H-benzimidazole-4-carboxamide

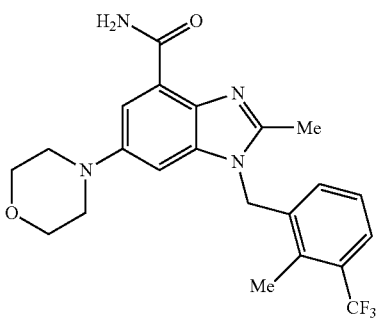 [SMILES: Cc1c(Cn2c(C)nc3c(C(N)=O)cc(N4CCOCC4)cc32)cccc1C(F)(F)F]

To the mixture of 2-methyl-1-{[2-methyl-3-(trifluoromethyl)phenyl]methyl}-6-(4-morpholinyl)-1H-benzimidazole-4-carboxylic acid, prepared as described in Example 31 (0.6 g, 1.384 mmol) in Dichloromethane (DCM) (60 mL) was added in oxalyl chloride (0.485 mL, 5.54 mmol) and followed by the addition of ten drops of DMF. The reaction mixture was stirred at rt for 10 minutes and concentrated to give the acid chloride. To a mixture of the crude acid chloride in Tetrahydrofuran (THF) (60 mL) was bubbled with NH$_3$ gas. The reaction was stirred at rt for 10 minutes. Brine (20 mL) and EtOAc (60 mL) was added in and the aqueous phase was extracted with EtOAc (60 mL). The organic phase was combined and concentrated (0.59 g, 99%). The crude product was used in the next step. MS (ES+) m/e 433.1 [M+H]+ b) 2-methyl-1-{[2-methyl-3-(trifluoromethyl)phenyl]methyl}-6-(4-morpholinyl)-4-(1H-1,2,4-triazol-3-yl)-1H-benzimidazole A mixture of 2-methyl-1-{[2-methyl-3-(trifluoromethyl)phenyl]methyl}-6-(4-morpholinyl)-1H-benzimidazole-4-carboxamide (0.52 g, 1.202 mmol) in N,N-dimethylformamide dimethyl acetal (30 mL, 224 mmol) was stirred at 105° C. for 2 hours and the reaction is complete. The reaction was concentrated under reduced pressure. To the crude material was added Acetic Acid (30 mL) and hydrazine monohydrate (0.264 mL, 8.42 mmol). The reaction mixture was stirred at 100° C. for 1 h and concentrated. The crude was purified using silica gel (0~2% MeOH/DCM) to give the product (0.245 g, 42%). $^1$H NMR (400 MHz, DMSO-$d_6$) δ ppm 2.48 (s, 3H), 2.56 (s, 3H), 3.10-3.15 (m, 4H), 3.67-3.79 (m, 4H), 5.62 (s, 2H), 6.37 (d, J=7.83 Hz, 1H), 7.19 (d, J=2.02 Hz, 1H), 7.26 (t, J=7.83 Hz, 1H), 7.55 (d, J=1.77 Hz, 1H), 7.62 (d, J=7.58 Hz, 1H), 8.09 (s, 1H), 13.83 (s, 1H). MS (ES+) m/e 457.1[M+H]+.

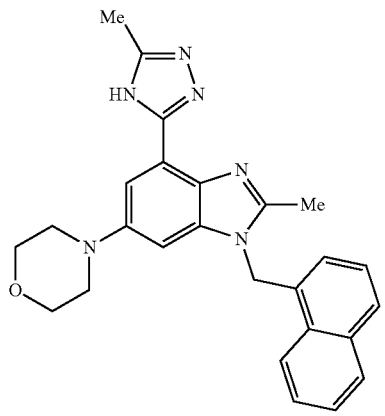 [SMILES: Cc1nnc(-c2cc(N3CCOCC3)cc3c2nc(C)n3Cc2cccc3ccccc23)[nH]1]

Preparation of 2-methyl-4-(3-methyl-1H-1,2,4-triazol-5-yl)-6-(4-morpholinyl)-1-(1-naphthalenylmethyl)-1H-benzimidazole a) 2-methyl-6-(4-morpholinyl)-1-(1-naphthalenylmethyl)-1H-benzimidazole-4-carbonitrile

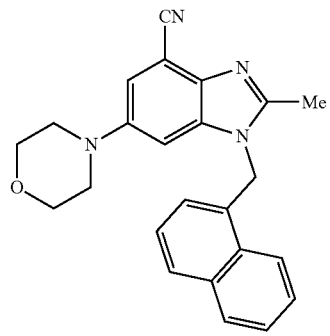 [SMILES: Cc1nc2c(C#N)cc(N3CCOCC3)cc2n1Cc1cccc2ccccc12]

To the mixture of 2-methyl-6-(4-morpholinyl)-1-(1-naphthalenylmethyl)-1H-benzimidazole-4-carboxamide, prepared as described in Example 33 (0.4 g, 0.999 mmol) in Dichloromethane (DCM) (50 mL) was added in POCl$_3$ (0.931 mL, 9.99 mmol) and followed by the addition of ten drops of DMF. The reaction was stirred at rt for 1 h. The mixture was quenched with aqueous sodium bicarbonate solution. The aqueous phase was extracted with DCM (100 mL). The combined organic phase was washed with Brine then dried (MgSO$_4$), filtered and the solvent removed invacuo. The crude was purified on silica (20~50% EtOAc/Hexane) to give the product (0.246 g, 64%). $^1$H NMR (400 MHz, DMSO-$d_6$) δ ppm 2.45 (s, 3H), 2.96-3.15 (m, 4H), 3.62-3.72 (m, 4H), 6.05 (s, 2H), 6.32 (d, J=7.07 Hz, 1H), 7.29-7.44 (m, 3H), 7.57-7.74 (m, 2H), 7.86 (d, J=8.08 Hz, 1H), 8.02 (d, J=7.83 Hz, 1H) 8.22 (d, 1H). MS (ES+) m/z 383.2 [M+H]+.

b) 2-methyl-4-(3-methyl-1H-1,2,4-triazol-5-yl)-6-(4-morpholinyl)-1-(1-naphthalenylmethyl)-1H-benzimidazole To the suspension of 2-methyl-6-(4-morpholinyl)-1-(1-naphthalenylmethyl)-1H-benzimidazole-4-carbonitrile (120 mg, 0.314 mmol) in n-butanol (15 mL) was added in acetic hydrazide (232 mg, 3.14 mmol) and potassium carbonate (434 mg, 3.14 mmol). The reaction was stirred at reflux temperature for 4 days. DCM (50 mL) and water (50 mL) were added in. The organic phase was washed with Brine (50 mL×3), dried (MgSO$_4$), and the solvent was removed. The crude was purified by reverse phase purification to provide the desired product (36 mg, 25%). $^1$H NMR (400 MHz, DMSO-$d_6$) δ ppm 1.71 (br. s., 3H), 1.78 (br. s., 3H), 2.21-2.37 (m, 4H), 2.90-3.08 (m, 4H), 5.20 (s, 2H), 5.74 (d, J=7.33 Hz, 1H), 6.17 (br. s., 1H), 6.51 (t, J=7.71 Hz, 1H), 6.75-6.95 (m, 3H), 7.04 (d, J=8.08 Hz, 1H), 7.17 (d, J=8.08 Hz, 1H), 7.43 (d, 1H). MS (ES+) m/e 439.1[M+H]+.

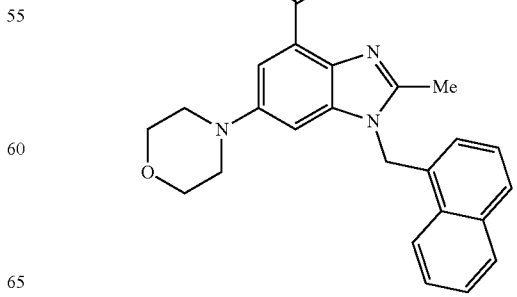

Preparation of 1-[2-methyl-6-(4-morpholinyl)-1-(1-naphthalenylmethyl)-1H-benzimidazol-4-yl]ethanone a) N,2-dimethyl-N-(methyloxy)-6-(4-morpholinyl)-1-(1-naphthalenylmethyl)-1H-benzimidazole-4-carboxamide

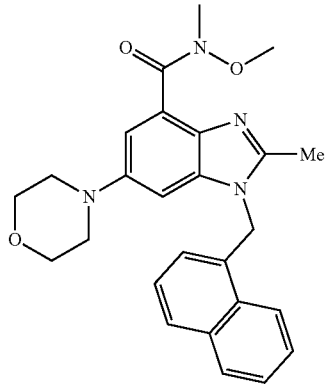 [SMILES: CON(C)C(=O)c1cc(N2CCOCC2)cc2c1nc(C)n2Cc1cccc2ccccc12]

To the suspension of 2-methyl-6-(4-morpholinyl)-1-(1-naphthalenylmethyl)-1H-benzimidazole-4-carboxylic acid, prepared as described in Example 20 (200 mg, 0.498 mmol) in dichloromethane (DCM) (30 mL) was added in oxalyl chloride (0.218 mL, 2.491 mmol) and followed by ten drops of DMF. The reaction mixture was stirred at rt for 10 min. The reaction mixture was concentrated under reduced pressure to give the acid chloride. To the mixture of the acid chloride in dichloromethane (DCM) (30 mL) was added in N,O-dimethylhydroxylamine hydrochloride (97 mg, 0.996 mmol) and TEA (0.694 mL, 4.98 mmol). The reaction mixture was stirred at rt for 18 h. Water (50 mL) was added in and the aqueous phase was extracted with DCM (50 mL×2). The combined organic phase was washed with Brine (50 mL), dried (MgSO$_4$) and concentrated under reduced pressure. The crude was purified on a silica column purification (0~4% MeOH/DCM) to give the product (100 mg, 43%). $^1$H NMR (400 MHz, DMSO-d$_6$) δ ppm 2.39 (s, 3H), 2.92-3.10 (m, 4H), 3.26 (br. s., 3H), 3.56-3.75 (m, 7H), 5.99 (s, 2H), 6.35 (d, J=6.57 Hz, 1H), 6.86 (d, J=2.02 Hz, 1H), 7.04 (d, J=1.77 Hz, 1H), 7.26-7.40 (m, 1H), 7.54-7.73 (m, 2H), 7.86 (d, J=8.34 Hz, 1H), 8.02 (d, J=7.07 Hz, 1H), 8.25 (d, 1H). MS (ES+) m/e 445.2[M+H]$^+$.

b) 1-[2-methyl-6-(4-morpholinyl)-1-(1-naphthalenylmethyl)-1H-benzimidazol-4-yl]ethanone To a solution of N,2-dimethyl-N-(methyloxy)-6-(4-morpholinyl)-1-(1-naphthalenylmethyl)-1H-benzimidazole-4-carboxamide (82 mg, 0.184 mmol) in Tetrahydrofuran (THF) (10 mL) was added a 3.0 M solution of methylmagnesium chloride (0.123 mL, 0.369 mmol) in THF at 0° C. The resulting reaction mixture was stirred at 0° C. for 2 h and then quenched very carefully with saturated aqueous ammonium chloride. The mixture was diluted with ethyl acetate (50 mL) and the aqueous phase was extracted with ethyl acetate (50 mL×2). The combined organic phases were washed with brine (50 mL), dried over (MgSO$_4$), and filtered. The solution was concentrated under reduced pressure. The crude product was purified on a silica column (40~60% EtOAc/Hexane) to give the product (46 mg, 59%). $^1$H NMR (400 MHz, DMSO-d$_6$) δ ppm 2.47 (s, 3H), 3.00 (s, 3H), 3.02-3.10 (m, 4H), 3.59-3.73 (m, 4H), 6.06 (s, 2H), 6.33 (d, J=6.82 Hz, 1H), 7.21-7.42 (m, 3H), 7.52-7.76 (m, 2H), 7.86 (d, J=8.34 Hz, 1H), 8.02 (d, J=7.33 Hz, 1H), 8.25 (d, 1H). MS (ES+) m/e 399.9[M+H]$^+$.

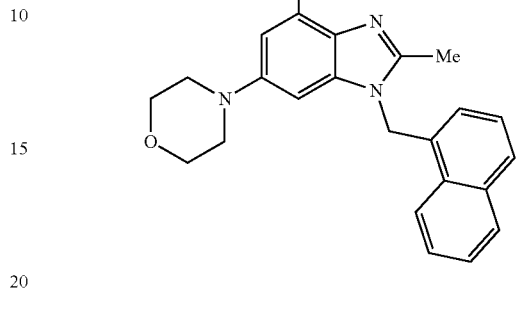

Preparation of [2-methyl-6-(4-morpholinyl)-1-(1-naphthalenylmethyl)-1H-benzimidazol-4-yl]methanol To the mixture of 2-methyl-6-(4-morpholinyl)-1-(1-naphthalenylmethyl)-1H-benzimidazole-4-carboxylic acid, prepared as described in Example 20 (70 mg, 0.174 mmol) in Tetrahydrofuran (THF) (5 mL) was added in LiAlH$_4$ (19.85 mg, 0.523 mmol) at 0° C. and the reaction mixture was stirred at rt for 1 h. Then LiAlH$_4$ (19.85 mg, 0.523 mmol) was added in and the reaction mixture was stirred at rt for another hour. The reaction mixture was cooled to 0° C. and quenched with water (0.04 ml), NaOH (15%, 0.04 ml) then water (0.12 ml). After the resultant mixture was stirred at room temperature for 2 h, anhydrous MgSO$_4$ was added and the reaction mixture was filtered through celite and washed with EtOAc. Evaporation of the solvent gave the crude product. The crude product was purified on a silica column (0-4% MeOH/DCM) to give the solid (12 mg, 17%). $^1$H NMR (400 MHz, DMSO-d$_6$) δ ppm 2.38 (s, 3H), 2.91-3.05 (m, 4H), 3.64-3.74 (m, 4H), 4.89 (d, J=5.56 Hz, 2H), 5.12 (t, J=5.81 Hz, 1H), 5.95 (s, 2H), 6.33 (d, J=6.82 Hz, 1H), 6.81 (d, J=2.02 Hz, 1H), 6.97 (d, J=1.77 Hz, 1H), 7.34 (t, J=7.71 Hz, 1H), 7.54-7.74 (m, 2H), 7.85 (d, J=8.08 Hz, 1H), 8.01 (d, J=7.58 Hz, 1H), 8.25 (d, 1H). MS (ES+) m/z 388.0 [M+H]$^+$.

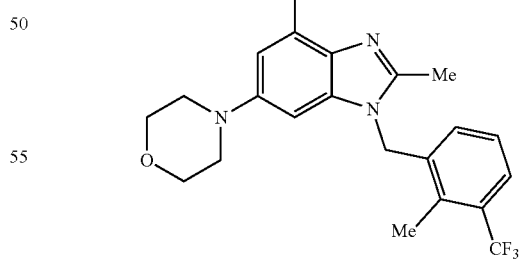

Preparation of [2-methyl-1-{[2-methyl-3-(trifluoromethyl)phenyl]methyl}-6-(4-morpholinyl)-1H-benzimidazol-4-yl]methanol A solution of methyl 2-methyl-1-{[2-methyl-3-(trifluoromethyl)phenyl]methyl}-6-(4-morpholinyl)-1H-benzimidazole-4-carboxylate, prepared as described in Example 30 (0.37 g, 0.827 mmol) in Tetrahydrofuran (THF) (10 mL) was cooled to 0° C. LiAlH$_4$ (0.038 g, 1 mmol) in THF (3 mL) was added in and the reaction mixture was stirred at 0° C. for 30 min. The reaction mixture was quenched with water (0.04 mL), NaOH (15%, 0.04 mL) then water (0.12 mL). Anhydrous MgSO$_4$ was added and the reaction mixture was filtered through celite and washed with EtOAc. Evaporation of the solvent gave the crude product. The crude product was purified on a silica column (1~4% MeOH/DCM) to give the solid (0.32 g, 88%). $^1$H NMR (400 MHz, DMSO-d$_6$) δ ppm 2.35 (s, 3H), 2.56 (s, 3H), 2.99-3.07 (m, 4H), 3.67-3.76 (m, 4H), 4.87 (d, J=5.81 Hz, 2H), 5.11 (t, J=5.68 Hz, 1H), 5.51 (s, 2H), 6.30 (d, J=7.83 Hz, 1H), 6.81 (d, J=2.27 Hz, 1H), 6.97 (d, J=2.02 Hz, 1H), 7.24 (t, J=7.83 Hz, 1H), 7.60 (d, 1H). MS (ES+) m/z 420.1 [M+H]$^+$.

Example 44

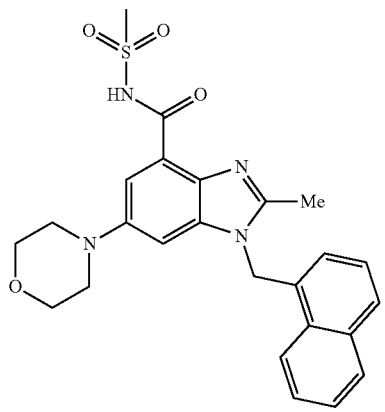 [SMILES: Cc1nc2c(C(=O)NS(C)(=O)=O)cc(N3CCOCC3)cc2n1Cc1cccc2ccccc12]

Preparation of 2-methyl-N-(methylsulfonyl)-6-(4-morpholinyl)-1-(1-naphthalenylmethyl)-1H-benzimidazole-4-carboxamide To the mixture of 2-methyl-6-(4-morpholinyl)-1-(1-naphthalenylmethyl)-1H-benzimidazole-4-carboxylic acid, prepared as described in Example 20 (100 mg, 0.249 mmol) in N,N-Dimethylformamide (DMF) (2 mL) in a 20 mL vial was added EDC (57.3 mg, 0.299 mmol), methane sulfonamide (47.4 mg, 0.498 mmol) and DMAP (21.30 mg, 0.174 mmol). The mixture was stirred at 60° C. and monitored by LC/MS. After stirring for 5 days the DMF was removed in-vacuo and the remaining residue was dissolved in 2 mL of DMSO and purified by reverse phase chromatography with 2 injections eluting with a 27% to 57% AcCN/H$_2$O gradient over 12 minutes. The fractions containing the desired compound, as determined by LC/MS, were combined and concentrated in-vacuo to provide the desired compound (47 mg, 0.097 mmol, 39.0% yield) as bright yellow solid. $^1$H NMR (400 MHz, DMSO-d$_6$) δ ppm 2.52 (s, 3H), 3.12 (t, 4H), 3.50 (s, 3H), 3.73 (t, 4H), 6.15 (s, 2H), 6.38 (d, 1H), 7.35 (t, aH), 7.50 (s. 1H), 7.51-7.75 (m, 2H), 7.88 (d, 1H), 8.05 (d, 1H), 8.25 (2, 1H), 8.35 (s, 1H), 12.8 (br. s, 1H); LC-MS: m/e=480 [M+1]$^+$

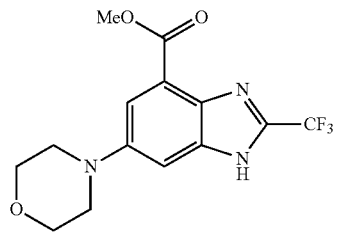 [SMILES: COC(=O)c1cc(N2CCOCC2)cc2[nH]c(C(F)(F)F)nc12]

Preparation of methyl 5-(4-morpholinyl)-2-(trifluoromethyl)-1H-benzimidazole-7-carboxylate a) methyl 2,3-diamino-5-(4-morpholinyl)benzoate

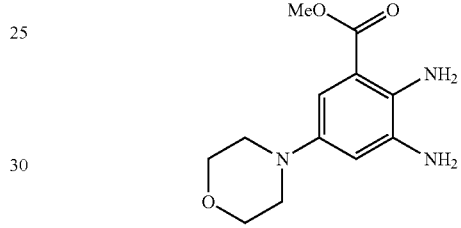

A mixture of methyl 3-amino-5-morpholino-2-nitrobenzoate, prepared as described in Example 26, step c (19.2 g, 68.3 mmol) and Pd/C (1.9 g) in MeOH (500 mL) in an autoclave under an atmosphere of H$_2$ (4 atm) were stirred at room temperature for 3 h, When TLC analysis indicated complete consumption of starting material, the mixture was filtered and the filtrate was concentrated in-vacuo to afford the desired product as a brown solid (13.9 g, 80.1%). $^1$H NMR (300 MHz, DMSO-d$_6$): δ ppm 6.62 (d, 1H, J=2.4 Hz), 6.54 (d, 1H, J=2.4 Hz), 5.84 (s, 2H), 4.75 (s, 2H), 3.76 (s, 3H), 3.70 (t, 4H, J=4.8 Hz), 2.85 (t, 4H, 4.8 Hz). LC-MS: m/e=252.1 [M+1]$^+$.

b) methyl 5-(4-morpholinyl)-2-(trifluoromethyl)-1H-benzimidazole-7-carboxylate

A mixture of methyl 2,3-diamino-5-(4-morpholinyl)benzoate (4.0 g) in CF$_3$COOH (20 mL) was heated at reflux temperature for 8 h. When TLC analysis indicated consumption of starting material, the mixture was cooled to room temperature and the solvent was removed in-vacuo. The residue was diluted with aqueous NaHCO$_3$ and extracted with EtOAc (250 mL×3). The combined organic layers were washed with brine (250 mL×2), dried over anhydrous Na$_2$SO$_4$. After filtration, the solvent was removed by rotary evaporator. The residue was then purified by silica gel chromatography eluted with EtOAc:petroleum ether=1:4 to afford the desired product as a pale solid. (4.3 g, 82.7%). $^1$H NMR (300 MHz, DMSO-d$_6$): δ ppm 13.47 (s, 1H), 7.71 (s, 1H), 7.56 (s, 1H), 3.96 (s, 3H), 3.79 (t, 4H, J=4.5 Hz), 3.17 (s, 4H). LC-MS: m/e=330.1 [M+1]$^+$.

Example 46

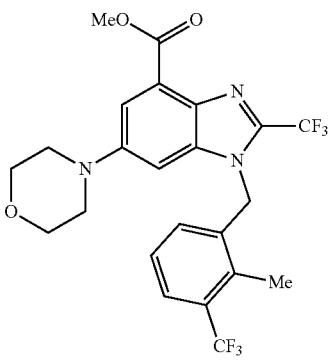 [SMILES: COC(=O)c1cc(N2CCOCC2)cc2c1nc(C(F)(F)F)n2Cc1cccc(C(F)(F)F)c1C]

Preparation of methyl 1-{[2-methyl-3-(trifluoromethyl)phenyl]methyl}-6-(4-morpholinyl)-2-(trifluoromethyl)-1H-benzimidazole-4-carboxylate A suspension of methyl 5-(4-morpholinyl)-2-(trifluoromethyl)-1H-benzimidazole-7-carboxylate, prepared as described in Example 45 (1.5 g, 4.56 mmol) and potassium carbonate (1.889 g, 13.67 mmol) in N,N-Dimethylformamide (DMF) (10 mL) was stirred at rt for 15 min. 1-(Bromomethyl)-2-methyl-3-(trifluoromethyl)benzene (1.729 g, 6.83 mmol) was added in and the resulting reaction mixture was stirred for 3 h at 80° C. The mixture was then cooled to room temperature and poured into ice/water. The precipitate was collected by filtration, washed with water, then hexanes (turned into a gum on the filter paper—some material was lost). The crude material was purified on a silica gel column (ISCO, eluting with 0-5% MeOH in DCM) to give the desired product (580 mg, 1.099 mmol, 24.12% yield) (several mixed fractions obtained were discarded). $^1$H NMR (400 MHz, DMSO-$d_6$) δ ppm 7.65 (d, J=2.53 Hz, 1H), 7.61 (d, J=7.83 Hz, 1H), 7.37 (d, J=2.27 Hz, 1H), 7.23 (t, J=7.96 Hz, 1H), 6.29 (d, J=7.58 Hz, 1H), 5.76 (s, 2H), 3.93 (s, 3H), 3.70-3.78 (m, 4H), 3.12-3.22 (m, 4H), 2.53 (s, 3H). MS (ES+) m/e 502 [M+H]$^+$.

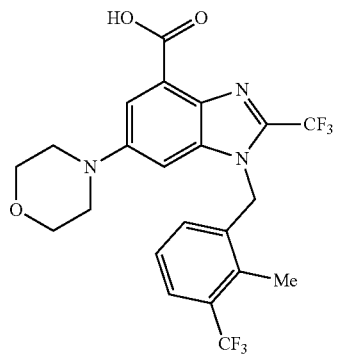 [SMILES: Cc1c(Cn2c(C(F)(F)F)nc3c(C(=O)O)cc(N4CCOCC4)cc32)cccc1C(F)(F)F]

Preparation of 1-{[2-methyl-3-(trifluoromethyl)phenyl]methyl}-6-(4-morpholinyl)-2-(trifluoromethyl)-1H-benzimidazole-4-carboxylic acid A mixture of methyl 1-{[2-methyl-3-(trifluoromethyl)phenyl]methyl}-6-(4-morpholinyl)-2-(trifluoromethyl)-1H-benzimidazole-4-carboxylate, prepared as described in Example 46 (510 mg, 1.017 mmol) and 2 M lithium hydroxide (6 mL, 12.00 mmol) in THF (12 mL) was stirred at 50° C. for 2 h. The reaction was cooled to room temperature. The organic solvent was removed under reduced pressure and the aqueous was diluted with water and acidified by the addition of 1 N HCl. The precipitate formed was collected by filtration. The solid was washed with ether and turned into a gummy residue. The residue was washed with MeOH until all the material was transferred into the collection flask. The organics were evaporated and a white solid formed upon standing. The precipitate was collected by filtration, washed with water and dried to give the desired product (438 mg, 0.881 mmol, 87% yield) as a white powder. $^1$H NMR (400 MHz, DMSO-$d_6$) δ ppm 7.68 (d, J=2.02 Hz, 1H), 7.61 (d, J=8.08 Hz, 1H), 7.23 (t, J=7.83 Hz, 1H), 7.08 (d, J=2.02 Hz, 1H), 6.27 (d, J=7.58 Hz, 1H), 5.74 (s, 2H), 3.63-3.82 (m, 4H), 3.05-3.21 (m, 4H), 2.52 (br. s., 3H). MS (ES+) m/e 488 [M+H]$^+$.

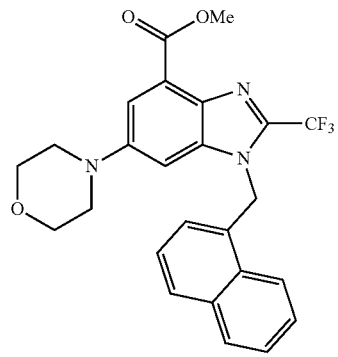 [SMILES: COC(=O)c1cc(N2CCOCC2)cc2c1nc(C(F)(F)F)n2Cc1cccc2ccccc12]

Preparation of methyl 6-(4-morpholinyl)-1-(1-naphthalenylmethyl)-2-(trifluoromethyl)-1H-benzimidazole-4-carboxylate A mixture of methyl 5-(4-morpholinyl)-2-(trifluoromethyl)-1H-benzimidazole-7-carboxylate prepared as described in Example 45 (1.5 g, 4.56 mmol) and potassium carbonate (1.889 g, 13.67 mmol) in N,N-Dimethylformamide (DMF) (10 mL) was stirred at rt for 10 min. After addition of 1-(bromomethyl)naphthalene (1.511 g, 6.83 mmol), the mixture was warmed to 80° C. and stirred for 3 h at this temperature. The resulting mixture was cooled to rt and poured over ice. The precipitate formed was collected by filtration and air dried (2.4 g total). The crude material was purified on silica gel (ISCO, 0-5% MeOH in DCM) to give methyl 6-(4-morpholinyl)-1-(1-naphthalenylmethyl)-2-(trifluoromethyl)-1H-benzimidazole-4-carboxylate (1.48 g, 3.15 mmol, 69.2% yield). A portion of this material (138 mg) was purified by reverse phase-HPLC (25 to 95% AcCN in water, plus 0.1% TFA) to give the desired product (93.4 mg, 0.195 mmol, 4.28% yield) as a white solid. $^1$H NMR (400 MHz, DMSO-$d_6$) δ ppm 8.26 (d, J=8.34 Hz, 1H), 8.01 (d, J=7.33 Hz, 1H), 7.85 (d, J=8.08 Hz, 1H), 7.60-7.73 (m, 3H), 7.39 (d, J=2.27 Hz, 1H), 7.31 (t, J=7.83 Hz, 1H), 6.24 (br. s., 1H), 6.22 (s, 2H), 3.95 (s, 3H), 3.64-3.73 (m, 4H), 3.06-3.19 (m, 4H). MS (ES+) m/e 470 [M+H]$^+$.

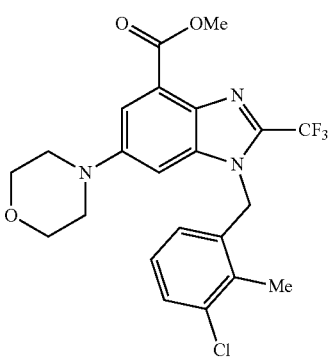 [SMILES: COC(=O)c1cc(N2CCOCC2)cc2c1nc(C(F)(F)F)n2Cc1cccc(Cl)c1C]

Preparation of methyl 1-[(3-chloro-2-methylphenyl)methyl]-6-(4-morpholinyl)-2-(trifluoromethyl)-1H-benzimidazole-4-carboxylate A mixture of methyl 5-(4-morpholinyl)-2-(trifluoromethyl)-1H-benzimidazole-7-carboxylate, prepared as described in Example 45 (1.5 g, 4.56 mmol) and potassium carbonate (1.889 g, 13.67 mmol) in N,N-Dimethylformamide (DMF) (10 mL) was stirred at rt for 10 min. After addition of 1-(bromomethyl)-3-chloro-2-methylbenzene (1.500 g, 6.83 mmol), the mixture was warmed to 80° C. and stirred for 3 h at this temperature. The resulting mixture was cooled to rt and poured over ice. The precipitate formed was collected by filtration and air dried (2.4 g total). Purification on a silica gel column (10-50% EtOAc in hexane) failed to produce pure material. The fractions containing product were combined and the solvent was removed under reduced pressure to afford methyl 1-[(3-chloro-2-methylphenyl)methyl]-6-(4-morpholinyl)-2-(trifluoromethyl)-1H-benzimidazole-4-carboxylate (2.03 g, 4.34 mmol, 95% yield) (only 87% pure). A portion of this material (165 mg) was purified by RP-HPLC (25 to 95% AcCN in water, plus 0.1% TFA) to give pure desired product (92.3 mg, 0.193 mmol, 4.24% yield). $^1$H NMR (400 MHz, DMSO-$d_6$) δ ppm 7.64 (d, J=2.27 Hz, 1H), 7.28-7.43 (m, 2H), 7.04 (t, J=7.96 Hz, 1H), 5.97 (d, J=7.83 Hz, 1H), 5.71 (s, 2H), 3.93 (s, 3H), 3.66-3.80 (m, 4H), 3.06-3.25 (m, 4H), 2.46 (s, 3H). MS (ES+) m/e 468 [M+H]$^+$

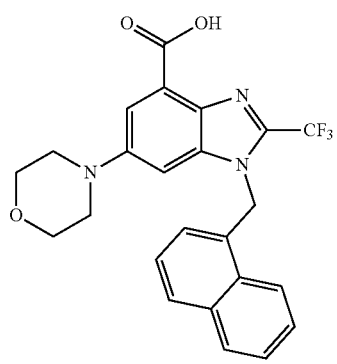 [SMILES: O=C(O)c1cc(N2CCOCC2)cc2c1nc(C(F)(F)F)n2Cc1cccc2ccccc12]

Preparation of 6-(4-morpholinyl)-1-(1-naphthalenylmethyl)-2-(trifluoromethyl)-1H-benzimidazole-4-carboxylic acid A suspension of methyl 6-(4-morpholinyl)-1-(1-naphthalenylmethyl)-2-(trifluoromethyl)-1H-benzimidazole-4-carboxylate, prepared as described in Example 48 (1.28 g, 2.73 mmol) in Methanol (18 mL) and 1 M sodium hydroxide (15 mL, 15.00 mmol) was stirred overnight at rt, then at 50° C. for 5 h. The reaction was cooled to room temperature and acidified (pH 4) by the addition of 1 N HCl. The precipitate formed was collected by filtration, washed with water and dried to give the desired product (1.13 g, 2.233 mmol, 82% yield). A portion of this material (132 mg) was purified by reverse phase-HPLC (15-95% AcCN in water plus 0.1% TFA). The fractions containing product were combined and the volume was reduced to about ⅓ of the original. The precipitate formed was collected, washed with water and dried in a vacuum oven (50° C., overnight) to give the desired product (88.4 mg, 0.194 mmol, 7.12% yield). $^1$H NMR (400 MHz, DMSO-$d_6$) δ ppm 13.11 (br. s., 1H), 8.26 (d, J=8.59 Hz, 1H), 8.01 (d, J=7.33 Hz, 1H), 7.85 (d, J=8.34 Hz, 1H), 7.57-7.73 (m, 3H), 7.35 (d, J=2.53 Hz, 1H), 7.29-7.34 (m, 1H), 6.24 (d, J=7.07 Hz, 1H), 6.22 (s, 2H), 3.64-3.72 (m, 4H), 3.06-3.18 (m, 4H). MS (ES+) m/e 456 [M+H]$^+$.

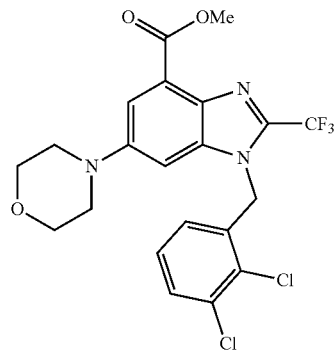 [SMILES: COC(=O)c1cc(N2CCOCC2)cc2c1nc(C(F)(F)F)n2Cc1cccc(Cl)c1Cl]

Preparation of methyl 1-[(2,3-dichlorophenyl)methyl]-6-(4-morpholinyl)-2-(trifluoromethyl)-1H-benzimidazole-4-carboxylate A mixture of methyl 5-(4-morpholinyl)-2-(trifluoromethyl)-1H-benzimidazole-7-carboxylate, prepared as described in Example 45 (1.5 g, 4.56 mmol) and potassium carbonate (1.889 g, 13.67 mmol) in N,N-Dimethylformamide (DMF) (10 mL) was stirred at rt for 10 min. After addition of 1-(bromomethyl)-2,3-dichlorobenzene (1.639 g, 6.83 mmol), the mixture was warmed to 80° C. and stirred for 3 h at this temperature. The resulting mixture was cooled to rt and poured over ice. The precipitate formed was collected by filtration and air dried to give crude product (2.2 g, 4.51 mmol, 99% yield) (91% pure). A portion of this material (230 mg) was purified by reverse phase-HPLC (25 to 95% AcCN in water, plus 0.1% TFA) to give the desired product (137.4 mg, 0.276 mmol, 6.05% yield). $^1$H NMR (400 MHz, DMSO-$d_6$) δ ppm 7.65 (d, J=2.27 Hz, 1H), 7.61 (dd, J=8.08, 1.26 Hz, 1H), 7.48 (d, J=2.27 Hz, 1H), 7.24 (t, J=7.96 Hz, 1H), 6.25 (dd, J=7.83, 1.26 Hz, 1H), 5.77 (s, 2H), 3.93 (s, 3H), 3.68-3.81 (m, 4H), 3.13-3.24 (m, 4H). MS (ES+) m/e 488 [M+H]$^+$.

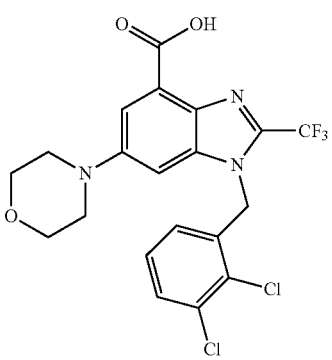 [SMILES: O=C(O)c1cc(N2CCOCC2)cc2c1nc(C(F)(F)F)n2Cc1cccc(Cl)c1Cl]

Preparation of 1-[(2,3-dichlorophenyl)methyl]-6-(4-morpholinyl)-2-(trifluoromethyl)-1H-benzimidazole-4-carboxylic acid A mixture of methyl 1-[(2,3-dichlorophenyl)methyl]-6-(4-morpholinyl)-2-(trifluoromethyl)-1H-benzimidazole-4-carboxylate prepared as described in Example 51 (1.95 g, 3.99 mmol) and 2 M lithium hydroxide (0.096 g, 3.99 mmol) in Tetrahydrofuran (THF) was stirred at 50° C. for 3 h. The reaction was cooled to room temperature, the organic solvent was removed under reduced pressure and the aqueous residue was acidified (pH 4) by the addition of 1N HCl. A gummy precipitate formed. After standing at rt overnight, it turned into a solid. The precipitate was collected, washed with water and dried to give crude desired product (1.83 g, 3.86 mmol, 97% yield) as a gray solid. A portion of this material (148 mg) was purified by reverse phase-HPLC (15-95% AcCN in water plus 0.1% TFA). The fractions containing product were combined and the volume was reduced to about ⅓ of the original. The precipitate formed was collected, washed with water and dried in a vacuum oven to give desired product (88.3 mg, 0.182 mmol, 4.57% yield). $^1$H NMR (400 MHz, DMSO-d$_6$) δ ppm 13.09 (s, 1H), 7.64 (d, J=2.53 Hz, 1H), 7.61 (dd, J=8.08, 1.26 Hz, 1H), 7.44 (d, J=2.27 Hz, 1H), 7.24 (t, J=8.08 Hz, 1H), 6.26 (dd, J=7.83, 1.26 Hz, 1H), 5.77 (s, 2H), 3.66-3.81 (m, 4H), 3.12-3.25 (m, 4H). MS (ES+) m/e 474 [M+H]$^+$.

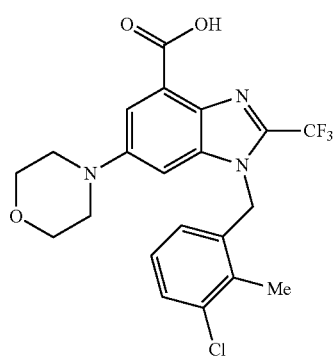 [SMILES: Cc1c(Cl)cccc1Cn1c(C(F)(F)F)nc2c(C(=O)O)cc(N3CCOCC3)cc21]

Preparation of 1-[(3-chloro-2-methylphenyl)methyl]-6-(4-morpholinyl)-2-(trifluoromethyl)-1H-benzimidazole-4-carboxylic acid A suspension of methyl 1-[3-chloro-2-methylphenyl)methyl]-6-(4-morpholinyl)-2-(trifluoromethyl)-1H-benzimidazole-4-carboxylate, prepared as described in Example 49 (1.09 g, 2.330 mmol) in Methanol (12 mL) and Tetrahydrofuran (THF) (4 mL) was treated with 1 M aq. sodium hydroxide (12 mL, 12.00 mmol) and stirred at 70° C. for 1.5 h (mixture turned homogeneous). The reaction was cooled to room temperature, the volume reduced to half and the residue was acidified (pH 4) by the addition of 1 N HCl. The precipitate was collected, washed with water and dried to give crude desired product (918.6 mg, 2.024 mmol, 87% yield) as a yellow solid. A portion of it (140 mg) was suspended in 3.5 mL of DMSO. After sonication and heating, the solid went into solution but it crashed out. The precipitate was collected and washed with DMSO, but it still showed impurities by LC/MS. Another aliquot (132 mg) was dissolved with heating in 5 mL of DMSO and purified by reverse phase-HPLC (15 to 95% AcCN in water plus 0.1% TFA). The desired product was isolated by evaporation of the organic solvent: the precipitate was collected by filtration, washed with water and dried in a vacuum oven to afford pure desired product (89 mg, 0.192 mmol, 8.25% yield). $^1$H NMR (400 MHz, DMSO-d$_6$) δ ppm 13.09 (s, 1H), 7.63 (d, J=2.27 Hz, 1H), 7.36 (d, J=7.83 Hz, 1H), 7.30 (d, J=2.27 Hz, 1H), 7.05 (t, J=7.96 Hz, 1H), 5.98 (d, J=7.58 Hz, 1H), 5.70 (s, 2H), 3.66-3.83 (m, 4H), 3.08-3.24 (m, 4H), 2.47 (s, 3H). MS (ES+) m/e 453.9 [M+H]$^+$.

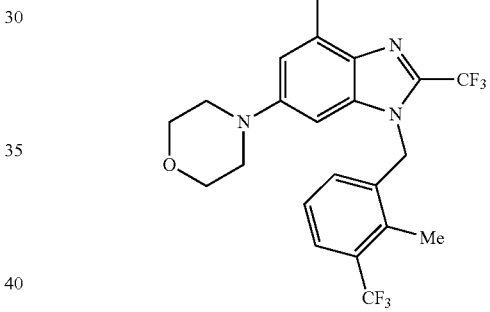

Preparation of 1-{[2-methyl-3-(trifluoromethyl)phenyl]methyl}-6-(4-morpholinyl)-2-(trifluoromethyl)-1H-benzimidazole-4-carboxamide Oxalyl chloride (0.251 mL, 2.87 mmol) was added to a suspension of 1-{[2-methyl-3-(trifluoromethyl)phenyl]methyl}-6-(4-morpholinyl)-2-(trifluoromethyl)-1H-benzimidazole-4-carboxylic acid, prepared as described in Example 47 (350 mg, 0.718 mmol) in Dichloromethane (DCM) (6 mL). The reaction mixture was stirred at rt for 10 minutes (turned into a solution) and then the solvent was evaporated. The residue (crude acid chloride), was dissolved in Tetrahydrofuran (THF) (6 mL). NH$_3$ gas was bubbled in (the mixture changed color yellow to white, and a precipitate formed); the mixture was stirred at rt for 10 minutes and then partitioned between brine (15 mL) and EtOAc (20 mL). The aqueous phase was extracted with another aliquot of EtOAc (20 mL). The organic phases were combined and concentrated to afford desired product (297 mg, 0.580 mmol, 81% yield). $^1$H NMR (400 MHz, DMSO-d$_6$) δ ppm 8.59 (d, J=2.53 Hz, 1H), 7.99 (d, J=2.78 Hz, 1H), 7.77 (d, J=2.27 Hz, 1H), 7.62 (d, J=7.58 Hz, 1H), 7.31 (d, J=2.27 Hz, 1H), 7.25 (t, J=7.83 Hz, 1H), 6.36 (d, J=7.58 Hz, 1H), 5.78 (s, 2H), 3.60-3.80 (m, 4H), 3.09-3.22 (m, 4H), 2.53 (s, 3H). MS (ES+) m/e 487 [M+H]$^+$

Example 55

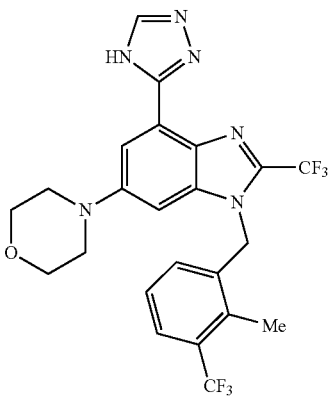 [SMILES: Cc1c(Cn2c(C(F)(F)F)nc3c(-c4nnc[nH]4)cc(N4CCOCC4)cc32)cccc1C(F)(F)F]

Preparation of 1-{[2-methyl-3-(trifluoromethyl)phenyl]methyl}-6-(4-morpholinyl)-4-(1H-1,2,4-triazol-3-yl)-2-(trifluoromethyl)-1H-benzimidazole A mixture of 1-{[2-Methyl-3-(trifluoromethyl)phenyl]methyl}-6-(4-morpholinyl)-2-(trifluoromethyl)-1H-benzimidazole-4-carboxamide, prepared as described in Example 54 (250 mg, 0.514 mmol) and N,N-dimethylformamide dimethyl acetal (7 mL, 52.3 mmol) was stirred at 105° C. for 1.5 hour. The reaction mixture was concentrated under reduced pressure and the residue was suspended in Acetic Acid (5 mL). After the addition of hydrazine monohydrate (0.113 mL, 3.60 mmol) the reaction mixture was heated at 100° C. for 1 hour. The solvent was concentrated under vacuum, the residue was azeotroped with toluene (2×), and the residue was dissolved in DMSO and purified by reverse phase-HPLC (20-95% AcCN in water plus 0.1% TFA). The fractions containing product were combined, neutralized by the addition of aq NaHCO$_3$ sat sol and the organic evaporated. The precipitate in the aqueous residue was collected by filtration, washed with water and dried in a vacuum oven (45° C.) overnight to give the desired product (157.1 mg, 0.302 mmol, 58.7% yield) as a white powder. $^1$H NMR (400 MHz, CHLOROFORM-d) δ ppm 13.05 (br. s., 1H), 8.12 (s, 1H), 8.00 (d, J=2.27 Hz, 1H), 7.63 (d, J=7.83 Hz, 1H), 7.18 (t, J=7.83 Hz, 1H), 6.56 (d, J=7.83 Hz, 1H), 6.51 (d, J=2.27 Hz, 1H), 5.54 (s, 2H), 3.71-3.95 (m, 4H), 3.09-3.30 (m, 4H), 2.57 (s, 3H). MS (ES+) m/e 511[M+H]$^+$.

Example 56

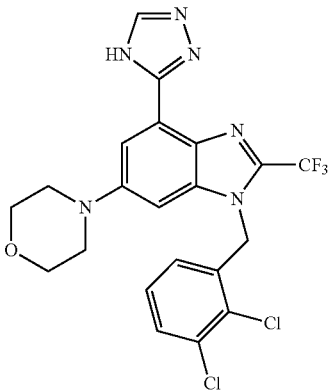 [SMILES: FC(F)(F)c1nc2c(-c3nnc[nH]3)cc(N3CCOCC3)cc2n1Cc1cccc(Cl)c1Cl]

Preparation of 1-[(2,3-dichlorophenyl)methyl]-6-(4-morpholinyl)-4-(1H-1,2,4-triazol-3-yl)-2-(trifluoromethyl)-1H-benzimidazole a) 1-[(2,3-Dichlorophenyl)methyl]-6-(4-morpholinyl)-2-(trifluoromethyl)-1H-benzimidazole-4-carboxamide

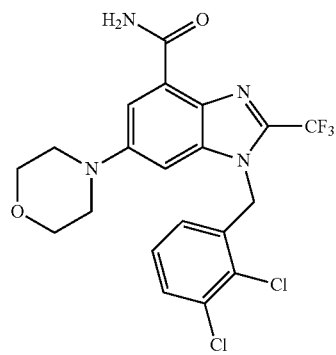 [SMILES: NC(=O)c1cc(N2CCOCC2)cc2c1nc(C(F)(F)F)n2Cc1cccc(Cl)c1Cl]

Oxalyl chloride (0.332 mL, 3.80 mmol) was added to a suspension of 1-[(2,3-dichlorophenyl)methyl]-6-(4-morpholinyl)-2-(trifluoromethyl)-1H-benzimidazole-4-carboxylic acid, prepared as described in Example 52 (450 mg, 0.949 mmol) in Dichloromethane (DCM) (7 mL). The reaction mixture was stirred at rt for 10 minutes and then the solvent was evaporated. The residue (crude acid chloride), was suspended in Tetrahydrofuran (THF) (7 mL). NH$_3$ gas was bubbled in (the mixture changed color yellow to white), the mixture was stirred at rt for 15 minutes and then partitioned between brine (15 mL) and EtOAc (20 mL). The aqueous phase was extracted with EtOAc (2×20 mL) and CH$_2$Cl$_2$ (10 mL). The organic phases were combined, dried over Na$_2$SO$_4$ and concentrated to afford the desired product (395 mg, 0.835 mmol, 88% yield) which was used as is in the next step. $^1$H NMR (400 MHz, DMSO-d$_6$) δ ppm 8.56 (d, J=2.27 Hz, 1H), 7.98 (d, J=2.53 Hz, 1H), 7.76 (d, J=2.27 Hz, 1H), 7.62 (dd, J=8.08, 1.26 Hz, 1H), 7.42 (d, J=2.27 Hz, 1H), 7.25 (t, J=7.96 Hz, 1H), 6.33 (dd, J=7.83, 1.26 Hz, 1H), 5.80 (s, 2H), 3.68-3.83 (m, 4H), 3.14-3.24 (m, 4H). MS (ES+) m/e 473.1 [M+H]$^+$.

b) 1-[(2,3-Dichlorophenyl)methyl]-6-(4-morpholinyl)-4-(1H-1,2,4-triazol-3-yl)-2-(trifluoromethyl)-1H-benzimidazole A suspension of 1-[(2,3-dichlorophenyl)methyl]-6-(4-morpholinyl)-2-(trifluoromethyl)-1H-benzimidazole-4-carboxamide, prepared as described in Example 56, step a (389 mg, 0.822 mmol) in N,N-dimethylformamide dimethyl acetal (9 mL, 67.2 mmol) was stirred at 105° C. for 1 hour. The reaction was concentrated under reduced pressure and the residue was suspended in Acetic Acid (7 mL). After the addition of hydrazine monohydrate (0.181 mL, 5.75 mmol) the reaction mixture was heated at 100° C. for 1 hour. The solvent was concentrated under vacuum and the residue was dissolved in DMSO and purified by reverse phase-HPLC (20-95% AcCN in water plus 0.1% TFA) (some residual solid filtered off). The fractions containing product were combined, neutralized by the addition of aq NaHCO$_3$ sat sol and the organic evaporated (some compound lost during transfer). The precipitate in the aqueous residue was collected by filtration, washed with water and dried in a vacuum oven (45° C.) overnight to give the desired product (115 mg, 0.227 mmol, 27.6% yield) as a white powder. $^1$H NMR (400 MHz, CHLOROFORM-d) δ ppm 13.05 (br. s., 1H), 8.12 (s, 1H), 8.00 (d, J=2.27 Hz, 1H), 7.47 (dd, J=8.08, 1.26 Hz, 1H), 7.10 (t, J=7.96 Hz, 1H), 6.59 (d, J=2.27 Hz, 1H), 6.37 (dd, J=7.83, 1.01 Hz, 1H), 5.62 (s, 2H), 3.79-3.92 (m, 4H), 3.17-3.30 (m, 4H). MS (ES+) m/e 497 [M+H]$^+$.

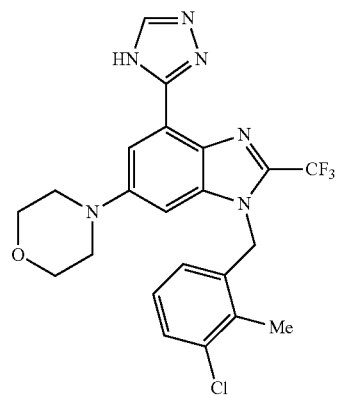 [SMILES: Cc1c(Cl)cccc1Cn1c(C(F)(F)F)nc2c(-c3nnc[nH]3)cc(N3CCOCC3)cc21]

Preparation of 1-[(3-chloro-2-methylphenyl)methyl]-6-(4-morpholinyl)-4-(1H-1,2,4-triazol-3-yl)-2-(trifluoromethyl)-1H-benzimidazole Oxalyl chloride (0.347 mL, 3.97 mmol) was added to a suspension of 1-[(3-chloro-2-methylphenyl)methyl]-6-(4-morpholinyl)-2-(trifluoromethyl)-1H-benzimidazole-4-carboxylic acid, prepared as described in Example 53 (450 mg, 0.992 mmol) in Dichloromethane (DCM) (8 mL). The reaction mixture was stirred at rt for 10 minutes and then the solvent was evaporated. The residue (crude acid chloride), was suspended in Tetrahydrofuran (THF) (8 mL). NH$_3$ gas was bubbled in (the mixture changed color yellow to white) and the mixture was stirred at rt for 15 minutes and then partitioned between brine (15 mL) and EtOAc (20 mL). The aqueous phase was extracted with EtOAc (2×20 mL) and CH$_2$Cl$_2$ (10 mL). The organic phases were combined, dried over Na$_2$SO$_4$ and concentrated. The crude product was suspended in N,N-dimethylformamide dimethyl acetal (10 mL, 74.7 mmol) and stirred at 105° C. for 2 h. The excess solvent was evaporated and the residue was suspended in Acetic Acid (10 mL). After the addition of hydrazine monohydrate (0.194 mL, 3.97 mmol), the mixture was stirred at 100° C. for 1.5 h. The solvent was evaporated and the residue was dissolved in warm DMSO (8 mL) and purified by reverse phase-HPLC (20-90% AcCN in water plus 0.1% TFA) to give the desired product (96 mg, 0.197 mmol, 19.90% yield) as a white powder. $^1$H NMR (400 MHz, CHLOROFORM-d) δ ppm 13.08 (br. s., 1H), 8.11 (s, 1H), 7.98 (d, J=2.27 Hz, 1H), 7.36 (d, J=8.08 Hz, 1H), 7.01 (t, J=7.96 Hz, 1H), 6.51 (d, J=2.02 Hz, 1H), 6.32 (d, J=7.83 Hz, 1H), 5.51 (s, 2H), 3.73-3.97 (m, 4H), 3.12-3.30 (m, 4H), 2.50 (s, 3H). MS (ES+) m/e 476.9 [M+H]$^+$.

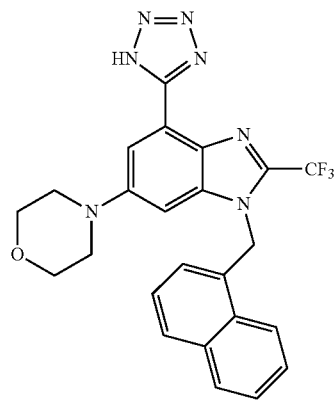 [SMILES: FC(F)(F)c1nc2c(-c3nnn[nH]3)cc(N3CCOCC3)cc2n1Cc1cccc2ccccc12]

Preparation of 2-methyl-6-(4-morpholinyl)-1-(1-naphthalenylmethyl)-4-(1H-tetrazol-5-yl)-1H-benzimidazole In a two 5 mL MW vial was added in 2-methyl-6-(4-morpholinyl)-1-(1-naphthalenylmethyl)-1H-benzimidazole-4-carbonitrile, prepared as described in Example 24 (80 mg, 0.209 mmol), sodium azide (109 mg, 1.673 mmol) and ammonium chloride (90 mg, 1.673 mmol) and N,N-Dimethylformamide (DMF) (2 mL). The reaction mixture was subjected to MW irradiation for 15 min at 180° C., then 80 min at 185° C. LC-MS analysis only showed 30% conversion; however, heating for longer time caused the decomposition of the product. The two reaction mixtures were combined. The combined mixture was added in water (10 mL) and extracted with DCM (30 mL×4). The combined organic phases were washed with saturated NH$_4$Cl solution, dried, and concentrated. The reaction was subjected to purification on a silica column (20~60% EtOAc/Hexane) and then (1~5% MeOH/DCM) to give the product (24 mg, 13%). $^1$H NMR (400 MHz, DMSO-d$_6$) δ ppm 2.53 (s, 3H) 3.08-3.15 (m, 4H) 3.68-3.75 (m, 4H) 6.10 (s, 2H) 6.40 (d, J=7.33 Hz, 1H) 7.26-7.39 (m, 2H) 7.56-7.74 (m, 3H) 7.88 (d, J=8.34 Hz, 1H) 8.03 (d, J=8.08 Hz, 1H) 8.26 (d, 1H). MS (ES+) m/e 426.0 [M+H]$^+$.

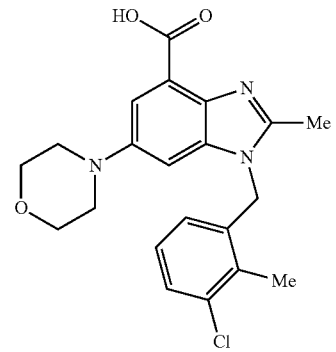 [SMILES: Cc1c(Cl)cccc1Cn1c(C)nc2c(C(=O)O)cc(N3CCOCC3)cc21]

Preparation of 1-[(3-chloro-2-methylphenyl)methyl]-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 1-(bromomethyl)-3-chloro-2-methylbenzene (0.239 g, 1.090 mmol) and potassium carbonate (0.301 g, 2.179 mmol). The resulting reaction mixture was stirred for 3 h at 80° C. The solution was cooled to room temperature and poured into water and extracted with EtOAc. The combined organic phase was washed with brine and concentrated. The residue was purified on a Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in-vacuo. The solution was diluted with water (20 mL) and acidified with 1 N HCl. The mixture was then filtered and the yellow solid was purified by reversed phase with a gradient of acetonitrile (0.1% TFA) and water (0.1% TFA v/v)(25-55%) over 10 minutes. The appropriate fractions were collected and evaporated to yield the desired product (104.4 mg, 0.253 mmol, 34.9% yield). $^1$H NMR (400 MHz, CHLOROFORM-d) δ ppm 2.48 (s, 3H) 2.85 (s, 3H) 3.13 (d, J=4.04 Hz, 4H) 3.78-3.90 (m, 4H) 5.58 (s, 2H) 6.37 (d, J=7.83 Hz, 1H) 6.89 (d, J=1.52 Hz, 1H) 7.04 (t, J=7.96 Hz, 1H) 7.37 (d, J=8.08 Hz, 1H) 7.52 (d, 1H). MS (ES+) m/e 399.8 [M+H]$^+$.

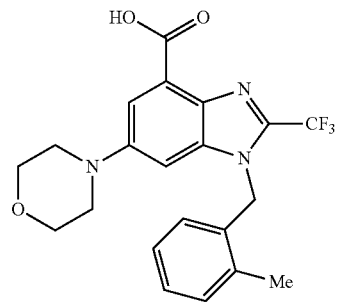 [SMILES: Cc1ccccc1Cn1c(C(F)(F)F)nc2c(C(=O)O)cc(N3CCOCC3)cc21]

Preparation of 2-methyl-1-[(2-methylphenyl)methyl]-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 2-methylbenzyl bromide (0.145 mL, 1.090 mmol) and potassium carbonate (0.301 g, 2.179 mmol). The resulting reaction mixture was stirred for 3 h at 80° C. The solution was cooled to room temperature and poured into water and was extracted with EtOAc. The combined organic phase was washed with Brine and concentrated. The residue was purified on a Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in-vacuo. The solution was diluted with water (20 mL) and acidified with 1 N HCl. The mixture was then filtered and the grey solid was purified by reversed phase HPLC with a gradient of acetonitrile (0.1% TFA) and water (0.1% TFA v/v)(10-40%) over 10 minutes. The appropriate fractions were collected and evaporated to yield the desired product (152.6 mg, 0.418 mmol, 57.5% yield). $^1$H NMR (400 MHz, CHLOROFORM-d) δ ppm 2.45 (s, 3H) 2.87 (s, 3H) 3.00 (br. s., 4H) 3.72-3.81 (m, 4H) 5.53 (s, 2H) 6.60 (d, J=7.58 Hz, 1H) 6.78 (d, J=1.26 Hz, 1H) 7.14 (t, 1H) 7.23-7.33 (m, 3H). MS (ES+) m/e 365.8 [M+H]$^+$.

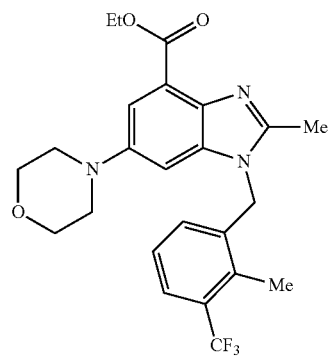 [SMILES: CCOC(=O)c1cc(N2CCOCC2)cc2c1nc(C)n2Cc1cccc(C(F)(F)F)c1C]

Preparation of ethyl 2-methyl-1-{[2-methyl-3-(trifluoromethyl)phenyl]methyl}-6-(4-morpholinyl)-1H-benzimidazole-4-carboxylate To a mixture of 2-methyl-1-{[2-methyl-3-(trifluoromethyl)phenyl]methyl}-6-(4-morpholinyl)-1H-benzimidazole-4-carboxylic acid, prepared as described in Example 31 (0.25 g, 0.577 mmol) in Dichloromethane (DCM) (20 mL) was added in oxalyl chloride (0.202 mL, 2.307 mmol) then followed by ten drops of DMF. The reaction was stirred at rt for 10 minutes and concentrated to give the acid chloride. To the crude acid chloride, was added Ethanol (20.00 mL). The reaction mixture was stirred at rt for 10 minutes. The reaction was concentrated. The crude product was purified on a silica column (0-10% MeOH/DCM). The fractions were concentrated and DCM (50 mL) was added in. The organic phase was washed with saturated NaHCO$_3$ solution (20 mL), Brine (20 mL), dried (MgSO$_4$) and concentrated to give the product as a white solid (0.18 g, 64%). $^1$H NMR (400 MHz, DMSO-d$_6$) δ ppm 1.38 (t, J=7.07 Hz, 3H) 2.56 (s, 3H) 2.59 (s, 3H) 3.10-3.18 (m, 4H) 3.70-3.78 (m, 4H) 4.45 (q, J=7.07 Hz, 2H) 5.71 (s, 2H) 6.49 (d, J=7.58 Hz, 1H) 7.26 (t, J=7.96 Hz, 1H) 7.43 (d, J=2.02 Hz, 1H) 7.55 (d, J=1.52 Hz, 1H) 7.64 (d, 1H). MS (ES+) m/e 462.2[M+H]$^+$.

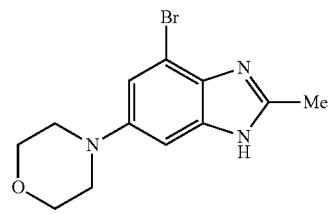 [SMILES: Cc1nc2c(Br)cc(N3CCOCC3)cc2[nH]1]

Preparation of 4-bromo-2-methyl-6-(4-morpholinyl)-1H-benzimidazole a) 6-bromo-2-methyl-4-nitro-1-(phenylmethyl)-1H-benzimidazole

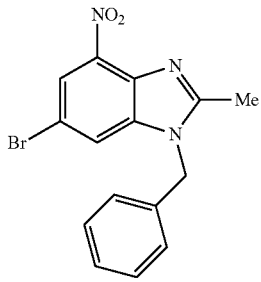 [SMILES: Cc1nc2c([N+](=O)[O-])cc(Br)cc2n1Cc1ccccc1]

A mixture of 6-bromo-2-methyl-4-nitro-1H-benzo[d]imidazole, prepared as described in Example 1 (22 g), (bromomethyl)benzene (15 g) and K$_2$CO$_3$ (35 g) in DMF (250 mL) was stirred at 60° C. for 2 h. The reaction mixture was cooled to room temperature and filtered. The filtrate was then poured into water. It was then filtered to afford a solid and the solid was washed with water and then dried in-vacuo to afford the desired product (28 g, 93%). $^1$H NMR (300 MHz, DMSO-d$_6$): δ ppm 2.60 (s, 3H), 5.62 (s, 2H), 7.12-7.15 (m, 2H), 7.29-7.39 (m, 3H), 8.12 (d, 1H, J=1.8 Hz), 8.32 (d, 1H, J=1.8 Hz); LC-MS: m/e=346 [M+1]$^+$.

b) 2-methyl-6-(4-morpholinyl)-4-nitro-1-(phenylmethyl)-1H-benzimidazole

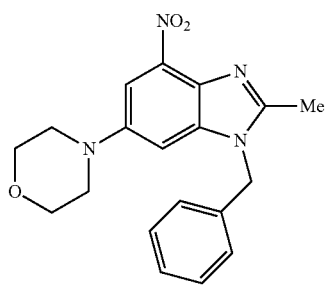 [SMILES: Cc1nc2c([N+](=O)[O-])cc(N3CCOCC3)cc2n1Cc1ccccc1]

A mixture of 6-bromo-2-methyl-4-nitro-1-(phenylmethyl)-1H-benzimidazole (28 g), morpholine (21 g), Pd(dba)$_2$ (4.6 g), Cs$_2$CO$_3$ (52.8 g) and X-Phos (3.9 g) in dioxane (250 mL) was degassed with nitrogen and then stirred at 82° C. for 4 h. The mixture was cooled to room temperature and the solvent was removed in-vacuo. The residue was then purified by silica gel chromatography eluted with EtOAc:petroleum ether=1:1 to afford the desired product as a yellow solid (17 g, 60%). $^1$H NMR (300 MHz, DMSO-d$_6$): δ ppm 2.51 (s, 3H), 3.17 (t, 4H, J=4.8 Hz). 3.76 (t, 4H, J=4.8 Hz), 5.55 (s, 2H), 7.10-7.13 (m, 2H), 7.28-7.37 (m, 3H), 7.57-7.61 (m, 2H); LC-MS: m/e=353 [M+1]$^+$.

b) 2-methyl-6-(4-morpholinyl)-1-(phenylmethyl)-1H-benzimidazol-4-amine

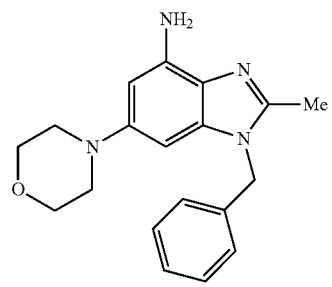 [SMILES: Cc1nc2c(N)cc(N3CCOCC3)cc2n1Cc1ccccc1]

To a solution of 2-methyl-6-(4-morpholinyl)-4-nitro-1-(phenylmethyl)-1H-benzimidazole (17 g) in EtOH (300 mL) was added watery Pd/C (8.7 g) and the mixture was stirred at 60° C. for 50 h under H$_2$ atmosphere (4 atm). The mixture was cooled to room temperature and filtered; the filtrate was concentrated in-vacuo. The residue was purified by silica gel chromatography eluted with EtOAc to afford the desired product as a white solid (7.4 g, 66%). $^1$H NMR (300 MHz, DMSO-d$_6$): δ ppm 2.37 (s, 3H), 2.96 (t, 4H, J=4.8 Hz), 3.72 (t, 4H, J=4.8 Hz), 4.94 (br s, 2H), 6.04-6.11 (m, 2H), 11.57 (br s, 1H); LC-MS: m/e=233 [M+1]$^+$ c) 4-bromo-2-methyl-6-(4-morpholinyl)-1H-benzimidazole To a solution of 2-methyl-6-(4-morpholinyl)-1-(phenylmethyl)-1H-benzimidazol-4-amine (2.3 g, 10 mmol) in aqueous HBr (50 mL) was added a solution of NaNO$_2$ (720 mg, 10.5 mmol) in water (10 mL) dropwise at 0-5° C. After addition the mixture was stirred at 0° C. for minutes, another solution of NaBr (3.1 g, 30 mmol) in aqueous HBr (50 mL) was added dropwise at 60° C. The resulting mixture was then heated to 80° C. for 30 minutes and then cooled to room temperature. It was neutralized with aqueous 2N NaOH and extracted with EtOAc (100 mL×3). The combined organic layers were concentrated in-vacuum and the residue was purified by silica gel chromatography eluted with petroleum ether:EtOAc=1:1 to give the desired product (1.7 g, 58%) as a white solid. $^1$H NMR (300 MHz, DMSO-d$_6$): δ ppm 2.44 (s, 3H), 3.07 (t, 4H, J=4.8 Hz), 3.74 (t, 4H, J=4.8 Hz), 6.85 (d, 1H, J=1.8 Hz), 7.04 (d, 1H, J=1.8 Hz), 12.20 (br s, 1H); LC-MS: m/e=296 [M+1]$^+$

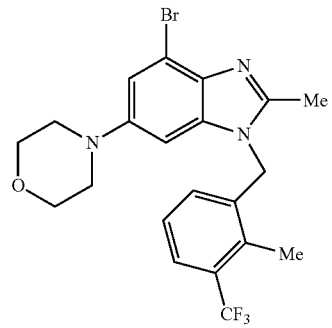 [SMILES: Cc1c(Cn2c(C)nc3c(Br)cc(N4CCOCC4)cc32)cccc1C(F)(F)F]

Preparation of 4-bromo-2-methyl-1-{[2-methyl-3-(trifluoromethyl)phenyl]methyl}-6-(4-morpholinyl)-1H-benzimidazole A suspension of 4-bromo-2-methyl-6-(4-morpholinyl)-1H-benzimidazole, prepared as described in Example 62 (500 mg, 1.688 mmol) and potassium carbonate (700 mg, 5.06 mmol) in N,N-Dimethylformamide (DMF) (6 mL) was stirred at rt for 15 min. 1-(bromomethyl)-2-methyl-3-(trifluoromethyl)benzene (641 mg, 2.53 mmol) was added in and the resulting reaction mixture was stirred for 3 h at 80° C. It was then cooled to room temperature and poured into ice/water. The precipitate was collected by filtration, washed with water, then few mLs of hexanes and air dried. The crude material was purified on a silica gel column (ISCO, 0-80% EtOAc in hexanes) to the desired product (565 mg, 1.182 mmol, 70.0% yield). $^1$H NMR (400 MHz, CHLOROFORM-d) δ ppm 7.59 (d, J=7.83 Hz, 1H), 7.16 (d, J=2.02 Hz, 1H), 7.10-7.15 (m, 1H), 6.46-6.52 (m, 2H), 5.25 (s, 2H), 3.75-3.89 (m, 4H), 3.05-3.14 (m, 4H), 2.55 (s, 3H), 2.51 (s, 3H). MS (ES+) m/e 468.9 [M+H]$^+$.

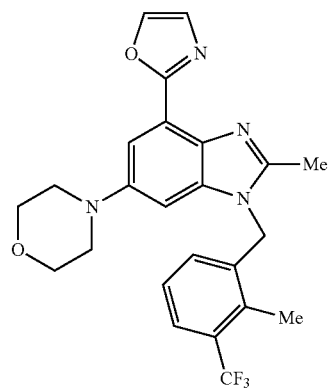 [SMILES: Cc1c(Cn2c(C)nc3c(-c4ncco4)cc(N4CCOCC4)cc32)cccc1C(F)(F)F]

Preparation of 2-methyl-1-{[2-methyl-3-(trifluoromethyl)phenyl]methyl}-6-(4-morpholinyl)-4-(1,3-oxazol-2-yl)-1H-benzimidazole A mixture of 4-bromo-2-methyl-1-{[2-methyl-3-(trifluoromethyl)phenyl]methyl}-6-(4-morpholinyl)-1H-benzimidazole (150 mg, 0.320 mmol), prepared as described in Example 63, 2-(tributylstannanyl)-1,3-oxazole (195 mg, 0.545 mmol) and Pd(Ph$_3$P)$_2$Cl$_2$ (11.27 mg, 0.016 mmol) in Tetrahydrofuran (THF) (5 mL) was stirred at reflux temperature for 19 h. Conversion to the desired product is observed by LC/MS analysis, but the majority of the mixture is still SM. The reaction mixture was transferred in a microwavable vial and irradiated in a microwave reactor at 120° C. for 90 min. The reaction mixture was diluted with EtOAc and CHCl$_3$, washed with aq sat sol NH$_4$Cl, brine, dried over Na$_2$SO$_4$ and the solvent was evaporated under reduced pressure. The residue was purified on a silica gel column (ISCO, 0-70% EtOAc in Hexanes—no product peak observed—then 0-10% MeOH in CH$_2$Cl$_2$) to give desired product (94.8 mg, 0.204 mmol, 63.5% yield) as a yellow powder. $^1$H NMR (400 MHz, CHLOROFORM-d) δ ppm 7.87 (s, 1H), 7.71 (d, J=2.27 Hz, 1H), 7.58 (d, J=7.83 Hz, 1H), 7.37 (s, 1H), 7.11 (t, J=7.83 Hz, 1H), 6.66 (d, J=2.27 Hz, 1H), 6.47 (d, J=7.83 Hz, 1H), 5.31 (s, 2H), 3.81-3.92 (m, 4H), 3.11-3.24 (m, 4H), 2.58 (s, 3H), 2.56 (s, 3H). MS (ES+) m/e 457.1 [M+H]$^+$

Example 65

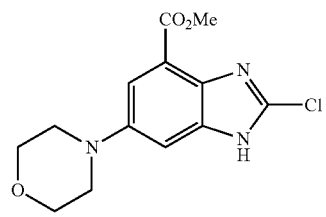 [SMILES: COC(=O)c1cc(N2CCOCC2)cc2[nH]c(Cl)nc12]

Preparation of methyl 2-chloro-5-(4-morpholinyl)-1H-benzimidazole-7-carboxylate a) methyl 6-(4-morpholinyl)-2-oxo-2,3-dihydro-1H-benzimidazole-4-carboxylate

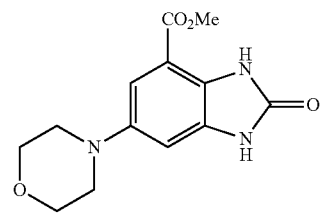 [SMILES: COC(=O)c1cc(N2CCOCC2)cc2[nH]c(=O)[nH]c12]

To a solution of methyl 2,3-diamino-5-(4-morpholinyl)benzoate, prepared as described in Example 45, step a (11.0 g, 4.0 mmol) in DMF (50 mL) was added urea (720 mg, 12 mmol) and the mixture was heated to 170° C. for 4 h. When analysis by TLC showed no starting material remaining, the mixture was cooled to room temperature then diluted with DCM (200 mL), washed with water (50 mL×2) and dried over anhydrous Na$_2$SO$_4$, filtered and concentrated in-vacuo. The residue was then purified by chromatography on silica (eluted with EtOAc) to afford the desired product as a dark-yellow solid (690 mg, 62%). $^1$H NMR (300 MHz, DMSO-d$_6$): δ ppm 3.02 (t, 4H, J=4.8 Hz), 3.74 (t, 4H, J=4.8 Hz), 3.86 (s, 3H), 6.82 (d, 1H, J=2.1 Hz), 6.99 (d, 1H, J=2.1 Hz), 10.48 (s, 1H), 10.82 (s, 1H). LC-MS: m/e=278 [M+1]$^+$.

b) methyl 2-chloro-5-(4-morpholinyl)-1H-benzimidazole-7-carboxylate

To a solution of combined batches of methyl 6-(4-morpholinyl)-2-oxo-2,3-dihydro-1H-benzimidazole-4-carboxylate (6.8 g, 24.5 mmol) in POCl$_3$ (25 mL) was added N,N-Dimethylaniline (8.8 g, 73.5 mmol) and the mixture was heated to 103° C. for 12 h. When TLC analysis showed no starting material remaining, the mixture was cooled to room temperature, purified by chromatography (eluted with petroleum ether/EtOAc=1/1) on silica to afford the desired product as a off-white solid (1.6 g, 23%). $^1$H NMR (300 MHz, DMSO-d$_6$): δ ppm 3.11 (t, 4H, J=4.5 Hz), 3.77 (t, 4H, J=4.5 Hz), 3.93 (s, 3H), 7.43 (d, 1H, J=1.8 Hz), 7.50 (d, 1H, J=1.8 Hz), 12.97 (s, 1H). LC-MS: m/e=296 [M+1]$^+$.

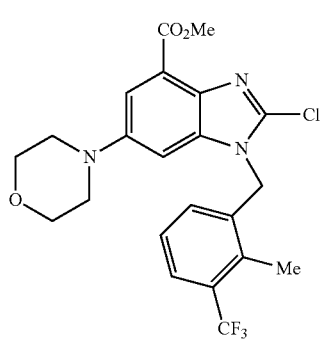 [SMILES: COC(=O)c1cc(N2CCOCC2)cc2c1nc(Cl)n2Cc1cccc(C(F)(F)F)c1C]

Preparation of methyl 2-chloro-1-{[2-methyl-3-(trifluoromethyl)phenyl]methyl}-6-(4-morpholinyl)-1H-benzimidazole-4-carboxylate To the mixture of methyl 2-chloro-5-(4-morpholinyl)-1H-benzimidazole-7-carboxylate, prepared as described in Example 65 (0.5 g, 1.691 mmol) in N,N-Dimethylformamide (DMF) (10 ml) was added in potassium carbonate (0.467 g, 3.38 mmol) and 1-(bromomethyl)-2-methyl-3-(trifluoromethyl)benzene (0.428 g, 1.691 mmol). The reaction mixture was stirred at 80° C. for 1 h. The reaction was cooled down. Water (100 mL) was added in. The solid precipitated. Filtration gave the solid which was purified on a silica column (20~60% EtOAc/Hexane) to give the product as white solid (0.66 g, 83%). $^1$H NMR (400 MHz, DMSO-d$_6$) δ ppm 2.54 (s, 3H) 3.07-3.16 (m, 4H) 3.68-3.78 (m, 4H) 3.91 (s, 3H) 5.63 (s, 2H) 6.41 (d, J=7.83 Hz, 1H) 7.28 (t, J=7.83 Hz, 1H) 7.39 (d, J=2.27 Hz, 1H) 7.50 (d, J=2.53 Hz, 1H) 7.63 (d, 1H). MS (ES+) m/e 468.0 [M+H]$^+$.

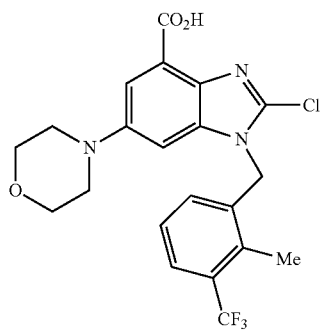 [SMILES: Cc1c(Cn2c(Cl)nc3c(C(=O)O)cc(N4CCOCC4)cc32)cccc1C(F)(F)F]

Preparation of 2-chloro-1-{[2-methyl-3-(trifluoromethyl)phenyl]methyl}-6-(4-morpholinyl)-1H-benzimidazole-4-carboxylic acid A mixture of methyl 2-chloro-1-{[2-methyl-3-(trifluoromethyl)phenyl]methyl}-6-(4-morpholinyl)-1H-benzimidazole-4-carboxylate, prepared as described in Example 66 (0.6 g, 1.282 mmol) in Tetrahydrofuran (THF) (10 mL) was added in 2 N lithium hydroxide (6.41 mL, 12.82 mmol). The reaction mixture was stirred at 50 C for 70 min. The reaction was cooled down. The organic solvent was removed in-vacuo. The aqueous mixture was acidified using 1 N HCl. The solid precipitated. Filtration and washing with water gave the product as white solid (0.55 g, 90%). $^1$H NMR (400 MHz, DMSO-d$_6$) d ppm 2.54 (s, 3H) 3.05-3.16 (m, 4H) 3.67-3.78 (m, 4H) 5.63 (s, 2H) 6.43 (d, J=7.83 Hz, 1H) 7.28 (t, J=7.83 Hz, 1H) 7.36 (d, J=2.27 Hz, 1H) 7.49 (d, J=2.53 Hz, 1H) 7.63 (d, J=8.08 Hz, 1H) 12.90 (s, 1H). MS (ES+) m/e 453.9 [M+H]$^+$.

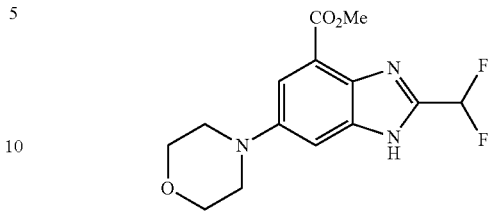

Preparation of methyl 2-(difluoromethyl)-5-(4-morpholinyl)-1H-benzimidazole-7-carboxylate a) methyl 2,3-diamino-5-morpholinobenzoate

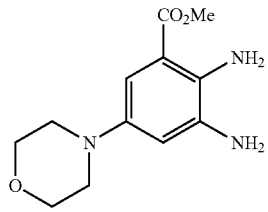 [SMILES: COC(=O)c1cc(N2CCOCC2)cc(N)c1N]

To a mixture of intermediate methyl 3-amino-5-(4-morpholinyl)-2-nitrobenzoate, prepared as described in Example 26, step c (98 g, 0.35 mol) in MeOH (2.2 L) was added Pd/C (9.8 g, 10%) and the resulting mixture was then stirred at room temperature under H$_2$ (4 atm) atmosphere. After stirring for 16 h, it was filtered and concentrated in vacuum to give the crude product (84.4 g, 96%) as a dark solid. $^1$H NMR (300 MHz, DMSO-d$_6$): δ ppm 2.85 (t, 4H, J=4.8 Hz), 3.70 (t, 4H, J=4.8 Hz), 3.76 (s, 3H), 4.77 (br. S, 2H), 5.86 (br. S, 2H), 6.54 (d, 1H, J=2.7 Hz), 6.61 (d, 1H, J=2.7 Hz); LC-MS: m/e=252 [M+1]$^+$ b) methyl 2-(difluoromethyl)-5-(4-morpholinyl)-1H-benzimidazole-7-carboxylate A mixture of methyl 2,3-diamino-5-morpholinobenzoate (40.16 g, 160 mmol) and 2,2-difluoroacetic acid (46.08 g, 480 mmol) in toluene (500 mL) was stirred at reflux temperature for 15 h. Then the mixture was cooled to room temperature and the solvent was removed in vacuum. The residue was purified by silica gel chromatography eluted with petroleum ether:EtOAc=2:1 to afford the desired product. Then, it was dissolved with EtOAc (2 L) and washed with aqueous NaHCO$_3$ (1 L) and brine (1 L). The organic layer was dried over anhydrous Na$_2$SO$_4$ and concentrated to give the desired product (40.9 g, 82%) as a yellow solid. $^1$H NMR showed this compound is in a form of tautomeric mixture (major tautomer/minor tautomer=5/1) $^1$H NMR of the major tautomer (300 MHz, DMSO-d$_6$): δ ppm 3.14 (t, 4H, J=4.8 Hz), 3.78 (t, 4H, J=4.8 Hz), 3.96 (s, 3H), 7.21 (t, 1H, J=52.8 Hz), 7.55 (d, 1H, J=2.4 Hz), 7.65 (d, 1H, J=2.4 Hz), 12.92 (s, 1H); LC-MS: m/e=312 [M+1]$^+$

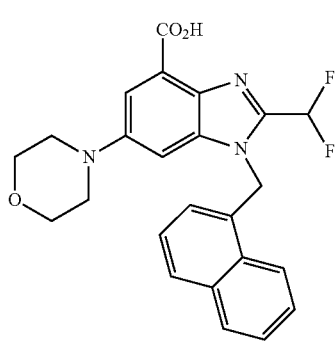 [SMILES: O=C(O)c1cc(N2CCOCC2)cc2c1nc(C(F)F)n2Cc1cccc2ccccc12]

Preparation of 2-(difluoromethyl)-6-(4-morpholinyl)-1-(1-naphthalenylmethyl)-1H-benzimidazole-4-carboxylic acid a) methyl 2-(difluoromethyl)-6-morpholino-1-(naphthalen-1-ylmethyl)-1H-benzo[d]imidazole-4-carboxylate

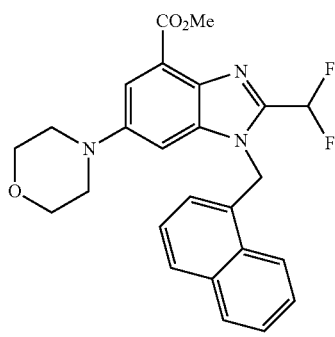 [SMILES: COC(=O)c1cc(N2CCOCC2)cc2c1nc(C(F)F)n2Cc1cccc2ccccc12]

A mixture of methyl 2-(difluoromethyl)-5-(4-morpholinyl)-1H-benzimidazole-7-carboxylate, prepared as described in Example 68 (500 mg, 1.6 mmol), K$_2$CO$_3$ (442 mg, 3.2 mmol) and 1-(bromomethyl)naphthalene (426 mg, 1.9 mmol) in DMF (15 mL) was stirred at 70° C. for 18 h. The reaction mixture was cooled to room temperature and filtered. The liquid was poured into water (100 mL) and filtered, the filter cake was collected and purified by silica gel chromatography eluted with petroleum ether:EtOAc=1:1 to give the desired product (710 mg, 98%) as a yellow solid. $^1$H NMR (300 MHz, DMSO-d$_6$): δ ppm 3.08 (t, 4H, J=4.5 Hz), 3.68 (t, 4H, J=4.5 Hz), 3.94 (s 3H), 6.21 (s, 2H), 6.27 (d, 1H, J=6.9 Hz), 7.21-7.38 (m, 3H), 7.56-7.69 (m, 3H), 7.84 (d, 1H, J=8.4 Hz), 8.00 (d, 1H, J=8.4 Hz), 8.24 (d, 1H, J=8.7 Hz); LC-MS: m/e=452 [M+1]$^+$ b) 2-(difluoromethyl)-6-(4-morpholinyl)-1-(1-naphthalenylmethyl)-1H-benzimidazole-4-carboxylic acid A mixture methyl 2-(difluoromethyl)-6-morpholino-1-(naphthalen-1-ylmethyl)-1H-benzo[d]imidazole-4-carboxylate (700 mg, 1.55 mmol) and 2N LiOH (5 mL) in THF (10 mL) was stirred at 45° C. for 4 h. It was filtered, the filter cake was dissolved in water (10 mL) and formic acid was added to adjust pH to 3-4. Then a filtration was performed and the filter cake was collected, dried under vacuum to give the product (450 mg, 66%) as a white solid. $^1$H NMR (300 MHz, DMSO-d$_6$): δ ppm 3.07 (s, 4H), 3.68 (s, 4H, s), 6.20 (s, 2H), 6.30 (d, 1H, J=7.2 Hz), 7.20-7.72 (m, 6H), 7.85 (d, 1H, J=8.1 Hz), 8.01 (d, 1H, J=7.8 Hz), 8.24 (d, 1H, J=7.5 Hz); LC-MS: m/e=438 [M+1]$^+$ Example 70

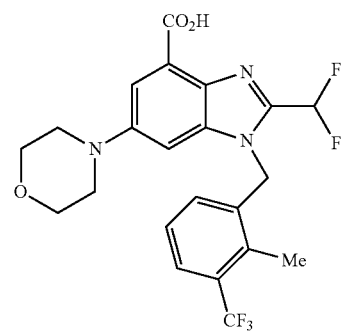 [SMILES: Cc1c(Cn2c(C(F)F)nc3c(C(=O)O)cc(N4CCOCC4)cc32)cccc1C(F)(F)F]

Preparation of 2-(difluoromethyl)-1-{[2-methyl-3-(trifluoromethyl)phenyl]methyl}-6-(4-morpholinyl)-1H-benzimidazole-4-carboxylic acid a) methyl 2-(difluoromethyl)-1-(2-methyl-3-(trifluoromethyl)benzyl)-6-morpholino-1H-benzo[d]imidazole-4-carboxylate

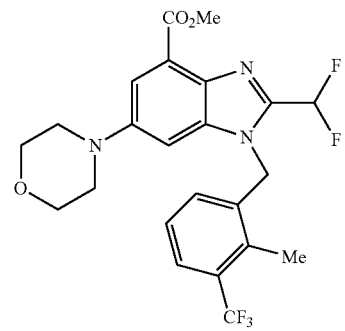 [SMILES: COC(=O)c1cc(N2CCOCC2)cc2c1nc(C(F)F)n2Cc1cccc(C(F)(F)F)c1C]

A mixture of methyl 2-(difluoromethyl)-5-(4-morpholinyl)-1H-benzimidazole-7-carboxylate, prepared as described in Example 68 (500 mg, 1.6 mmol), K$_2$CO$_3$ (442 mg, 3.2 mmol) and 1-(bromomethyl)-2-methyl-3-(trifluoromethyl)benzene (480 mg, 1.9 mmol) in DMF (15 mL) was stirred at 70° C. for 18 h. The reaction mixture was cooled to room temperature and filtered. The filtrate was poured into water (100 mL) and filtered, the filter cake was collected and purified by silica gel chromatography eluted with petroleum ether:EtOAc=1:1 to give the desired product (710 mg, 98%) as a yellow solid. $^1$H NMR (300 MHz, DMSO-d$_6$): δ ppm 2.53 (s, 3H), 3.14 (t, 4H, J=4.5 Hz), 3.73 (t, 4H, J=4.5 Hz), 3.93 (s, 3H), 5.75 (s, 2H), 6.27 (d, 1H, J=7.8 Hz), 7.22 (t, 1H, J=7.8 Hz), 7.30 (d, 1H, J=2.1 Hz), 7.36 (t, 1H, J=51.6 Hz), 7.58-7.61 (m, 2H); LC-MS: m/e=484 [M+1]$^+$ b) 2-(difluoromethyl)-1-{[2-methyl-3-(trifluoromethyl)phenyl]methyl}-6-(4-morpholinyl)-1H-benzimidazole-4-carboxylic acid A mixture of methyl 2-(difluoromethyl)-1-(2-methyl-3-(trifluoromethyl)benzyl)-6-morpholino-1H-benzo[d]imidazole-4-carboxylate (700 mg, 1.45 mmol) and 2 N LiOH (5 mL) in THF (10 mL) was stirred at 45° C. for 4 h. It was filtered, the filter cake was dissolved in water (10 mL) and formic acid was added to adjust pH=3-4. Then a filtration was performed and the filter cake was dried under vacuum to give the desired product (400 mg, 59%) as a white solid. $^1$H NMR (300 MHz, DMSO-$d_6$): δ ppm 2.53 (s, 3H), 3.13 (s, 4H), 3.73 (s, 4H), 5.75 (s, 2H), 6.29 (d, 1H, J=7.5 Hz), 7.19-7.61 (m, 5H), 12.97 (br s, 1H); LC-MS: m/e=470 [M+1]$^+$ (1350 mg, 2.88 mmol) and 2 N LiOH (10 mL) in THF (20 mL) was stirred at 45° C. for 4 h. It was filtered, the filter cake was dissolved in water (10 mL) and formic acid was added to adjust pH=3-4. Then a filtration was performed and the filter cake was dried under vacuum to give the desired product (600 mg, 46%) as a white solid. $^1$H NMR (300 MHz, DMSO-$d_6$): δ ppm 3.15 (s, 4H), 3.73 (s, 4H), 5.76 (s, 2H), 6.22 (d, 1H, J=7.5 Hz), 7.20-7.60 (m, 5H), 12.98 (br s, 1H); LC-MS: m/e=456 [M+1]$^+$

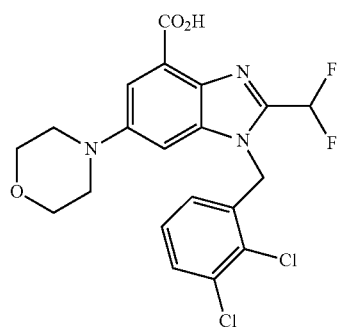 [SMILES: O=C(O)c1cc(N2CCOCC2)cc2c1nc(C(F)F)n2Cc1cccc(Cl)c1Cl]

Preparation of 1-[(2,3-dichlorophenyl)methyl]-2-(difluoromethyl)-6-(4-morpholinyl)-1H-benzimidazole-4-carboxylic acid a) methyl 1-(2,3-dichlorobenzyl)-2-(difluoromethyl)-6-morpholino-1H-benzo[d]imidazole-4-carboxylate

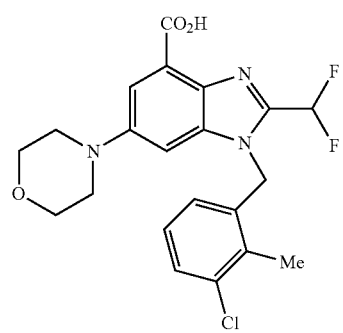

Preparation of 1-[(3-chloro-2-methylphenyl)methyl]-2-(difluoromethyl)-6-(4-morpholinyl)-1H-benzimidazole-4-carboxylic acid a) methyl 1-(2,3-dichlorobenzyl)-2-(difluoromethyl)-6-morpholino-1H-benzo[d]imidazole-4-carboxylate

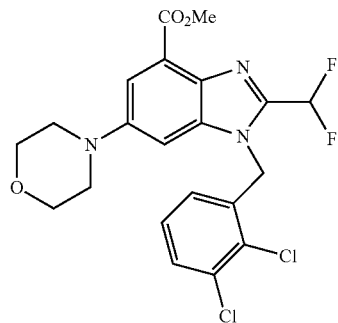 [SMILES: COC(=O)c1cc(N2CCOCC2)cc2c1nc(C(F)F)n2Cc1cccc(Cl)c1Cl]

A mixture of methyl 2-(difluoromethyl)-5-(4-morpholinyl)-1H-benzimidazole-7-carboxylate, prepared as described in Example 68 (1000 mg, 3.2 mmol), K$_2$CO$_3$ (884 mg, 6.4 mmol) and 1-(bromomethyl)-2,3-dichlorobenzene (926 mg, 3.8 mmol) in DMF (30 mL) was stirred at 70° C. for 18 h. The reaction mixture was cooled to room temperature and filtered. The filtrate was poured into water (100 mL) and filtered, the filter cake was collected and purified by silica gel chromatography eluted with petroleum ether:EtOAc=1:1 to give the desired product (1.4 g, 93%) as a yellow solid. $^1$H NMR (300 MHz, DMSO-$d_6$): δ ppm 3.16 (s, 4H), 3.74 (s, 4H), 3.92 (s, 3H), 5.77 (s, 2H), 6.21 (d, 1H, J=7.5 Hz), 7.20-7.58 (m, 5H); LC-MS: m/e=470 [M+1]$^+$ b) 1-[(2,3-dichlorophenyl)methyl]-2-(difluoromethyl)-6-(4-morpholinyl)-1H-benzimidazole-4-carboxylic acid A mixture of methyl 1-(2,3-dichlorobenzyl)-2-(difluoromethyl)-6-morpholino-1H-benzo[d]imidazole-4-carboxylate

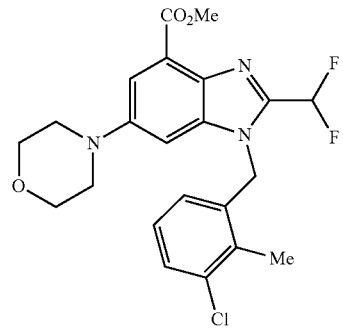 [SMILES: COC(=O)c1cc(N2CCOCC2)cc2c1nc(C(F)F)n2Cc1cccc(Cl)c1C]

A mixture of methyl 2-(difluoromethyl)-5-(4-morpholinyl)-1H-benzimidazole-7-carboxylate, prepared as described in Example 68 (1.18 g, 3.8 mmol), K$_2$CO$_3$ (2.48 g, 7.6 mmol) and 1-(bromomethyl)-3-chloro-2-methylbenzene (1 g, 4.6 mmol) in DMF (40 mL) was stirred at 70° C. for 18 h. The reaction mixture was cooled to room temperature and filtered. The filtrate was poured into water (100 mL) and filtered, the filter cake was collected and purified by silica gel chromatography eluted with petroleum ether:EtOAc=1:1 to give the desired product (1.18 g, 69%) as a yellow solid. $^1$H NMR (300 MHz, DMSO-$d_6$): δ ppm 2.46 (s, 3H), 3.13 (t, 4H, J=4.8 Hz), 3.73 (t, 4H, J=4.8 Hz), 3.92 (s, 3H), 5.70 (s, 2H), 5.97 (d, 1H, J=7.5 Hz), 7.04 (t, 1H, J=7.5 Hz), 7.26 (d, 1H, J=1.8 Hz), 7.34 (t, 1H, J=7.5 Hz), 7.35 (t, 1H, J=51.6 Hz), 7.58 (d, 1H, J=1.8 Hz); LC-MS: m/e=450 [M+1]$^+$ b) 1-[(3-chloro-2-methylphenyl)methyl]-2-(difluoromethyl)-6-(4-morpholinyl)-1H-benzimidazole-4-carboxylic acid A solution of methyl 1-(2,3-dichlorobenzyl)-2-(difluoromethyl)-6-morpholino-1H-benzo[d]imidazole-4-carboxylate (1045 mg, 2.3 mmol) in THF (40 mL) was added into 2 N LiOH (20 mL) and the mixture was stirred at 45° C. for 4 h. It was filtered, the filter cake was added to water (100 mL) and formic acid was added to adjust pH=3. Then a filtration was performed, the filter cake was collected and washed with water (200 mL), dried under vacuum to give the desired product (800 mg, 80%) as a yellow solid. $^1$H NMR (300 MHz, DMSO-$d_6$): δ ppm 2.46 (s, 3H), 3.13 (t, 4H, J=4.8 Hz), 3.73 (t, 4H, J=4.8 Hz), 3.92 (s, 3H), 5.70 (s, 2H), 6.00 (d, 1H, J=7.5 Hz), 7.04 (t, 1H, J=7.5 Hz), 7.23 (d, 1H, J=1.8 Hz), 7.34 (t, 1H, J=7.5 Hz), 7.36 (t, 1H, J=51.9 Hz), 7.57 (d, 1H, J=1.8 Hz), 12.96 (br s, 1H); LC-MS: m/e=436 [M+1]$^+$

Example 73

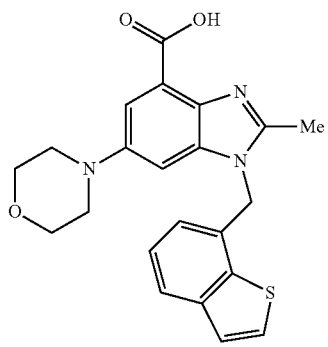 [SMILES: Cc1nc2c(C(=O)O)cc(N3CCOCC3)cc2n1Cc1cccc2ccsc12]

Preparation of 1-(1-benzothien-7-ylmethyl)-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 7-(bromomethyl)-1-benzothiophene (0.247 g, 1.090 mmol) and potassium carbonate (0.301 g, 2.179 mmol). The resulting reaction mixture was stirred for 3 h at 80° C. An additional amount of 7-(bromomethyl)-1-benzothiophene (0.247 g, 1.090 mmol) was added and mixture was stirred for 3 h at 80° C. The solution was cooled to room temperature and poured into water and extracted with EtOAc. The combined organic phase was washed with brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was found to be incomplete so the solution was neutralized with 1M HCl and evaporated. The residue was dissolved in 5 mL of methanol and treated with 1N NaOH for 2 h at 50° C., which resulted in a complete reaction. The reaction was cooled to room temperature and the organic solvent was removed in vacuo. The solution was diluted with water (20 mL) and acidified with 1 N HCl. The mixture was then filtered and the yellow solid was isolated. The aqueous layer was found to contain a significant amount of product and was evaporated. Both solid and residue were purified by reversed phase chromatography with a gradient of acetonitrile (0.1% TFA) and water (0.1% TFA v/v) (10-45%) over 10 minutes. The appropriate fractions were collected and evaporated to the desired product (27.9 mg, 0.068 mmol, 9.42% yield). $^1$H NMR (400 MHz, DMSO-$d_6$) δ ppm 2.76 (s, 3H) 3.14-3.21 (m, 4H) 3.71-3.76 (m, 4H) 6.01 (s, 2H) 7.06 (d, J=7.07 Hz, 1H) 7.36-7.44 (m, 1H) 7.56-7.62 (m, 2H) 7.71 (d, J=2.27 Hz, 1H) 7.83 (d, J=5.31 Hz, 1H) 7.92 (d, 1H). MS (ES+) m/e 408.1 [M+H]$^+$.

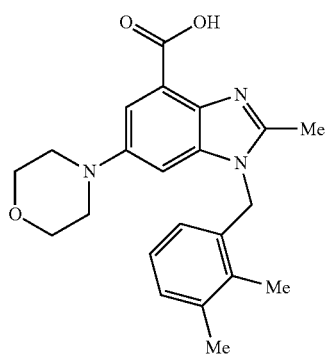 [SMILES: Cc1cccc(Cn2c(C)nc3c(C(=O)O)cc(N4CCOCC4)cc32)c1C]

Preparation of 1-[(2,3-dimethylphenyl)methyl]-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 2,3-dimethylbenzyl bromide (0.289 g, 1.453 mmol) and potassium carbonate (0.301 g, 2.179 mmol). The resulting reaction mixture was stirred for 3 h at 80° C. The solution was cooled to room temperature and poured into water and was extracted with EtOAc. The combined organic phase was washed with Brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in vacuo. The solution was diluted with water (20 mL) and acidified with 1 N HCl. The mixture was then filtered and the grey solid was purified by reversed phase HPLC with a gradient of acetonitrile (0.1% TFA) and water (0.1% TFA v/v) (20-50%) over 10 minutes. The appropriate fractions were collected and evaporated to yield the desired product (55.2 mg, 0.145 mmol, 20.02% yield). $^1$H NMR (400 MHz, CHLOROFORM-d) δ ppm 2.31 (s, 3H) 2.36 (s, 3H) 2.85 (s, 3H) 3.13-3.24 (m, 4H) 3.80-3.96 (m, 4H) 5.49-5.61 (m, 2H) 6.29-6.38 (m, 1H) 6.94-6.99 (m, 1H) 7.00-7.07 (m, 1H) 7.14-7.23 (m, 1H) 7.72 (m, 1H). MS (ES+) m/e 379.8 [M+H]$^+$.

101

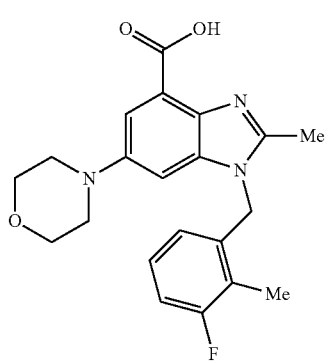 [SMILES: Cc1c(F)cccc1Cn1c(C)nc2c(C(=O)O)cc(N3CCOCC3)cc21]

Preparation of 1-[(3-fluoro-2-methylphenyl)methyl]-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 1-(bromomethyl)-3-fluoro-2-methylbenzene (0.295 g, 1.453 mmol) and potassium carbonate (0.301 g, 2.179 mmol). The resulting reaction mixture was stirred for 3 h at 80° C. The solution was cooled to room temperature and poured into water and was extracted with EtOAc. The combined organic phase was washed with Brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in vacuo. The solution was diluted with water (20 mL) and acidified with 1 N HCl. The mixture was then filtered and the grey solid was purified by reversed phase HPLC with a gradient of acetonitrile (0.1% TFA) and water (0.1% TFA v/v) (10-40%) over 10 minutes. The appropriate fractions were collected and evaporated to yield the desired product (62.7 mg, 0.164 mmol, 22.51% yield). $^1$H NMR (400 MHz, CHLOROFORM-d) δ ppm 2.36 (s, 3H) 2.87 (s, 3H) 3.07-3.20 (m, 4H) 3.81-3.92 (m, 4H) 5.55 (s, 2H) 6.29-6.38 (m, 1H) 6.85-6.90 (m, 1H) 7.03-7.17 (m, 2H) 7.55 (m, 1H). MS (ES+) m/e 383.8 [M+H]$^+$.

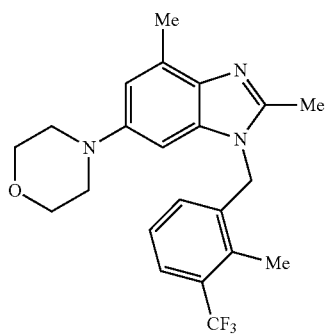 [SMILES: Cc1c(Cn2c(C)nc3c(C)cc(N4CCOCC4)cc32)cccc1C(F)(F)F]

102

Preparation of 2,4-dimethyl-1-{[2-methyl-3-(trifluoromethyl)phenyl]methyl}-6-(4-morpholinyl)-1H-benzimidazole A mixture of 4-bromo-2-methyl-1-{[2-methyl-3-(trifluoromethyl)phenyl]methyl}-6-(4-morpholinyl)-1H-benzimidazole, prepared as described in Example 62 (200 mg, 0.427 mmol), trimethylboroxine (0.239 mL, 1.708 mmol), Pd(Ph$_3$P)$_4$ (49.4 mg, 0.043 mmol) and potassium carbonate (118 mg, 0.854 mmol) in 1,4-Dioxane (2.5 mL)/Water (0.25 mL) was irradiated at 120° C. in a microwave synthesizer for 40 min, then cooled and poured into water. The mixture was extracted with ethyl acetate. The extracts were washed with brine, dried (Na$_2$SO$_4$) and evaporated under reduced pressure. The residue was purified by RP-HPLC (25-45% AcCN in water plus 0.1% TFA) to give the desired compound (77 mg, 0.181 mmol, 42.5% yield) as a white solid (contains 3-5% of the 4-H compound). $^1$H NMR (400 MHz, CHLOROFORM-d) δ ppm 7.58 (d, J=8.08 Hz, 1H), 7.12 (t, J=7.83 Hz, 1H), 6.80 (d, J=1.01 Hz, 1H), 6.51 (d, J=7.83 Hz, 1H), 6.40 (d, J=1.77 Hz, 1H), 5.26 (s, 2H), 3.78-3.91 (m, 4H), 3.01-3.15 (m, 4H), 2.67 (s, 3H), 2.56 (s, 3H), 2.50 (s, 3H). MS (ES+) m/e 404.1 [M+H]$^+$. (NOTE: The reaction was repeated using PdCl$_2$(dppf) as catalyst. Less (to negligible) reduction was observed).

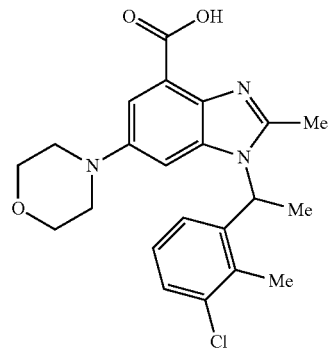 [SMILES: Cc1c(Cl)cccc1C(C)n1c(C)nc2c(C(=O)O)cc(N3CCOCC3)cc21]

Preparation of 1-[1-(3-chloro-2-methylphenyl)ethyl]-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 1-(1-bromoethyl)-3-chloro-2-methylbenzene (0.339 g, 1.453 mmol) and potassium carbonate (0.301 g, 2.179 mmol). The resulting reaction mixture was stirred for 3 h at 80° C. The solution was cooled to room temperature and poured into water and was extracted with EtOAc. The combined organic phase was washed with Brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in vacuo. The solution was diluted with water (20 mL) and acidified with 1 N HCl. The mixture was then filtered and the grey solid was purified by reversed phase HPLC with a gradient of acetonitrile (0.1% TFA) and water (0.1% TFA v/v) (20-50%) over 10 minutes. The appropriate fractions were collected and evaporated to yield the desired product (36.1 mg, 0.087 mmol, 12.01% yield). $^1$H NMR (400 MHz, CHLOROFORM-d) δ ppm 2.04-2.10 (m, 6H) 2.88 (s, 3H) 2.98-3.17 (m, 4H) 3.87 (s, 4H) 5.95-6.06 (m, 1H) 6.70-6.77 (m, 1H) 7.35-7.42 (m, 1H) 7.51-7.57 (m, 1H) 7.60-7.67 (m, 1H) 7.71-7.77 (m, 1H). MS (ES+) m/e 413.8 [M+H]$^+$.

Example 78

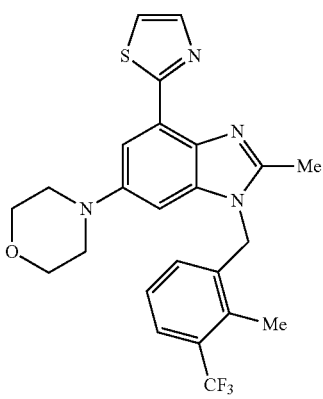 [SMILES: Cc1c(Cn2c(C)nc3c(-c4nccs4)cc(N4CCOCC4)cc32)cccc1C(F)(F)F]

Preparation of 2-methyl-1-{[2-methyl-3-(trifluoromethyl)phenyl]methyl}-6-(4-morpholinyl)-4-(1,3-thiazol-2-yl)-1H-benzimidazole A mixture of 4-bromo-2-methyl-1-{[2-methyl-3-(trifluoromethyl)phenyl]methyl}-6-(4-morpholinyl)-1H-benzimidazole, prepared as described in Example 62 (200 mg, 0.427 mmol), 2-thazolylzinc bromide (1.708 mL, 0.854 mmol) and Pd(Ph$_3$P)$_4$ (49.4 mg, 0.043 mmol) in Tetrahydrofuran (THF) (1.5 mL) was irradiated in a microwave reactor at 110° C. for 2.5 h. The reaction mixture was diluted with EtOAc and CHCl$_3$, washed with NH$_4$Cl aq sat sol, brine, dried over Na$_2$SO$_4$ and evaporated under reduced pressure. The residue was purified on silica gel (ISCO, 0-70% EtOAc in Hexanes, then 0-10% MeOH in CH$_2$Cl$_2$) to give the desired product (127 mg, 0.255 mmol, 59.8% yield) as a yellow powder. $^1$H NMR (400 MHz, CHLOROFORM-d) δ ppm 7.97 (d, J=3.28 Hz, 1H), 7.55 (d, J=3.54 Hz, 1H), 7.45 (d, J=7.83 Hz, 1H), 7.32 (d, J=2.02 Hz, 1H), 7.03 (t, J=7.83 Hz, 1H), 6.74 (d, J=1.77 Hz, 1H), 6.35 (d, J=7.83 Hz, 1H), 5.32 (s, 2H), 3.60-3.76 (m, 4H), 2.95-3.07 (m, 4H), 2.60 (s, 3H), 2.55 (s, 3H). MS (ES+) m/e 473.1 [M+H]$^+$.

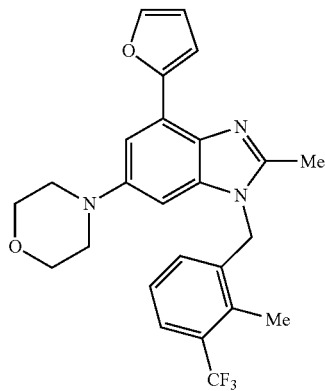 [SMILES: Cc1c(Cn2c(C)nc3c(-c4ccco4)cc(N4CCOCC4)cc32)cccc1C(F)(F)F]

Preparation of 4-(2-furanyl)-2-methyl-1-{[2-methyl-3-(trifluoromethyl)phenyl]methyl}-6-(4-morpholinyl)-1H-benzimidazole A mixture of 4-bromo-2-methyl-1-{[2-methyl-3-(trifluoromethyl)phenyl]methyl}-6-(4-morpholinyl)-1H-benzimidazole, prepared as described in Example 62 (200 mg, 0.427 mmol), 2-furanyl-boronic acid (71.7 mg, 0.641 mmol), PdCl$_2$(dppf)-CH$_2$Cl$_2$ adduct (34.9 mg, 0.043 mmol) and sodium carbonate (91 mg, 0.854 mmol) in 1,2-Dimethoxyethane (DME) (2.5 mL) and Water (0.5 mL) was irradiated in a microwave reactor for 1 h at 100° C. The mixture was poured into water and extracted with EtOAc. The organic phase was washed with brine, dried over Na$_2$SO$_4$ and evaporated. The residue was purified by RP-HPLC (Gilson, 25-65% Acetonitrile in water plus 0.1% TFA) to give the desired product (48.5 mg, 0.104 mmol, 24.43% yield) as a white powder (separation from impurity was difficult. The head of the peak was discarded decreasing the overall yield). $^1$H NMR (400 MHz, CHLOROFORM-d) δ ppm 7.51-7.63 (m, 3H), 7.42 (d, J=2.02 Hz, 1H), 7.12 (t, J=7.83 Hz, 1H), 6.60 (dd, J=3.28, 1.77 Hz, 1H), 6.51 (d, J=7.83 Hz, 1H), 6.49 (d, J=2.02 Hz, 1H), 5.28 (s, 2H), 3.80-3.94 (m, 4H), 3.12-3.22 (m, 4H), 2.56 (s, 3H), 2.53 (s, 3H). MS (ES+) m/e 456.0 [M+H]$^+$.

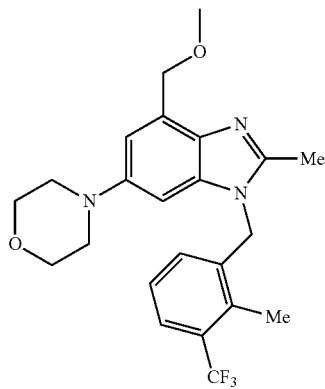 [SMILES: COCc1cc(N2CCOCC2)cc2c1nc(C)n2Cc1cccc(C(F)(F)F)c1C]

Preparation of 2-methyl-4-[(methyloxy)methyl]-1-{[2-methyl-3-[(trifluoromethyl)phenyl]methyl}-6-(4-morpholinyl)-1H-benzimidazole To the mixture of [2-methyl-1-{[2-methyl-3-(trifluoromethyl)phenyl]methyl}-6-(4-morpholinyl)-1H-benzimidazol- 4-yl]methanol, prepared as described in Example 43 (160 mg, 0.381 mmol) in N,N-Dimethylformamide (DMF) (15 mL), sodium hydride (30.5 mg, 0.763 mmol) was added in and followed by the addition of methyl iodide (0.048 mL, 0.763 mmol). The reaction was stirred at rt for 3 hours. More sodium hydride (30.5 mg, 0.763 mmol) and methyl iodide (0.048 mL, 0.763 mmol) was added in. The reaction was stirred at rt for another 2 hours then Water (70 mL) was added in. The mixture was extracted with EtOAc (100 mL). The organic phase was washed with Brine (100 mL), dried (MgSO$_4$) and concentrated. The crude was subjected to ISCO purification (0-2% MeOH/DCM) to give the product. $^1$H NMR (400 MHz, DMSO-d$_6$) δ ppm 2.36 (s, 3H) 2.54 (s, 3H) 3.00-3.07 (m, 4H) 3.37 (s, 3H) 3.68-3.75 (m, 4H) 4.76 (s, 2H) 5.52 (s, 2H) 6.32 (d, J=7.83 Hz, 1H) 6.88 (m, 2H) 7.25 (s, 1H) 7.60 (d, 1H). MS (ES+) m/e 434.4 [M+H]$^+$.

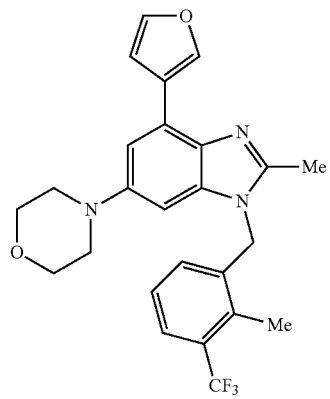 [SMILES: Cc1c(Cn2c(C)nc3c(-c4ccoc4)cc(N4CCOCC4)cc32)cccc1C(F)(F)F]

Preparation of 4-(3-furanyl)-2-methyl-1-{[2-methyl-3-(trifluoromethyl)phenyl]methyl}-6-(4-morpholinyl)-1H-benzimidazole A mixture of 4-bromo-2-methyl-1-{[2-methyl-3-(trifluoromethyl)phenyl]methyl}-6-(4-morpholinyl)-1H-benzimidazole, prepared as described in Example 62 (200 mg, 0.427 mmol), 3-furanyl boronic acid (47.8 mg, 0.427 mmol), sodium carbonate (91 mg, 0.854 mmol) and PdCl$_2$(dppf)-CH$_2$Cl$_2$ adduct (34.9 mg, 0.043 mmol) in 1,2-Dimethoxyethane (DME) (2.5 mL) and Water (0.5 mL) was irradiated in a microwave reactor for 1 h at 100° C. The mixture was poured into water and extracted with EtOAc. The organic phase was washed with brine, dried over Na$_2$SO$_4$ and evaporated. Only partial conversion (ca. 50%) was observed by LC/MS analysis. The residue was purified by RP-HPLC (Gilson, 25-65% Acetonitrile in water plus 0.1% TFA) to the desired product (28 mg, 0.060 mmol, 14.11% yield) as a white powder (separation from impurity was difficult. The head of the peak was discarded decreasing the overall yield, in addition to the partial conversion observed). $^1$H NMR (400 MHz, CHLOROFORM-d) δ ppm 8.57 (s, 1H), 7.58 (d, J=7.58 Hz, 1H), 7.55 (t, J=1.52 Hz, 1H), 7.09-7.15 (m, 2H), 7.02 (d, J=1.26 Hz, 1H), 6.52 (d, J=7.83 Hz, 1H), 6.48 (d, J=2.02 Hz, 1H), 5.29 (s, 2H), 3.80-3.97 (m, 4H), 3.07-3.21 (m, 4H), 2.57 (s, 3H), 2.52 (s, 3H). MS (ES+) m/e 456.0 [M+H]$^+$

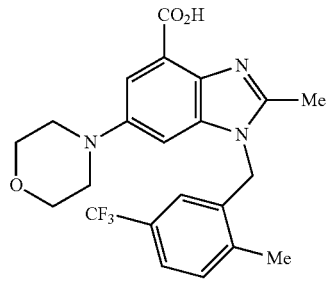 [SMILES: Cc1ccc(C(F)(F)F)cc1Cn1c(C)nc2c(C(=O)O)cc(N3CCOCC3)cc21]

Preparation of 2-methyl-1-{[2-methyl-5-(trifluoromethyl)phenyl]methyl}-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.3 g, 1.090 mmol) in N,N-Dimethylformamide (DMF) (10 mL) was added 2-methyl-5-(trifluoromethyl)benzyl bromide (0.552 g, 2.179 mmol) and potassium carbonate (0.452 g, 3.27 mmol). The resulting reaction mixture was stirred for 3 h at 80° C. The solution was cooled to room temperature and poured into water and was extracted with EtOAc. The combined organic phase was washed with Brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in vacuo. The solution was diluted with water (20 mL) and acidified with 1 N HCl. The mixture was then filtered and the grey solid was purified by reversed phase HPLC with a gradient of acetonitrile (0.1% TFA) and water (0.1% TFA v/v) (25-55%) over 10 minutes. The appropriate fractions were collected and evaporated to yield the desired product (120.1 mg, 0.277 mmol, 25.4% yield). $^1$H NMR (400 MHz, METHANOL-d$_4$) δ ppm 2.53 (s, 3H) 2.88 (s, 3H) 3.15-3.23 (m, 4H) 3.79-3.88 (m, 4H) 5.84 (s, 2H) 7.06 (s, 1H) 7.27 (d, J=2.27 Hz, 1H) 7.51-7.58 (m, 1H) 7.59-7.64 (m, 1H) 7.86 (d, 1H). MS (ES+) m/e 433.8 [M+H]$^+$.

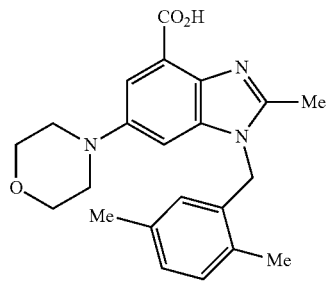 [SMILES: Cc1ccc(C)c(Cn2c(C)nc3c(C(=O)O)cc(N4CCOCC4)cc32)c1]

Preparation of 1-[(2,5-dimethylphenyl)methyl]-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 2,5-dimethylbenzyl bromide (0.289 g, 1.453 mmol) and potassium carbonate (0.301 g, 2.179 mmol). The resulting reaction mixture was stirred for 3 h at 80° C. The solution was cooled to room temperature and poured into water and was extracted with EtOAc. The combined organic phase was washed with Brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in vacuo. The solution was diluted with water (20 mL) and acidified with 1 N HCl. The mixture was then filtered and the grey solid was purified by reversed phase HPLC with a gradient of acetonitrile (0.1% TFA) and water (0.1% TFA v/v) (15-50%) over 10 minutes. The appropriate fractions were collected and evaporated to yield the desired product (96.4 mg, 0.254 mmol, 35.0% yield). $^1$H NMR (400 MHz, METHANOL-d$_4$) δ ppm 2.19 (s, 3H) 2.40 (s, 3H) 2.84 (s, 3H) 3.13-3.27 (m, 4H) 3.78-3.86 (m, 4H) 5.70 (s, 2H) 6.54 (s, 1H) 7.09 (d, J=7.83 Hz, 1H) 7.20 (d, J=7.58 Hz, 1H) 7.25 (d, J=2.27 Hz, 1H) 7.83 (d, 1H). MS (ES+) m/e 379.8 [M+H]$^+$.

Example 84

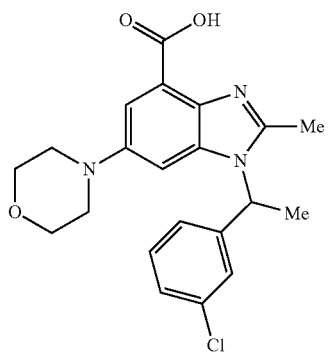 [SMILES: Cc1nc2c(C(=O)O)cc(N3CCOCC3)cc2n1C(C)c1cccc(Cl)c1]

Preparation of 1-[1-(3-chlorophenyl)ethyl]-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 1-(1-bromoethyl)-3-chlorobenzene (0.203 mL, 1.453 mmol) and potassium carbonate (0.301 g, 2.179 mmol). The resulting reaction mixture was stirred for 3 h at 80° C. The solution was cooled to room temperature and poured into water and was extracted with EtOAc. The combined organic phase was washed with Brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in vacuo. The solution was diluted with water (20 mL) and acidified with 1 N HCl. The mixture was then filtered and the grey solid was purified by reversed phase HPLC with a gradient of acetonitrile (0.1% TFA) and water (0.1% TFA v/v) (10-40%) over 10 minutes. The appropriate fractions were collected and evaporated to provide the desired product (70.5 mg, 0.176 mmol, 24.27% yield). $^1$H NMR (400 MHz, CHLOROFORM-d) δ ppm 2.04 (d, J=6.82 Hz, 3H) 2.78 (br. s., 4H) 3.02 (s, 3H) 3.78 (br. s., 4H) 5.95-6.06 (m, 1H) 6.49 (br. s., 1H) 7.35-7.51 (m, 3H) 7.57 (m, 1H). MS (ES+) m/e 399.8 [M+H]$^+$.

Example 85

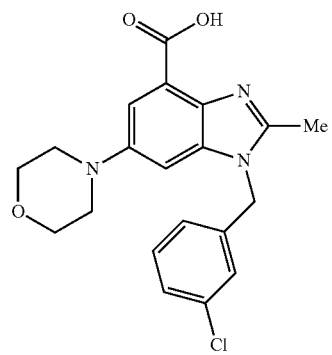 [SMILES: Cc1nc2c(C(=O)O)cc(N3CCOCC3)cc2n1Cc1cccc(Cl)c1]

Preparation of 1-[(3-chlorophenyl)methyl]-2-methyl-6-(4-morpholinyl)-1H-benzimidazole-4-carboxylic acid To a solution of methyl 2-methyl-5-(4-morpholinyl)-1H-benzimidazole-7-carboxylate, prepared as described in Example 26, step d (0.2 g, 0.726 mmol) in N,N-Dimethylformamide (DMF) (10 mL) was added 1-(bromomethyl)-3-chlorobenzene (0.190 mL, 1.453 mmol) and potassium carbonate (0.301 g, 2.179 mmol). The resulting reaction mixture was stirred for 3 h at 80° C. The solution was cooled to room temperature and poured into water and was extracted with EtOAc. The combined organic phase was washed with Brine and concentrated. The residue was purified on Biotage Isolera purification system using a Biotage 10 g SNAP silica gel cartridge and eluted with a gradient of DCM to 5% MeOH/DCM over 10 column volumes. The expected compound was collected and evaporated to yield a tan solid. The tan solid was dissolved in tetrahydrofuran (THF) (10.00 mL) followed by the addition of 1M lithium hydroxide solution (10 mL, 10 mmol). The reaction was stirred at 50° C. for 2 h. The reaction was cooled to room temperature and the organic solvent was removed in vacuo. The solution was diluted with water (20 mL) and acidified with 1 N HCl. The mixture was then filtered and a gray solid was isolated. The aqueous layer was found to contain a significant amount of product and was evaporated. Both solid and residue were purified by reversed phase HPLC with a gradient of acetonitrile (0.1% TFA) and water (0.1% TFA v/v) (5-50%) over 10 minutes. The appropriate fractions were collected and evaporated to procide the desired product (37.5 mg, 0.097 mmol, 13.38% yield). $^1$H NMR (400 MHz, CHLOROFORM-d) δ ppm 2.93 (br. s., 3H) 3.05 (br. s., 4H)

3.77-3.85 (m, 4H) 5.55 (br. s., 2H) 6.88 (s, 1H) 7.09 (br. s., 1H) 7.20 (s, 1H) 7.31-7.39 (m, 3H). MS (ES+) m/e 385.8 [M+H]+.

Example 86

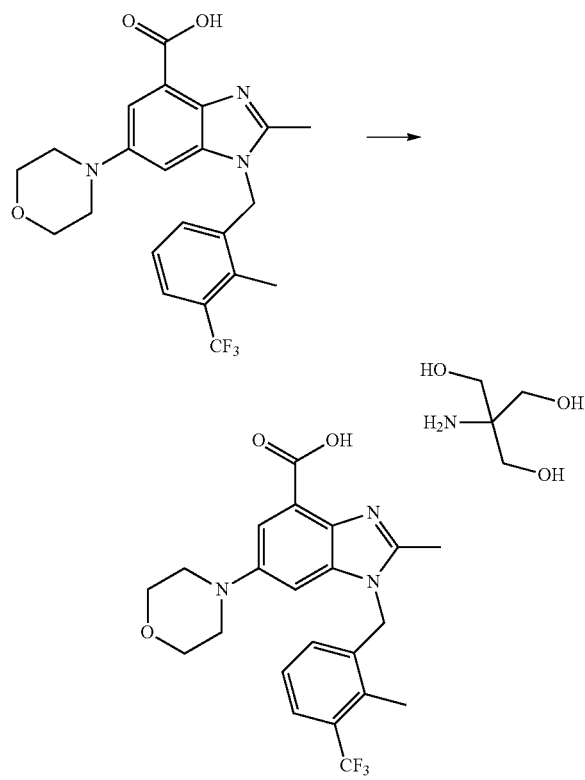

Preparation of 2-methyl-1-{[2-methyl-3-(trifluoromethyl)phenyl]methyl}-6-(4-morpholinyl)-1H-benzimidazole-4-carboxylic acid 2-amino-2-(hydroxymethyl)-1,3-propanediol Salt Seed Crystal Preparation—Batch 1:

To the 2-methyl-1-{[2-methyl-3-(trifluoromethyl)phenyl] methyl}-6-(4-morpholinyl)-1H-benzimidazole-4-carboxylic acid (52.9 mg, 0.122 mmol), methanol (2.0 mL) was added. To the slurry, tromethamine(2-amino-2-(hydroxymethyl)-1,3-propanediol) (3.0 M solution in water, 1.0 equivalent) was added. The slurry was heated to 60 C. and kept stirring at 60 C for 3 hours. The slurry was then cooled slowly (0.1 C/min) to 20 C. Once the temperature of the slurry reached 20 C, the slurry was kept stirring at 20 C for 8 hours. The crystalline solids were isolated by vacuum filtration. The yield of the desired salt was 57.2 mg (85% yield).

Seed Crystal Preparation—Batch 2:

To the 2-methyl-1-{[2-methyl-3-(trifluoromethyl)phenyl] methyl}-6-(4-morpholinyl)-1H-benzimidazole-4-carboxylic acid (353.0 mg), methanol (14.0 mL) was added. The slurry was heated to 60 C. and tromethamine (3.0 M solution in water, 1.0 equivalent) was added in four aliquots over 15 minutes followed by the addition of crystalline seeds of crystalline tromethamine salt from batch 1. The slurry was stirred at 60 C for 3 hours, cooled (1 C/min) to 20 C, and stirred at 20 C for 8 hours. The solids were isolated by vacuum filtration, dried at 60 C under vacuum for 5 hours. The yield of the tromethamine salt was 401.5 mg (~88.9% yield).

Batch 3:

2-methyl-1-{[2-methyl-3-(trifluoromethyl)phenyl]methyl}-6-(4-morpholinyl)-1H-benzimidazole-4-carboxylic acid (40.0 g, 92 mmol) was suspended in Methanol (1.6 L) in a 3 L rounded-bottom flask. The resulting slurry was heated to 60° C. mixing on a buchii rotary evaporator water bath and tris(hydroxymethyl)aminomethane (3M solution in water) (0.031 L, 92 mmol) was added in four aliquots over 15 minutes followed by the addition of seed crystals as produced by method analogous to Example 86, Batch 2, above (108 mg). This slurry was stirred (flask rotated on buchii rotovap) at 60° C. for 3 hours, then cooled (~1° C./min) to 20° C. (room temperature), then finally magnetically stirred at 20° C. (room temperature) for 8 hours. The resulting white solid was isolated by vacuum filtration, dried under vacuum at 60° C. for 8 hours to provide 2-methyl-1-{[2-methyl-3-(trifluoromethyl)phenyl]methyl}-6-(4-morpholinyl)-1H-benzimidazole-4-carboxylic acid-2-amino-2-(hydroxymethyl)-1,3-propanediol (1:1) (47.76 g, 86 mmol, 93% yield) as a white solid. Both proton NMR and LCMS are consistent with the proposed structure. $^1$H NMR (400 MHz, DMSO-d6) δ ppm 7.61 (d, J=7.83 Hz, 1H) 7.37 (d, J=2.27 Hz, 1H) 7.17-7.33 (m, 2H) 6.33 (d, J=7.83 Hz, 1H) 5.59 (s, 2H) 3.66-3.80 (m, 4H) 2.98-3.15 (m, 4H) 2.50-2.58 (m, 10H) 2.43 (s, 3H); LCMS m/z MH+=434.3.

Example 87

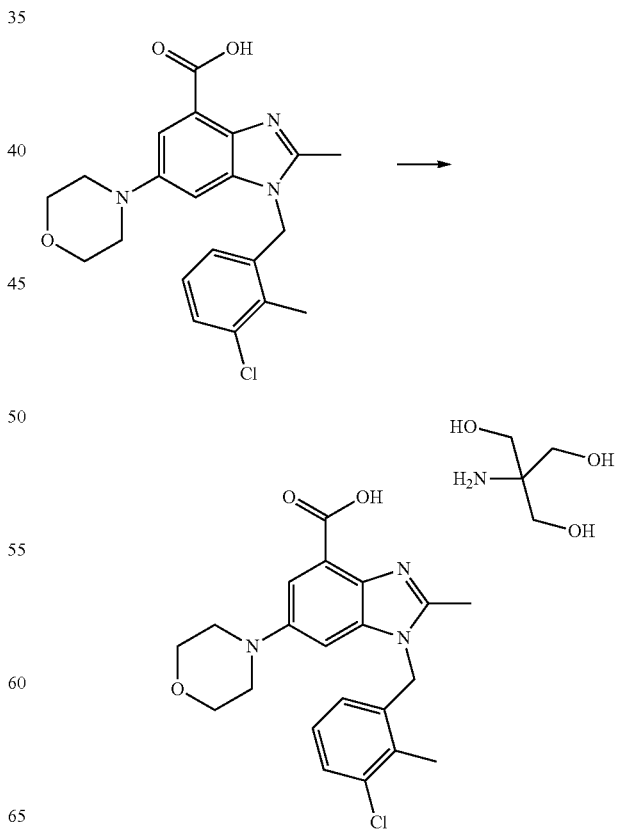

Preparation of 1-(3-(chloromethyl)-2-methylbenzyl)-2-methyl-6-morpholino-1H-benzo[d]imidazole-4-carboxylic acid, 2-amino-2-(hydroxymethyl)-1,3-propanediol Salt 1-(3-chloro-2-methylbenzyl)-2-methyl-6-morpholino-1H-benzo[d]imidazole-4-carboxylic acid (10 g, 25.01 mmol) was suspended in Methanol (400 mL) in a 1 L rounded-bottom flask. The resulting slurry was heated to 60° C. using a Buchii rotary evaporator water bath (no vacuum) and tris (hydroxymethyl)aminomethane (3M solution in water) (8.34 mL, 25.01 mmol) was added in four aliquots over 15 minutes. This slurry was stirred (flask rotated on Buchii rotovap) at 60° C. for 3 hours, then cooled (~1° C./min) to 20° C. (room temperature), then finally magnetically stirred at 20° C. (room temperature) for 15 hours. The resulting white solid was isolated by vacuum filtration, dried under vacuum at 65° C. for 18 hours to provide 1-(3-chloro-2-methylbenzyl)-2-methyl-6-morpholino-1H-benzo[d]imidazole-4-carboxylic acid, 2-Amino-2-(hydroxymethyl)-1,3-propanediol salt (11.1 g, 21.09 mmol, 84% yield) as a white solid. MS (ES+) m/e: 400.0, 402.0 [M+H]+. $^1$H NMR (400 MHz, DMSO-$d_6$) δ ppm 7.32-7.39 (m, 2H) 7.16 (d, J=2.27 Hz, 1H) 7.05 (t, J=7.96 Hz, 1H) 6.05 (d, J=7.58 Hz, 1H) 5.52 (s, 2H) 3.68-3.77 (m, 4H) 3.36 (s, 6H) 3.02-3.11 (m, 4H) 2.47 (s, 3H) 2.42 (s, 3H).

Biological Assays

Compounds of the present invention were tested according to the following assays and found as inhibitors of PI3 kinases, particularly PI3Kβ. The activities ($IC_{50}$) of exemplified compounds range from about 1 nM to about 10 µM against PI3Kβ. The majority of the compounds were under 500 nM; the most active compounds were under 10 nM. The $IC_{50}$ value can be converted and presented as $pIC_{50}$ value.

HTRF In Vitro Profiling Assays for PI3K Inhibition

The PI3-Kinase profiling assays were developed to measure the compound-dependent inhibition of the alpha, beta, delta, and gamma isoforms of PI3K in an in vitro catalytic assay. This assay was developed and optimized from a kit produced by Upstate (Millipore catalog #33-017). Briefly, this procedure utilizes a pre-formed HTRF (Homogeneous Time-Resolved Fluorescence energy transfer) complex between four binding partners: 1) biotinylated PIP3, 2) GST tagged pleckstrin homology (PH) domain, 3) Europium labeled anti-GST monoclonal antibody, and 4) Streptavidin-Allophycocyanin (APC). The native PIP3 produced by PI 3-Kinase activity displaces biotin-PIP3 from the PH domain, resulting in the dissociation of the HTRF complex and a decrease in the fluorescence signal. The format of this assay is the same for all 4 isoforms of PI3K; the differences lie in the concentration of enzyme used to achieve the most robust signal. The alpha and delta assays are run at 400 µM enzyme; the beta assay is at 200 µM enzyme and the gamma assay is run at 1 nM enzyme. In addition, the alpha, beta and delta assays are run with 150 mM NaCl while the gamma assay is run in the absence of NaCl. The ATP concentration is 100 uM in the alpha, beta, and delta assays and 15 uM ATP in the gamma assay. All reactions are run at 10 uM PIP2

Compounds were serially diluted (3-fold in 100% DMSO) across a 384-well polypropylene mother plate from column 1 to column 12 and column 13 to column 24, to yield 11 concentrations for each test compound. Columns 6 and 18 contain only DMSO. Once titrations were made, 0.05 µL was transferred to a 384-well low-volume assay plate (Greiner 784076). This assay plate contained three pharmacological controls (known PI3K inhibitors) and 3 assay controls: (1) Enzyme without inhibitor; (2) Buffer minus enzyme, and (3) Buffer minus enzyme plus native PIP3. DMSO was stamped into all wells of columns 6 and 18. PIP3 was added at 40 µM in 1× Reaction buffer (1 µL of 200 µM PIP3) to alternating rows of column 18 (wells 18 B, D, F, H, J, L, N, P). The no-enzyme control reactions were run in wells 18 A, C, E, G, I, K, M, O (0.1 µL of 100% DMSO).

The PI3-Kinase profiling assay was optimized using the HTRF kit provided by Upstate (Millipore). The assay kit contained seven reagents: 1) 4× Reaction Buffer; 2) native PIP2 (substrate); 3) Stop A (EDTA); 4) Stop B (Biotin-PIP3); 5) Detection Mix A (Streptavidin-APC); 6) Detection Mix B (Eu-labeled Anti-GST plus GST-tagged PH-domain); 7) Detection Mix C (KF). In addition, the following items were obtained or purchased: PI3Kinase (prepared by GSK BR&AD), dithiothreitol (Sigma, D-5545), Adenosine-5'-triphosphate (ATP, Teknova cat. # A0220), native PIP3 (1,2-dioctanoyl-sn-glycero-3-[phosphoinositil-3,4,5-triphosphate]tetraammonium salt (Avanti polar lipids, 850186P), DMSO (Sigma, 472301).

PI3Kinase Reaction Buffer was prepared by diluting the stock 1:4 with de-ionized water. Freshly prepared DTT was added at a final concentration of 5 mM on the day of use. Enzyme addition and compound pre-incubation were initiated by the addition of 2.5 µL of PI3K (at twice its final concentration) in 1× reaction buffer to all wells using a Multidrop Combi. Plates were incubated at room temperature for 15 minutes. Reactions were initiated by addition of 2.5 µL of 2× substrate solution (PIP2 and ATP in 1x reaction buffer) using a Multidrop Combi. Plates were incubated at room temperature for one hour. Reactions were quenched by the addition of 2.5 µL of stop solution (Stop A and Stop B pre-mixed at a ratio of 5:1, respectively) to all wells using the Multidrop Combi. The quenched reactions were then processed to detect product formation by adding 2.5 µL of Detection Solution to all wells using the Mulitdrop Combi (Detection mix C, Detection mix A, and Detection mix B combined together in an 18:1:1 ratio, i.e.: for a 6000 µL total volume, mix 5400 µL Detection mix C, 300 µL Detection mix A, and 300 µL Detection mix B. Note: this solution should be prepared 2 hours prior to use). Following a one hour incubation in the dark, the HTRF signal was measured on the Envision plate reader set for 330 nm excitation and dual emission detection at 620 nm (Eu) and 665 nm (APC).

The loss of the HTRF signal is due to the displacement of biotinylated-PIP3 from the PH domain by the PI3K-dependent conversion of PIP2 to PIP3. This loss of signal is non-linear with respect to both increasing product and time. This non-linear detection will impact accuracy of $IC_{50}$ calculations; therefore, there is a need for a correction factor to obtain more accurate $IC_{50}$ values. This correction is derived from the assay standards in the wells of column 6 and 18 of the assay plate.

All data were calculated using the ratio of acceptor (APC) to donor (Europium) fluorescence in each well of the assay plate. The percent inhibition for each compound concentration was calculated as follows: % inhibition=100*(fluorescence ratio−CtrlB)/(CtrlA−CtrlB) where CtrlA=(−) PI3Kinase reaction and CrtlB=PI3Kinase+DMSO.

An $IC_{50}$ was then calculated fitting the % inhibition data to the equation: % inhibition=min+(max−min)/(1+([inhibitor]/$IC_{50}$)^n) where min is the % inhibition with no inhibitor (typically 0%), max is the signal in the (−) Enzyme control, and n is the Hill slope (typically 1). Finally, the $IC_{50}$ was converted to $pIC_{50}$ ($pIC_{50}$=−log($IC_{50}$)), and the $pIC_{50}$ value was corrected by using plate controls and the equation below:

$pIC_{50}$ (corrected)=$pIC_{50}$ (observed)+log 10((CtrlA−CtrlB)/(CtrlB−CtrlC)), where CtrlA and CtrlB are as defined above and CrtlC=10 μM PI(3,4,5)P3, 100% displacement of biotinylated PI(3,4,5)P3.

The compounds listed in Table 1 were tested generally according to the assays described herein. Table 1 lists the pIC50 values for either an experimental run or an average of two or more experimental runs with the examples shown.

TABLE 1

| Example # | MW | PI3KB PIC50 MEAN |
|---|---|---|
| 3 | 414.51 | 6.7 |
| 5 | 373.46 | 8.8 |
| 11 | 401.51 | 8.7 |
| 13 | 420.34 | 8.1 |
| 14 | 406.32 | 8.5 |
| 15 | 375.45 | 9.0 |
| 17 | 389.48 | 8.6 |
| 18 | 408.31 | 8.0 |
| 20 | 401.47 | 8.2 |
| 22 | 420.30 | 7.8 |
| 25 | 424.51 | 9.6 |
| 31 | 433.43 | 8.2 |
| 32 | 401.30 | 7.9 |
| 35 | 402.46 | 7.2 |
| 38 | 420.30 | 7.0 |
| 39 | 456.48 | 9.2 |
| 41 | 399.50 | 8.8 |
| 43 | 419.45 | 8.3 |
| 50 | 455.44 | 8.9 |
| 53 | 453.85 | 9.3 |
| 54 | 486.42 | 8.6 |
| 58 | 425.50 | 8.2 |
| 59 | 399.88 | 8.2 |
| 63 | 468.32 | 9.0 |
| 70 | 469.42 | 9.7 |
| 72 | 435.86 | 8.8 |
| 73 | 407.50 | 7.6 |

Cellular Assays—Cell Growth Inhibition Assay in PTEN Wild-Type or PTEN Deficient Tumor Cell Lines Twenty-two Phosphatase and Tensin Homolog (PTEN) wild-type or PTEN deficient tumor cell lines were cultured generally according to instructions supplied by cell culture supplier American Type Culture Collection, Manassas, Va., with 10% fetal bovine serum at 5% $CO_2$ and 37° C. Cells were seeded into either a T-75 or a T-175 flask 3-4 days prior to 96-well assay plating such that the flasks were approximately 70-80% confluent at the time of harvest. Cells were harvested using 0.25% trypsin-EDTA (Invitrogen #25200056). Trypan Blue exclusion staining was used to determine cell number.

Viable cells were plated in clear, flat bottom 96-well plates (BD #353075) under anchorage independent conditions at 2,000-10,000 cells per well depending on the cell line. To generate anchorage independent growth conditions, a 5% agar stock solution in water was made and autoclaved to melt and sterilize. From the 5% agar solution, a 0.6% agar/media+10% fetal bovine serum (FBS) solution was made to generate a bottom agar layer in the plates to prevent cell attachment. Seventy five microliters per well of the 0.6% agar-media solution was added to the plates. After solidification, a cell solution of 266,870 to 1,334,022 cells (depending on the cell line) in 10 ml of 0.3% agar/media+10% FBS was made and 75 μl of the cell/media/agar suspension was added to the plates. After the cell layer solidified, 50 μl of media+10% FBS was added to the top of the cells. A 0.3% Brij 35 (Sigma B4184) solution in media+10% FBS was added to column 12 as a background subtraction control. The cells were incubated overnight at 5% $CO_2$ and 37° C. The next day one plate of cells was processed at the time of compound addition to quantify the starting number of cells (T=0 or T0).

To generate the compound titration plates, 15 μl of a 2 mM or 20 μl of a 20 mM solution of the compound of example 31 was diluted in clear bottom polypropylene 96-well plate (BD #351190) using a 10 point, 3-fold titration or a 20 point 2-fold titration, respectively. Three hundred microliters of media was added to the compound dilutions. Ten microliters per well of the serial dilutions was added to the cells and the plates incubated for 6 days at 5% $CO_2$ and 37° C. The final concentration of DMSO in all wells was 0.15% and the highest final concentration of the compound of example 31 was 3.7 μM or 30.7 μM.

Following the 6-day incubation, 20 μl of Alamar Blue (Invitrogen #DAL1100) was added to the cells, incubated at 5% $CO_2$ and 37° C. for 6 hours and the plates read on a Spectramax (Gemini EM) at 530 nm (excitation) and 590 nm (emission) with the auto cut-off disabled. For analysis of cell growth inhibition dose response curves, the data was plotted as the percent of the DMSO-treated control samples (DMSO samples set to 100%). The cellular response was determined for the compound of example 31 and control compounds by fitting the concentration response with a 4 parameter curve fit using XLfit software and determining the concentration that inhibits 50% of the Ymax−Ymin window ($EC_{50}$). The $EC_{50}$ is the midpoint of active compound effect window (between Ymax plateau and Ymin plateau of compound) and represents the concentration of the compound of example 31 where 50% of its maximal effect is observed. Values from wells containing 0.3% Brij 35 (under anchorage independent conditions) were subtracted from all samples for background correction.

The results shown in Table 2 demonstrate that multiple cell lines with loss of the tumor suppressor PTEN were sensitive, while relatively few wild-type PTEN tumor cell lines were sensitive.

TABLE 2

Anchorage Independent Soft Agar Tumor Growth Assay

| Cell line | Origin | Type | PTEN Mutation/Copy Number Status | PTEN Western Analysis | Compound $EC_{50}$ (nM) ± StDev | Ymin ± StDev |
|---|---|---|---|---|---|---|
| BT549 | breast | carcinoma | p.V275fs*1 | No protein | 7 ± 2 | 52 ± 7 |
| WM-115 | skin | melanoma | p.165fs* | No protein | 8 ± 3 | 54 ± 14 |
| C32 | skin | melanoma | p.55fs* | No protein | 8 ± 2 | 20 ± 14 |
| SW1783 | CNS | glioblastoma | p.R233* | No protein | 10 ± 3 | 69 ± 4 |
| UM-UC-3 | bladder | transitional | Loss | No protein | 10 ± 8 | 83 ± 29 |
| SW1088 | CNS | glioblastoma | Loss | No protein | 12 ± 6 | 36 ± 8 |
| H4 | CNS | glioblastoma | Loss | No protein | 12 ± 8 | 55 ± 18 |
| CHL-1 | skin | melanoma | Wild-type | Protein | 14 ± 6 | 82 ± 2 |

TABLE 2-continued

Anchorage Independent Soft Agar Tumor Growth Assay

| Cell line | Origin | Type | PTEN Mutation/Copy Number Status | PTEN Western Analysis | Compound EC$_{50}$ (nM) ± StDev | Ymin ± StDev |
|---|---|---|---|---|---|---|
| UACC-62 | skin | melanoma | p.P248fs*5 | No protein | 23 ± 27 | 76 ± 18 |
| HCC19377 | breast | carcinoma | Loss | No protein | 24 ± 8 | 67 ± 8 |
| PC-3 | prostate | carcinoma | Loss | No protein | 27 ± 12 | 82 ± 13 |
| HCC70 | breast | carcinoma | p.F90fs*9 | No protein | 53 ± 21 | 27 ± 8 |
| MDA-MB-468 | breast | carcinoma | p.?, L70Fs*7 | No protein | 89 ± 55 | 44 ± 6 |
| HCC1395 | breast | carcinoma | p.N212fs*3 | No protein | 114 ± 53 | 26 ± 9 |
| U-87MG | CNS | glioblastoma | p.? | No protein | 2975 ± 2771 | 34 ± 18 |
| B1474 | breast | carcinoma | Wild-type | Protein | 3360 ± 868 | 75 ± 3 |
| U251 | CNS | glioblastoma | p.E242fs*15 | No protein | 18996 ± 8625 | 80 ± 17 |
| HCC1954 | breast | carcinoma | Wild-type | Protein | >30722 | >80 |
| Colo205 | colon | carcinoma | Wild-type | ND | >30722 | >80 |
| HCT-116 | colon | carcinoma | Wild-type | ND | >30722 | >80 |
| SKOV-3 | ovary | adenocarcinoma | Wild-type | ND | >30722 | >80 |
| LOXIMVI | skin | melanoma | Wild-type | Protein | >30722 | >90 | p.? indicates a splice site mutation

In Vivo Experiments
Dose Dependent Tumor Inhibition

The activity of the compound of example 31 was evaluated in vivo against PC-3 (prostate carcinoma cell line encoding a deficient PTEN protein) xenograft mouse model. The PC-3 tumor bearing mice were generated by injecting 2.5×10$^6$ PC-3 cells suspended 1:1 in Matrigel subcutaneously in the flank of female nude mice (Charles River—Wilmington; strain Crl: CD-1-Foxn1). One set of mice, each approximately 19 weeks of age, were implanted with the cells for the 100, 30, and 10 mg/kg doses and another set of mice, each approximately 11 weeks of age, were implanted with the cells for the 10, 3, and 1 mg/kg doses.

Mice bearing PC-3 xenografts were randomized into dosing groups of n=8 based on tumor volume 29 (100, 30, and 10 mg/kg) or 28 (1, 3, 10 mg/kg) days after tumor cells were implanted. Treatment of mice commenced the next day and continued for 21 days. Mice received once daily oral gavage with compound or vehicle at 10 mL/kg.

Tumor growth was measured twice weekly in two dimensions with vernier callipers; the longest dimension was defined as the length (l), and the width (w) was measured perpendicular to the length. Tumor volumes (V) were calculated using the following equation: V=(½)lw$^2$. Means of the tumor volumes were used to compare treatment groups. Stable disease for this study is defined as a tumor volume which during the course of compound treatment does not substantially increase or decrease but stays similar to the volume prior to drug treatment compared to vehicle treated in which the tumor volume continues to increase during the course of the study. Tumor growth delay is defined as tumor volume that is reduced during the course of the compound treatment relative to vehicle treated tumor volume.

The results demonstrated that treatment of female nude mice bearing PC-3 prostate xenografts with 10, 30, and 100 mg/kg the compound of example 31 for 21 days resulted in stable disease with the 1 and 3 mg/kg doses resulting in tumor growth delay relative to vehicle during the dosing period.
B) Pharmacodynamic Effects The activity of the compound of example 31 was evaluated in vivo against PC-3 (prostate carcinoma cell line encoding a deficient PTEN protein) xenograft mouse model. Female nude mice (Charles River Laboratories, Wilmington, Del.; strain CD-1-Foxn1, ~6 weeks of age) were injected subcutaneously with 2 million PC-3 (human prostate carcinoma) cells mixed 1:1 with Matrigel in the flank. Tumors were allowed to grow for approximately 5 weeks.

Mice bearing PC-3 xenografts were administered 3 mg/kg of the compound of example 31 or 10 mg/kg of the compound of example 31 and euthanized using carbon dioxide after 1, 2, 4, 6, 8, 10, and 24 hours (n=3 mice/treatment/timepoint); an additional 3 mice bearing PC-3 xenografts were administered vehicle and euthanized after 2 hours. The tumor was excised. Half of each tumor was immediately processed by Medicon (BD Catalog #340592) in 1 mL Meso-Scale Discovery (MSD) lysis buffer with protease inhibitors (Roche complete protease cocktail, cat #04 693 116 001) and phosphatase inhibitors (Sigma, cat # P2850 and P-5726) for 30-60 seconds and transferred to 1.5 mL Eppendorf tubes. Tubes remained on wet ice until they were centrifuged for 10 minutes at 4° C. at maximum speed in a tabletop refrigerated centrifuge.

Tumor lysates were serially diluted in 96-well polypropylene plates on wet ice. Lysates (150 µL) were loaded in row 1; rows 2-12 were loaded with 75 µL of complete Meso Scale Discovery (MSD) lysis buffer (supplied in MSD kit; # K15100D-3). Samples were serially diluted 2-fold across the plate by sequential transfer of 75 µL through well 11; row 12 contained lysis buffer only. MSD Multi-Spot assay plates (whole cell lysate kit: Phospho(ser473), Total AKT Assay, catalog #K15100D-3) were blocked with 150 µL of 3% Blocker A overnight at 4° C. with shaking before being washed 4× with 200 µL MSD Tris wash buffer. Fifty microliters of the serially diluted lysates were pipetted onto the blocked MSD plates, covered, and incubated overnight at 4° C. with shaking. Plates were washed with Tris buffer as before. Detection antibody was added (25 µL/well) at a final concentration of 10 nM in 1 mL Blocker A and 2 mLTris wash buffer and incubated for 1 hour at room temperature with shaking. Plates were washed as described above, before the addition of 150 µL of MSD read buffer and read immediately on a 6000 MSD plate reader. All work was performed in accordance with Institutional Animal Care and Use Committee (IACUC) protocols PA0079 and PA0271.

The non-lysate controls in column 12 were averaged and used as background to subtract from all wells. P/T AKT was calculated as shown: (phospho AKT(Ser473) signal)/[(phospho AKT(Ser473) signal)+(total AKT signal)]. Values from three points in each row of diluted samples identified as being in the linear range of detection were averaged to represent each tumor sample's P/T AKT value. Averages and standard deviations of the P/T AKT value for each group of 3 mice were determined Percent inhibition was calculated for each group as follows: 100-[(sample P/T AKT value)/(vehicle P/T AKT value)]*100.

The compound of example 31 exhibited dose dependent inhibition of the pharmacodynamic marker pAKT (pAKT/tAKT).

Additional References:

The compounds of the present invention can also be tested to determine their inhibitory activity at PI3Kα, PI3Kδ, PI3Kβ and PI3Kγ according to international patent publication No. WO2009/039140.

The pharmaceutically active compounds within the scope of this invention are useful as PI3 Kinase inhibitors in mammals, particularly humans, in need thereof.

The present invention therefore provides a method of treating diseases associated with PI3 kinase inhibition, particularly: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries and other conditions requiring PI3 kinase modulation/inhibition, which comprises administering an effective compound of Formula (I) or a pharmaceutically acceptable salt, hydrate, solvate or prodrug thereof. The compounds of Formula (I) also provide for a method of treating the above indicated disease states because of their ability to act as PI3 inhibitors. The drug may be administered to a patient in need thereof by any conventional route of administration, including, but not limited to, intravenous, intramuscular, oral, subcutaneous, intradermal, and parenteral.

Exemplary Capsule Composition

An oral dosage form for administering the present invention is produced by filing a standard two piece hard gelatin capsule with the ingredients in the proportions shown in Table 3, below.

TABLE 3

| INGREDIENTS | AMOUNTS |
| --- | --- |
| Compound of example 1 | 25 mg |
| Lactose | 55 mg |
| Talc | 16 mg |
| Magnesium Stearate | 4 mg |

Exemplary Injectable Parenteral Composition

An injectable form for administering the present invention is produced by stirring 1.5% by weight of compound of example 1 in 10% by volume propylene glycol in water.

Exemplary Tablet Composition

The sucrose, calcium sulfate dihydrate and an PI3K inhibitor as shown in Table 4 below, are mixed and granulated in the proportions shown with a 10% gelatin solution. The wet granules are screened, dried, mixed with the starch, talc and stearic acid; screened and compressed into a tablet.

TABLE 4

| INGREDIENTS | AMOUNTS |
| --- | --- |
| Compound of example 1 | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A process for making the compound of formula (4)

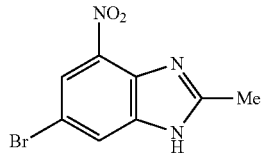

comprising the steps of
brominating a 2,6-dinitro aniline to provide a 4-bromo-2,6-dinitroaniline, reducing said 4-bromo-2,6-dinitroaniline to provide a di-amino nitro benzene, and reacting said di-amino nitro benzene with 2,4-pentanedione to provide the compound of formula (4).

2. The process of claim 1, wherein the step of brominating comprises brominating a 2,6-dinitro aniline with bromine in acetic acid.

3. The process of claim 1, wherein the step of reducing comprises reducing said 4-bromo-2,6-dinitroaniline with $(NH_4^+)_2S$.

4. The process of claim 1, wherein the reacting of said di-amino nitro benzene with 2,4-pentanedione is preformed in the presence of a strong acid at reflux temperatures in an alcoholic solvent.

* * * * *